United States Patent
Boettner

(10) Patent No.: US 11,241,287 B2
(45) Date of Patent: Feb. 8, 2022

(54) FLUOROSCOPY-BASED MEASUREMENT AND PROCESSING SYSTEM AND METHOD

(71) Applicant: Friedrich Boettner, Larchmont, NY (US)

(72) Inventor: Friedrich Boettner, Larchmont, NY (US)

( * ) Notice: Subject to any disclaimer, the term of this patent is extended or adjusted under 35 U.S.C. 154(b) by 274 days.

(21) Appl. No.: 16/163,504

(22) Filed: Oct. 17, 2018

(65) Prior Publication Data

US 2019/0090962 A1 Mar. 28, 2019

Related U.S. Application Data

(63) Continuation-in-part of application No. 15/501,671, filed as application No. PCT/US2016/045710 on Aug. 5, 2016, now Pat. No. 10,238,454.

(Continued)

(51) Int. Cl.
*A61B 34/10* (2016.01)
*A61B 17/17* (2006.01)
(Continued)

(52) U.S. Cl.
CPC .............. *A61B 34/20* (2016.02); *A61B 6/12* (2013.01); *A61B 6/487* (2013.01); *A61B 17/1703* (2013.01); *A61B 17/1746* (2013.01); *A61B 34/10* (2016.02); *A61B 34/25* (2016.02); *A61F 2/32* (2013.01); *A61F 2/4609* (2013.01); *A61F 2/4657* (2013.01); *A61B 6/4441* (2013.01); *A61B 17/15* (2013.01); *A61B 17/1666* (2013.01); *A61B 2017/0092* (2013.01);
(Continued)

(58) Field of Classification Search
CPC .... A61B 34/10; A61B 2034/107; A61B 17/17
See application file for complete search history.

(56) References Cited

U.S. PATENT DOCUMENTS

| | | | | |
|---|---|---|---|---|
| 5,951,475 A | * | 9/1999 | Gueziec | G06T 3/0068 600/425 |
| 6,711,432 B1 | * | 3/2004 | Krause | A61B 17/15 128/922 |

(Continued)

OTHER PUBLICATIONS

Bae, Jung Yun, "The best method for evaluating anteversion of the acetabular component after total hip arthroplasty on plain radiographs" Apr. 2, 2018, Journal of Orthopaedic Surgery and Research, site visited May 7, 2020: https://josr-online.biomedcentral.com/articles/10.1186/s13018-018-0767-4 (Year: 2018).

(Continued)

*Primary Examiner* — Nicholas W Woodall
(74) *Attorney, Agent, or Firm* — Leason Ellis LLP

(57) ABSTRACT

A fluoroscopy-based system/method for correcting at least an inclination angle of an acetabular cup during total hip arthroplasty. A computing device processes an image of the surgical area to determine distortion, at least as a function of the reference object in the image. Thereafter, the computing device generates a correction factor and measures an inclination angle of an initially positioned acetabular cub in an anterior posterior image of a patient's pelvis, and corrects, as a function of the correction factor, the measured inclination angle to provide an accurate inclination angle of the acetabular cup.

16 Claims, 44 Drawing Sheets

Related U.S. Application Data

(60) Provisional application No. 62/573,288, filed on Oct. 17, 2017, provisional application No. 62/201,417, filed on Aug. 5, 2015.

(51) Int. Cl.

| | | |
|---|---|---|
| *A61B 34/20* | (2016.01) | |
| *A61F 2/46* | (2006.01) | |
| *A61F 2/32* | (2006.01) | |
| *A61B 6/00* | (2006.01) | |
| *A61B 34/00* | (2016.01) | |
| *A61B 6/12* | (2006.01) | |
| *A61B 17/16* | (2006.01) | |
| *A61B 17/15* | (2006.01) | |
| *A61B 90/00* | (2016.01) | |
| *A61B 17/00* | (2006.01) | |

(52) U.S. Cl.
CPC ... *A61B 2034/104* (2016.02); *A61B 2034/107* (2016.02); *A61B 2034/108* (2016.02); *A61B 2034/2068* (2016.02); *A61B 2034/254* (2016.02); *A61B 2090/376* (2016.02)

(56) References Cited

U.S. PATENT DOCUMENTS

| | | | |
|---|---|---|---|
| 9,056,020 B1 | 6/2015 | Termanini | |
| 9,402,726 B2* | 8/2016 | Linderman | A61B 17/155 |
| 2004/0044295 A1* | 3/2004 | Reinert | A61B 34/20 |
| | | | 600/587 |
| 2004/0087852 A1 | 5/2004 | Chen et al. | |
| 2004/0127788 A1* | 7/2004 | Arata | A61B 6/5247 |
| | | | 600/424 |
| 2004/0181149 A1 | 9/2004 | Langlotz et al. | |
| 2008/0051910 A1 | 2/2008 | Kammerzell et al. | |
| 2008/0056552 A1 | 3/2008 | Muler | |
| 2011/0144704 A1 | 6/2011 | Switzer | |
| 2011/0188726 A1* | 8/2011 | Nathaniel | A61B 6/025 |
| | | | 382/132 |
| 2014/0213889 A1 | 7/2014 | Macht | |
| 2015/0023827 A1 | 1/2015 | Jang et al. | |
| 2015/0088146 A1 | 3/2015 | McCarthy | |
| 2015/0238271 A1 | 8/2015 | Wollowick et al. | |
| 2017/0224418 A1 | 8/2017 | Boettner et al. | |
| 2017/0312031 A1* | 11/2017 | Amanatullah | G09B 23/30 |

OTHER PUBLICATIONS

Atoun, Ehud, Anteversion of the Acetabular Cup Determined by Digital Radiographic Software as Compared to CT-Based v Measurement: Dec. 28, 2016, International Journal of Orthopaedics, site visited May 8, 2020: http://www.ghrnet.org/index.php/ijo/article/view/1795/2273 (Year: 2016).

Murray, D.W., "The Definition and Measurement of Acetabular Orientation", The Journal of Bone and Joint Surgery,1993. pp. 228-232.

Ross, James R. et al., "Functional Acetabular Orientation Varies Between Supine and Standing Radiographs: Implications for Treatment of Femoroacetabular Impingement", Clinical Orthopaedics and Related Research, 473:1267-1273, Published Jan. 6, 2015.

Goergen and Resnick, "Evaluation of acetabular anteversion following total hip arthroplasty: necessity of proper centring," Apr. 1975; British Journal of Radiology, 48, 259-260.

Lembeck, Burkhard et al., "Pelvic tilt makes acetabular cup navigation Inaccurate", Acta Orthopaedica, 76 (4): 517-523, Submitted Mar. 4, 2011.

Schwarz, Weber et al., "Central X-ray beam correction of radiographic acetabular cup measurement after THA: an experimental study", Int J CARS (2017) 12:829-837; Apr. 25, 2016.

Schrading and Schulze, "Preoperative diagnostic imaging and planning", Aug. 2016; vol. 45, Issue 8, pp. 644-652; First Published Online Jul. 20, 2016.

Lewinnek, George et al., "Dislocations after Total Hip-Replacement Arthroplasties", The Journal of Bone and Joint Surgery, vol. 60-A, No. 2, Mar. 1978; pp. 217-220.

Widmer et al., "A Simplified Method to Determine Acetabular Cup Anteversion From Plain Radiographs", The Journal of Arthroplasty, vol. 19, No. 3 Submitted Nov. 11, 2002; pp. 387-390.

* cited by examiner

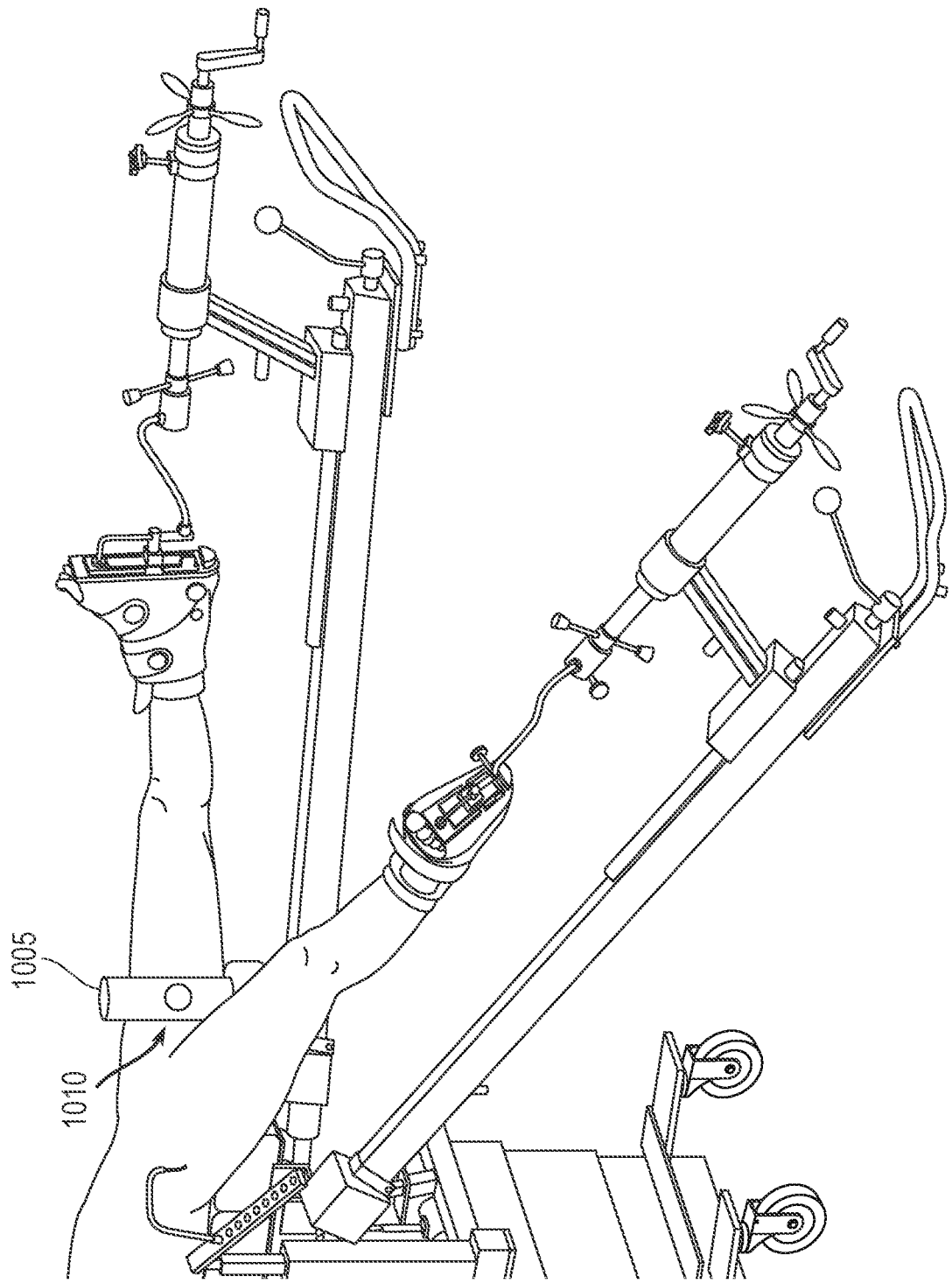

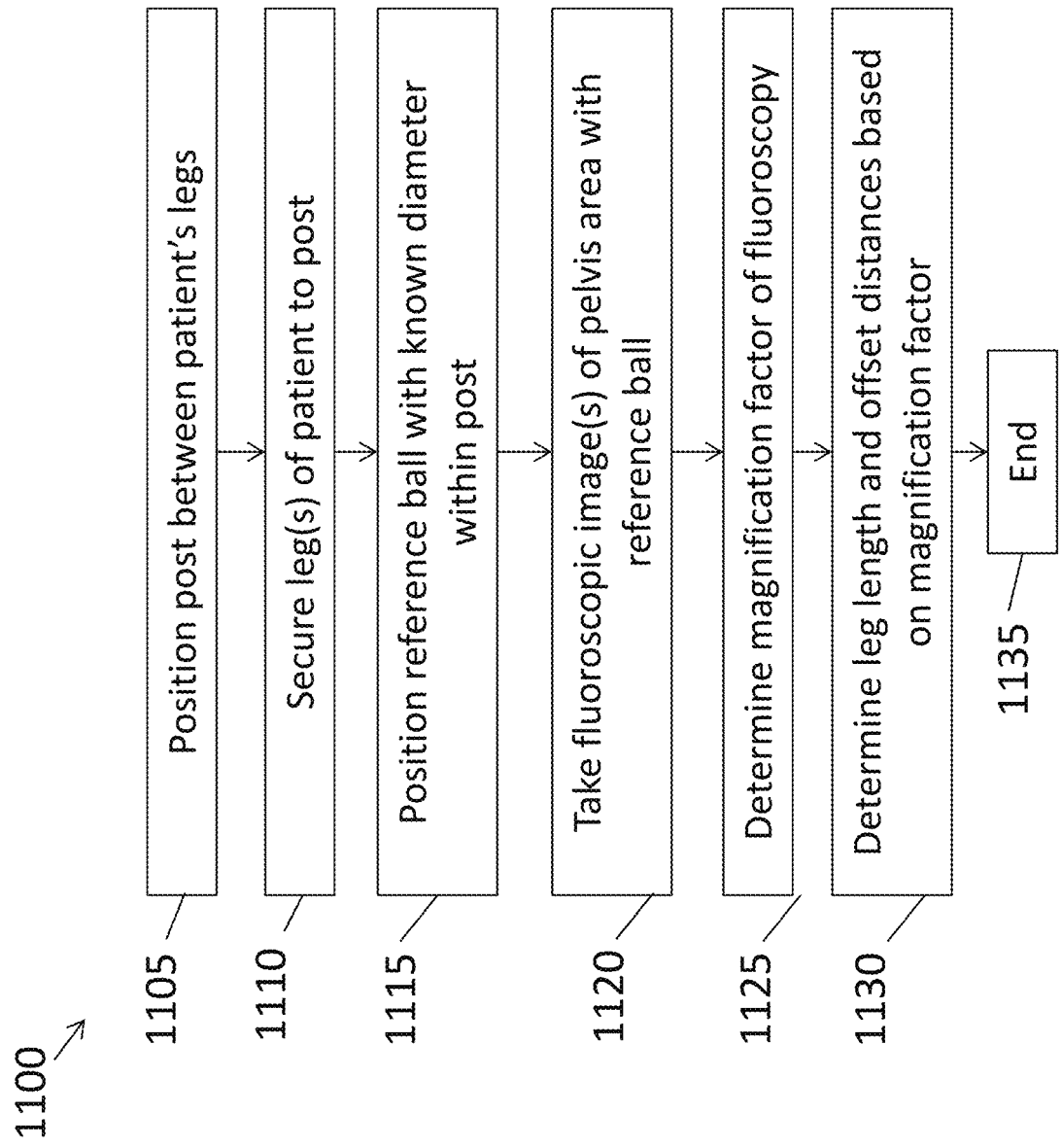

FLUOROSCOPY-BASED MEASUREMENT AND PROCESSING SYSTEM AND METHOD

CROSS REFERENCE TO RELATED APPLICATION

This application is based on and claims priority to U.S. Provisional Patent Application No. 62/573,288, filed Oct. 17, 2017, and this application is a continuation-in-part of U.S. Non Provisional patent application Ser. No. 15/501, 671, filed Feb. 3, 2017, which is a U.S. National Phase Application under 35 U.S.C. § 371 of International Patent Application No. PCT/US16/45710, filed Aug. 5, 2016, which claims priority to U.S. patent application Ser. No. 62/201,417, filed Aug. 5, 2015, all of which are incorporated by reference, as if expressly set forth in their respective entireties herein.

TECHNICAL FIELD

The present invention relates to total hip arthroplasty and more specifically, relates to techniques for determining hip measurements during total hip arthroplasty operations using fluoroscopy.

BACKGROUND

Total hip arthroplasty (THA), also referred to as surgical replacement of the hip joint with an artificial prosthesis or total hip replacement, is a reconstructive procedure in which damaged bone and cartilage of the hip are removed and replaced with prosthetic components. THA is frequently the preferred treatment option for people with late-stage degenerative hip disease; however, chronic pain and impairment of daily function of patients with severe hip arthritis are also reasons for considering treatment with total hip replacement.

In THA, one of the components that is needed to reconstruct the hip is an acetabular cup which is used to replace the natural socket of the patient which is called the acetabulum. The acetabular cup is the part of the hip implant that forms the socket in the ball-and-socket structure of the hip joint. The femoral head at the top of the femur rotates within the curved surface of the acetabulum. Accordingly, the THA procedure involves replacing the acetabulum (socket) with the acetabular cup and a femoral implant that includes a femoral head (ball) and a stem that attaches to the femur bone.

Implant positioning is of critical importance in primary THA. Acetabular cup position is traditionally described by its centre of rotation (acetabular component offset), its anteversion (CV), and its inclination (CI, also termed abduction). Incorrect acetabular cup placement is associated with higher dislocation rates, range of motion limitations due to impingement, eccentric polyethylene wear and, ultimately, higher rates of revision.

Conventional techniques used to determine acetabular cup position include external alignment guides, free-hand positioning and the use of anatomic landmarks. Previous studies demonstrated that these techniques allow for correct positioning of the acetabular component in the target zone in only 50-86% of the cases. In order to avoid implant malposition, a variety of imageless and image-based navigation techniques have been developed.

One surgical technique for THA is referred to as the direct anterior approach (DAA). In general, direct anterior hip replacement is a minimally invasive surgical technique which involves an incision of about 3 to 4 inches on the front of the hip that allows the joint to be replaced by moving muscles aside along their natural tissue planes, without detaching any tendons.

The introduction of DAA with the patient lying in a supine position has greatly facilitated the use of intraoperative fluoroscopy. Fluoroscopy is a type of medical imaging that shows continuous X-ray images on a display. During a procedure involving fluoroscopy, an X-ray beam is passed through the body. Fluoroscopic control during THA provides anterior posterior (AP) images of the hip, which can improve acetabular cup placement. However, determining accurate measurements of the pelvis and hip area of a patient as well as the hip implant via the fluoroscopic AP images can still prove problematic due to issues associated with magnification and distortion in fluoroscopic images. Inaccuracies in the measurements of the hip area or the hip implant can lead to inaccuracies in implant positioning.

Accordingly, there is a need for improved methods for accurate measurement of the hip area and hip implants during THA using intraoperative fluoroscopy.

BRIEF SUMMARY

In one or more implementations, the present application provides a fluoroscopy-based system and method for correcting at least an inclination angle of an acetabular cup during total hip arthroplasty. A surgical area is configured with a reference object having a known diameter, wherein the reference object is positioned relative to a patient and relative to an imaging device. An imaging unit captures an image of the surgical area. A computing device configured by executing code stored in non-transitory processor readable media processes an image of the surgical area to determine distortion, at least as a function of the reference object in the image. Thereafter, the computing device generates a correction factor that, when applied to at least a portion of an image taken by the imaging unit, corrects for the distortion. The computing device measures an inclination angle of an initially positioned acetabular cub in an anterior posterior image of a patient's pelvis, and corrects, as a function of the correction factor, the measured inclination angle to provide an accurate inclination angle of the acetabular cup. The distortion further can include at least parallax image distortion that affects a measured angle of an area of interest and/or a proportion of the angle. Moreover, the parallax distortion results from the acetabular cup location being outside a central beam of the imaging device.

In one or more implementations, the computing device provides the anterior posterior image including the acetabular cup in a graphical user interface. A graphical overlay is included in the graphical user interface on the acetabular cup usable to indicate whether the acetabular cup appears spherical, and a connecting line is provided between two anatomical landmarks, wherein the line is usable to describe tilt or orientation of the patient's pelvis. Further, at least one selectable element in the graphical user interface is usable to select an area of interest. Moreover, in one or more implementations the computing device adjusts a measured angle of the selected area of interest and/or a proportion of the angle proportion as a function of the partially rotated selected area of interest.

Still further, in one or more implementations, the computing device is configured to instruct a robotic element to position a C-arm of the imaging device to move a central beam associated with the imaging device until the acetabular cup appears spherical.

Still further, in one or more implementations the computing device provides the anterior posterior image including the acetabular cup in a graphical user interface and calculates, a degree of anteversion of the acetabular cup. In the graphical user interface, reference lines are superimposed over the acetabular cup, representing a comparison of a measured degree of anteversion and a target degree of anteversion.

These and other aspects, features, and advantages in accordance with the present application can be appreciated from the following description of certain embodiments and the accompanying drawing figures.

BRIEF DESCRIPTION OF DRAWING FIGURES

FIG. 1 is a perspective view of a hip area of a patient in which: $\vec{n}_{rim}$ is the vector normal to the plane of the rim of the cup and is defined by the inclination angle CI and the anteversion angle CV; aCV is the angle between the projection of $\vec{n}_{rim}$ on the transverse plane and the coronal plane; $\vec{n}_{ia}$ is the vector normal to a plane of the image amplifier; and CaT is the tilt angle that needs to be applied to the c-arm to make the plane of the image amplifier perpendicular to the plane of the rim of the acetabular cup (corresponding to the angle between $\vec{n}_{ia}$ and the z-axis);

Figure 4:
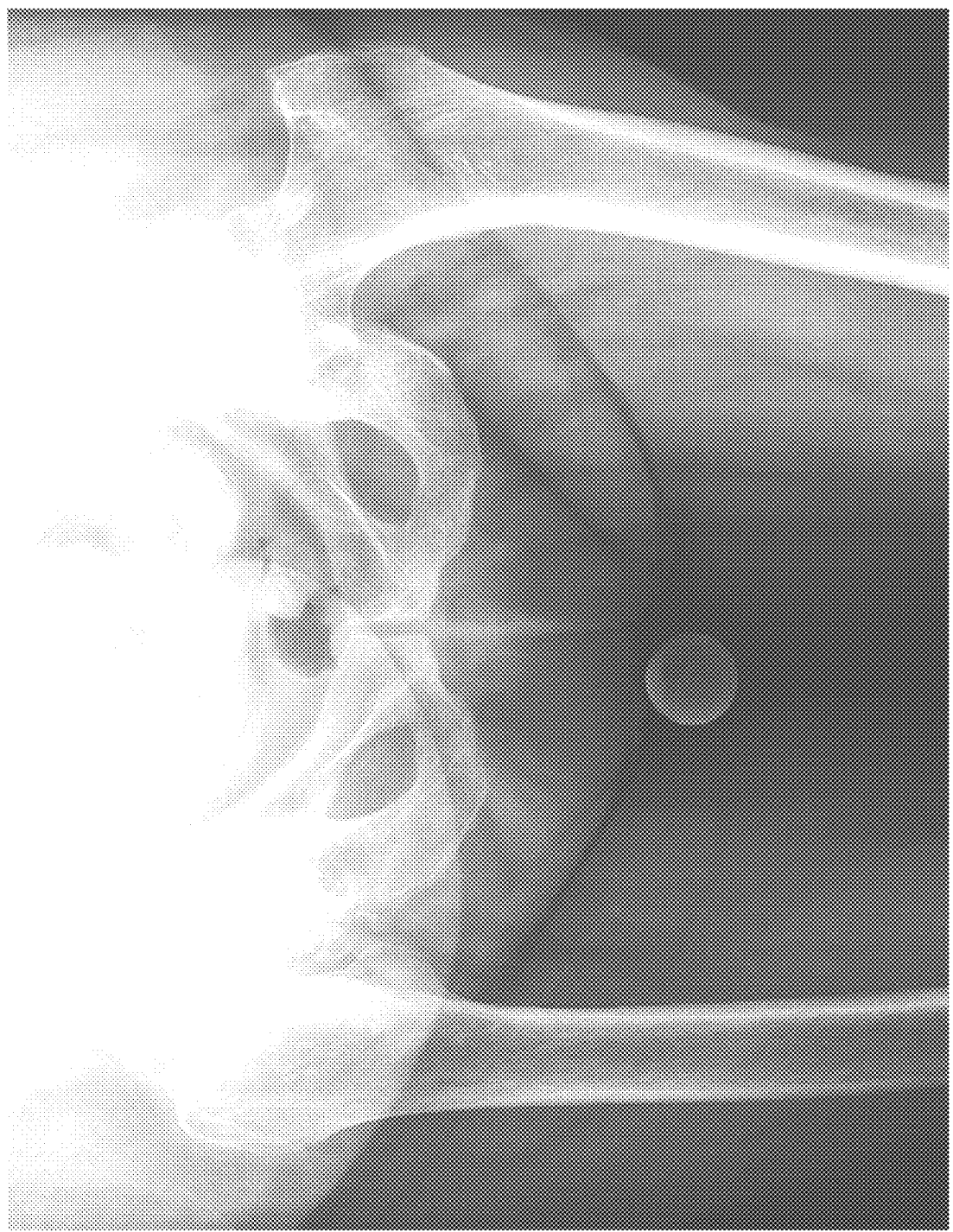
Figure 5:
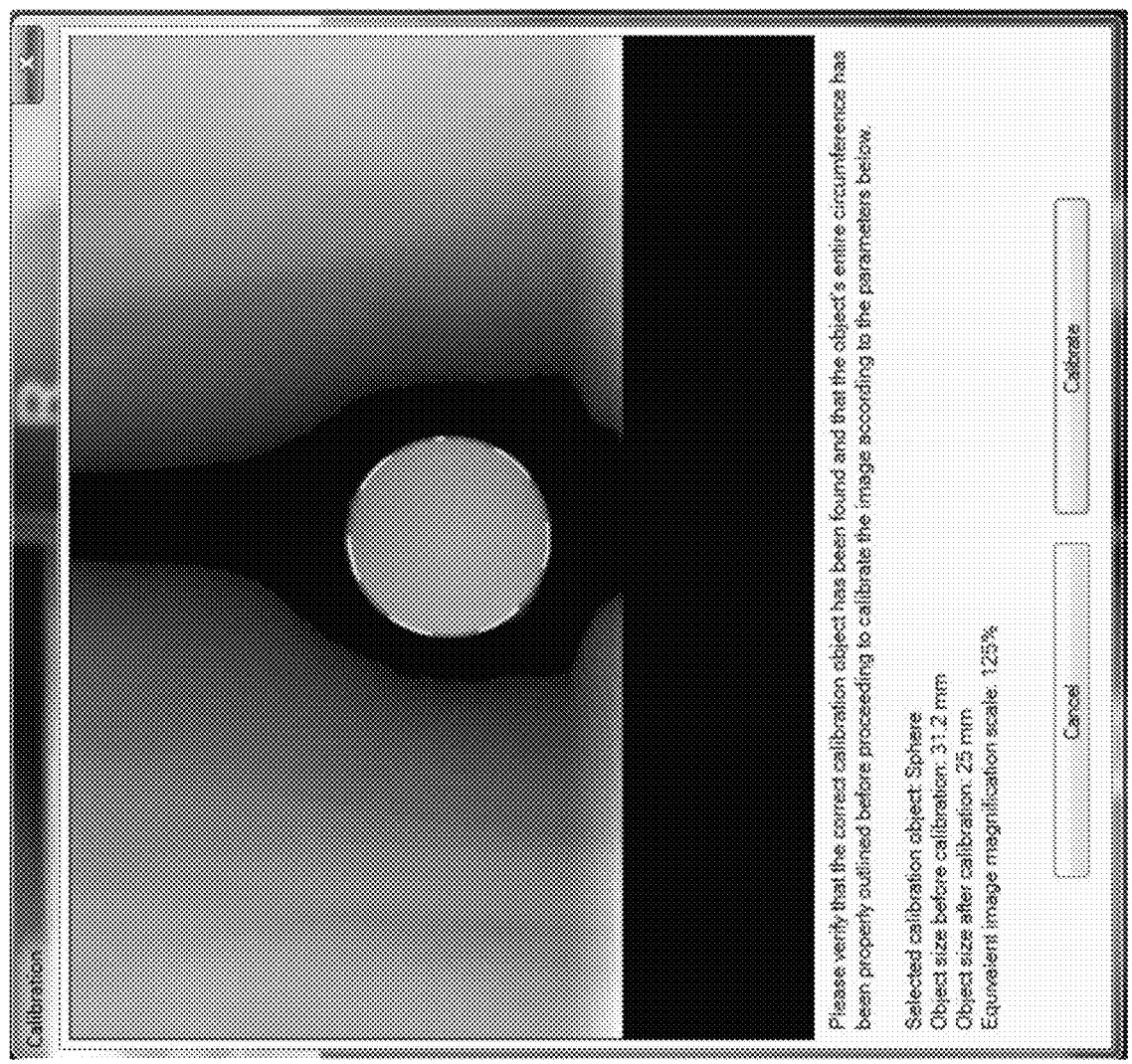
Figure 6A:
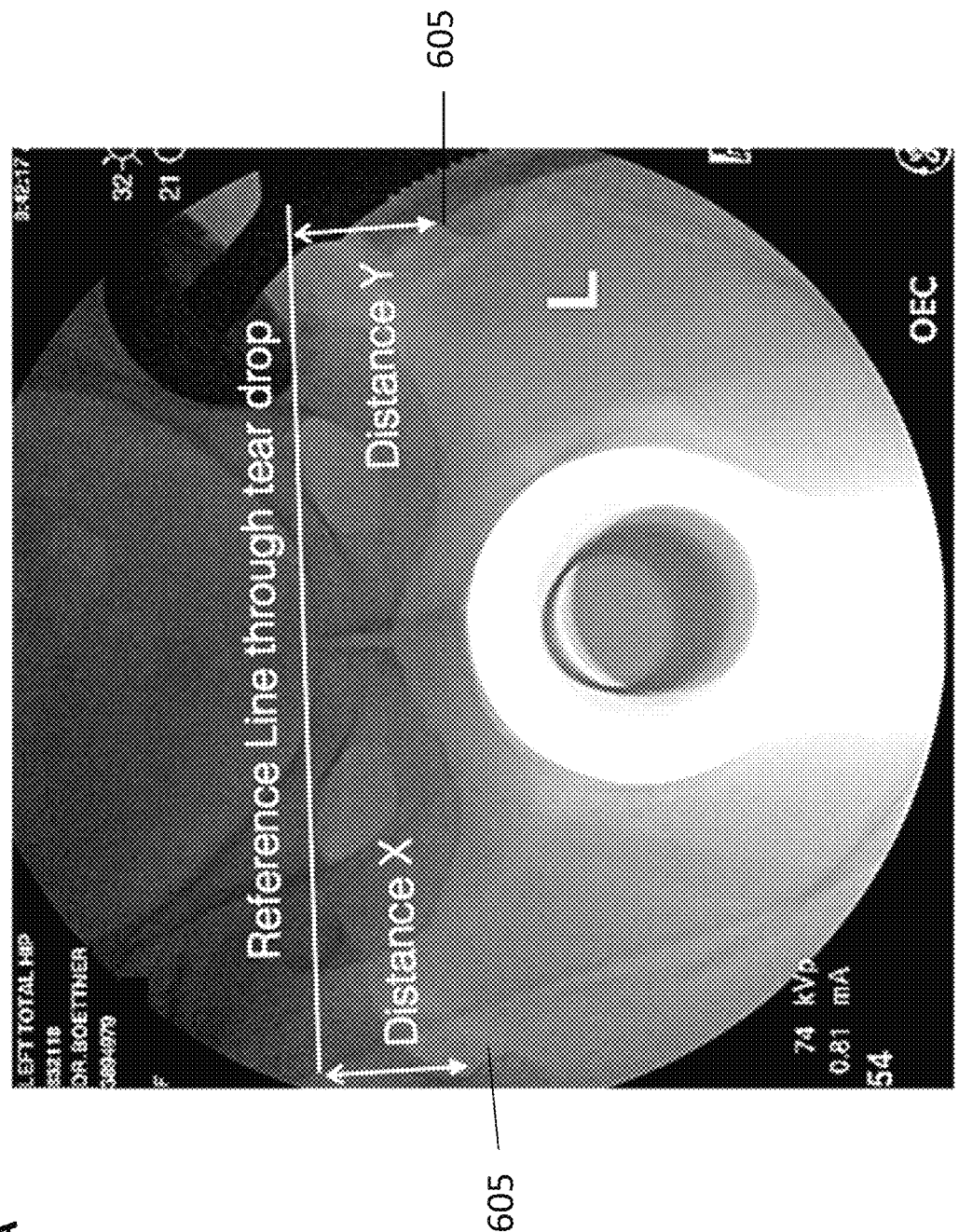
Figure 7:
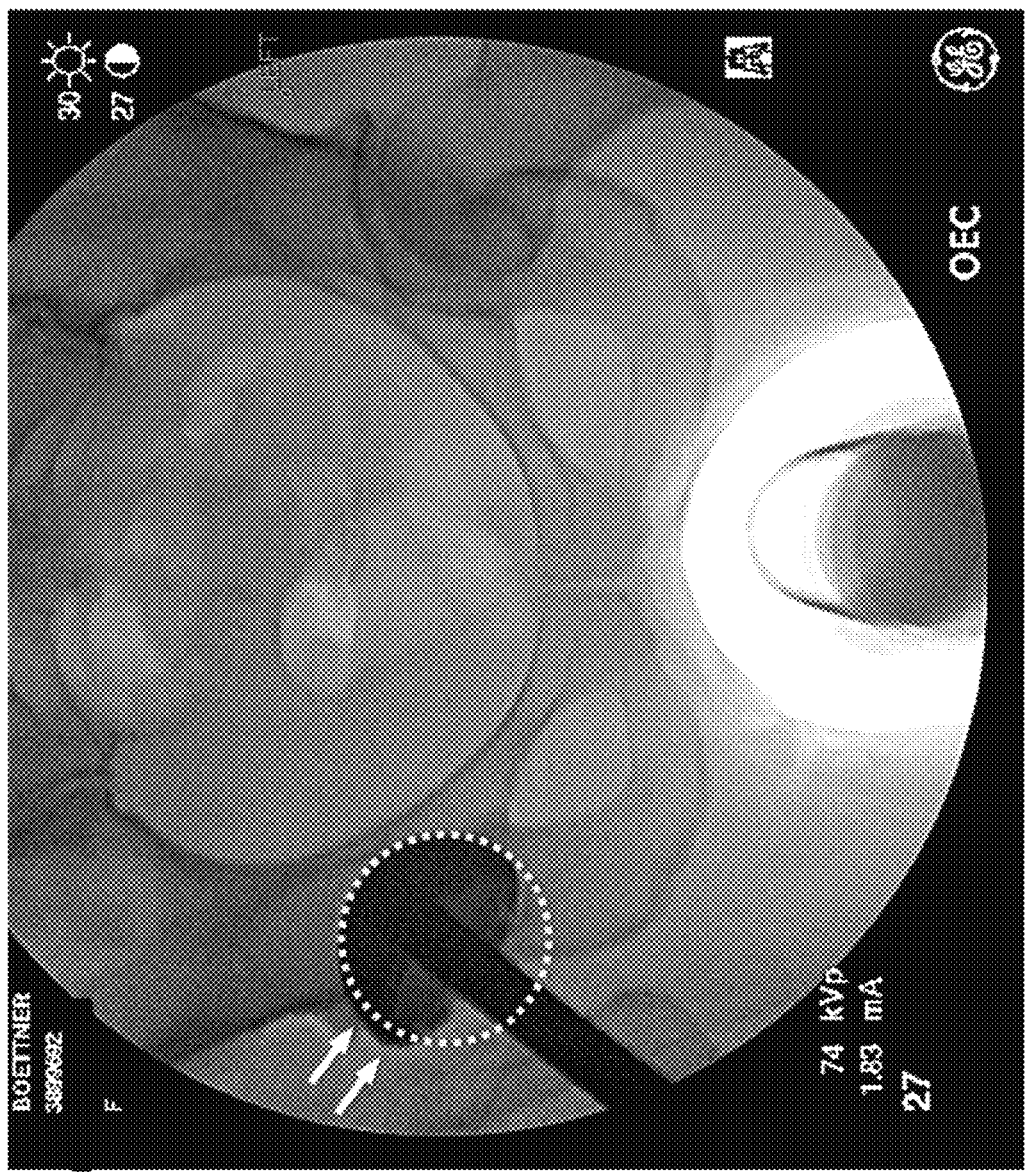
Figure 8:
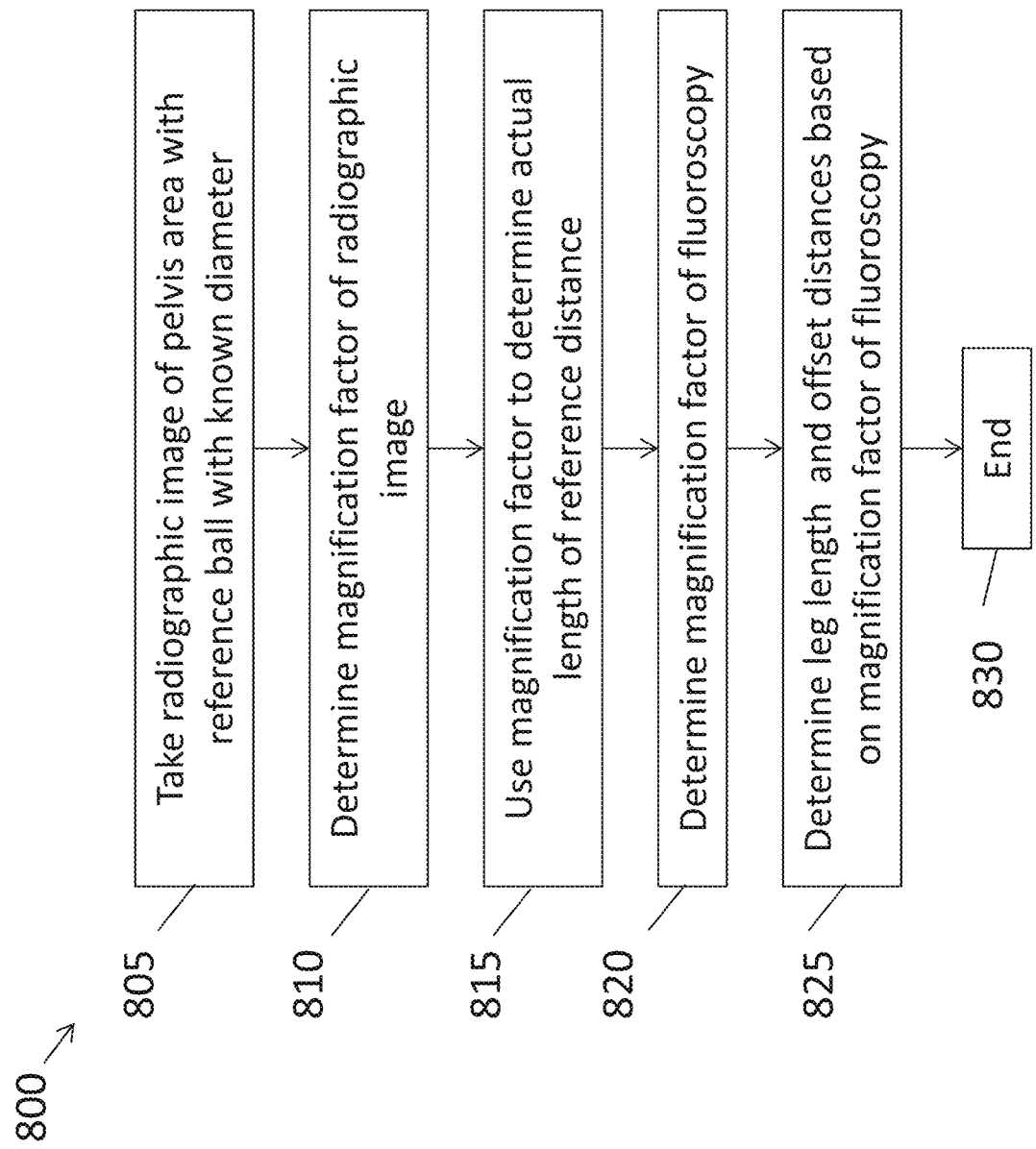
Figure 9:
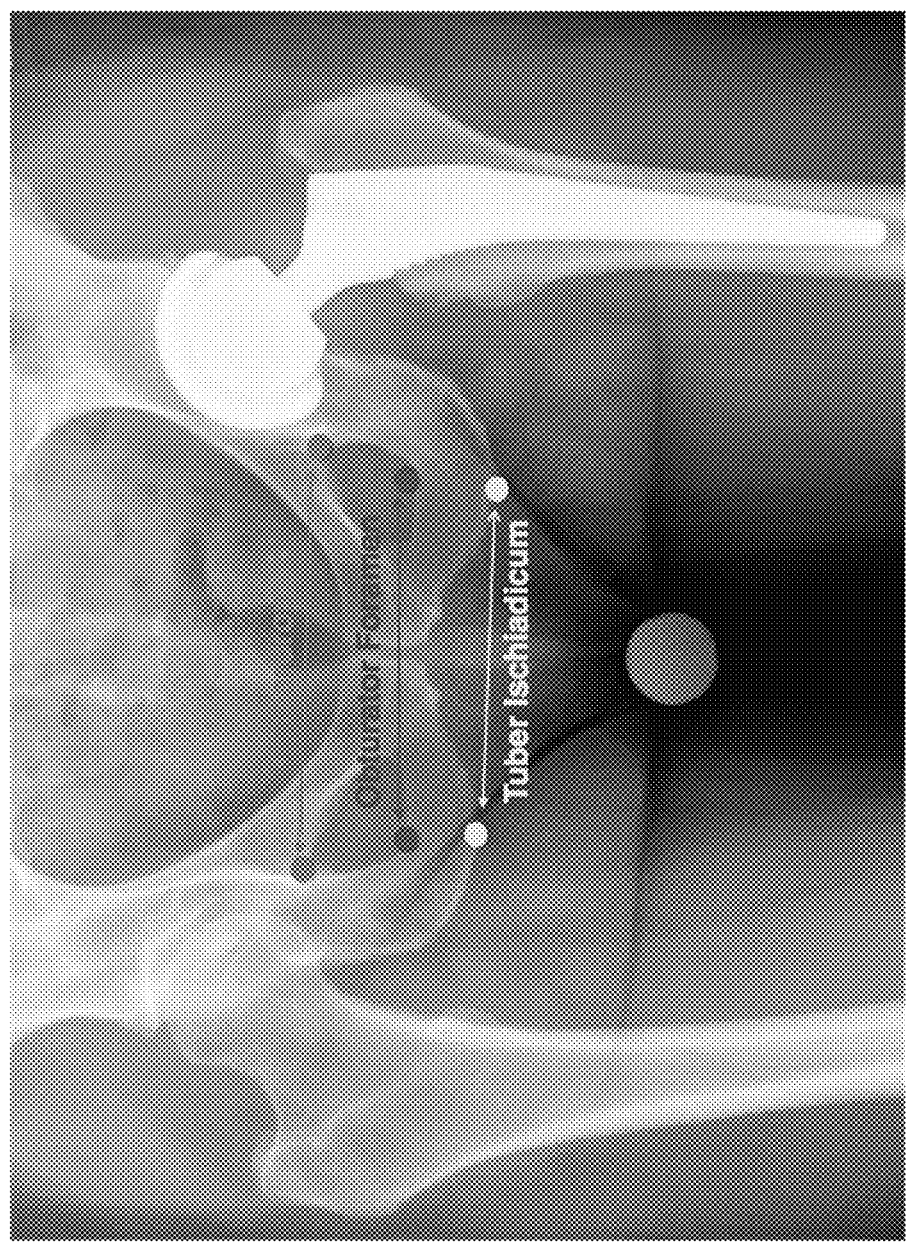
Figure 10B:
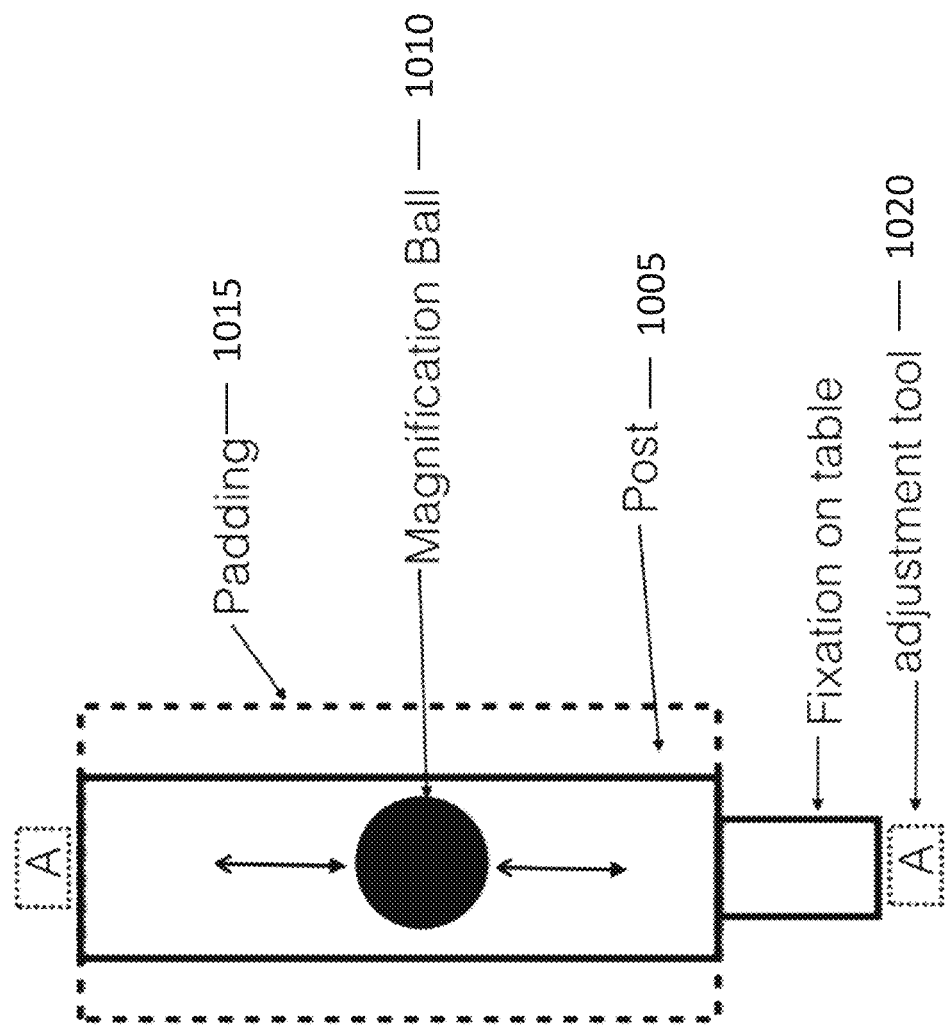
Figure 10C:
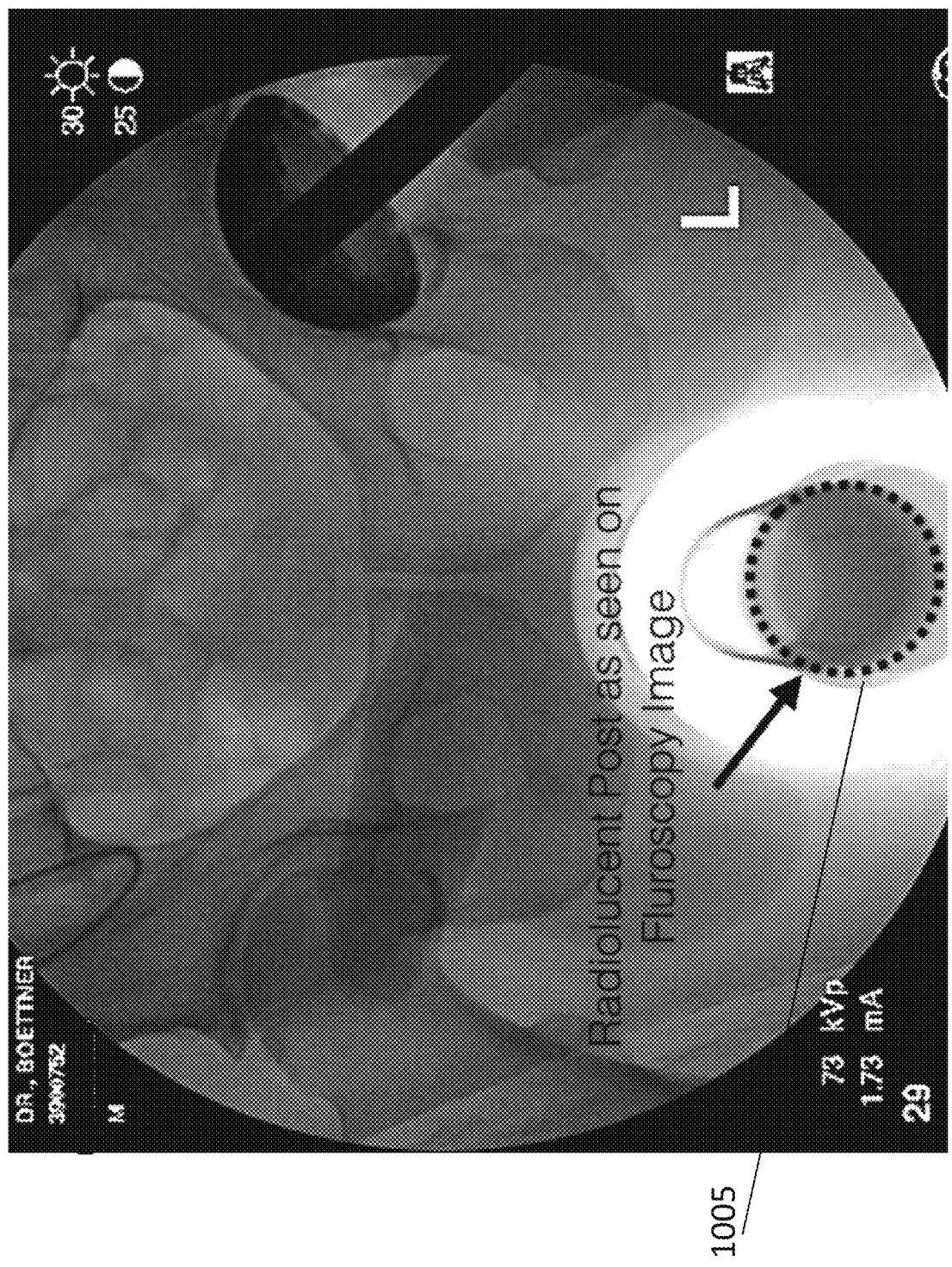
Figure 10D:
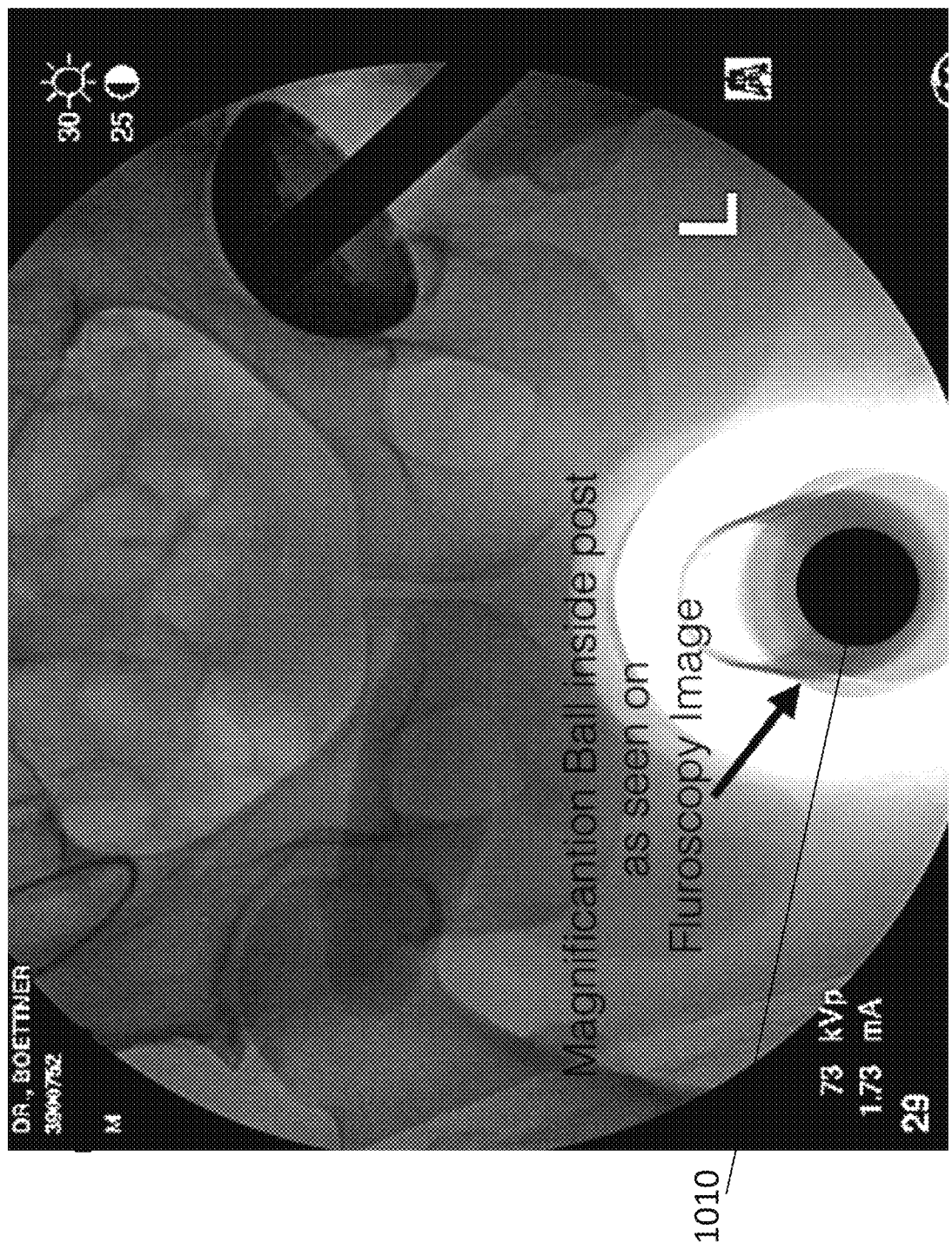
Figure 12:
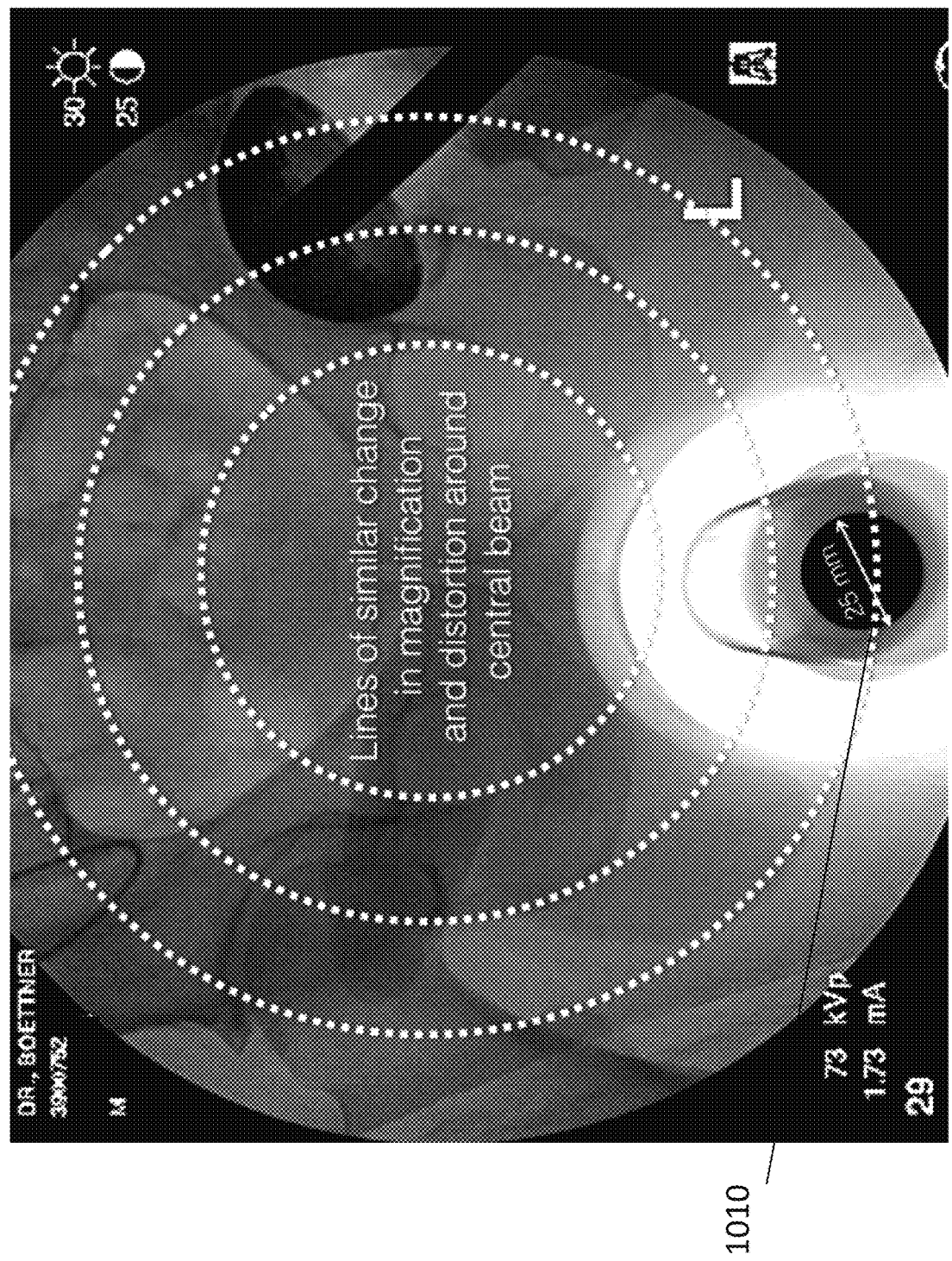
Figure 13:
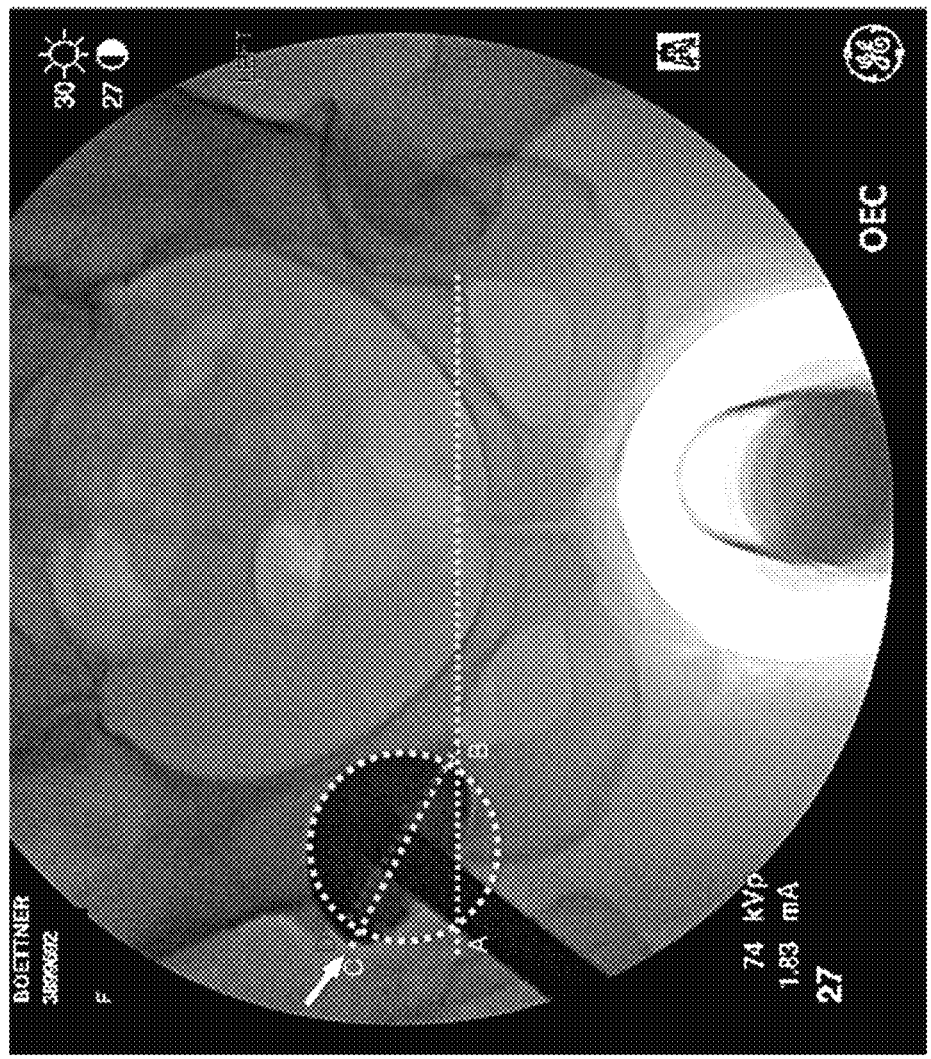
Figure 14:
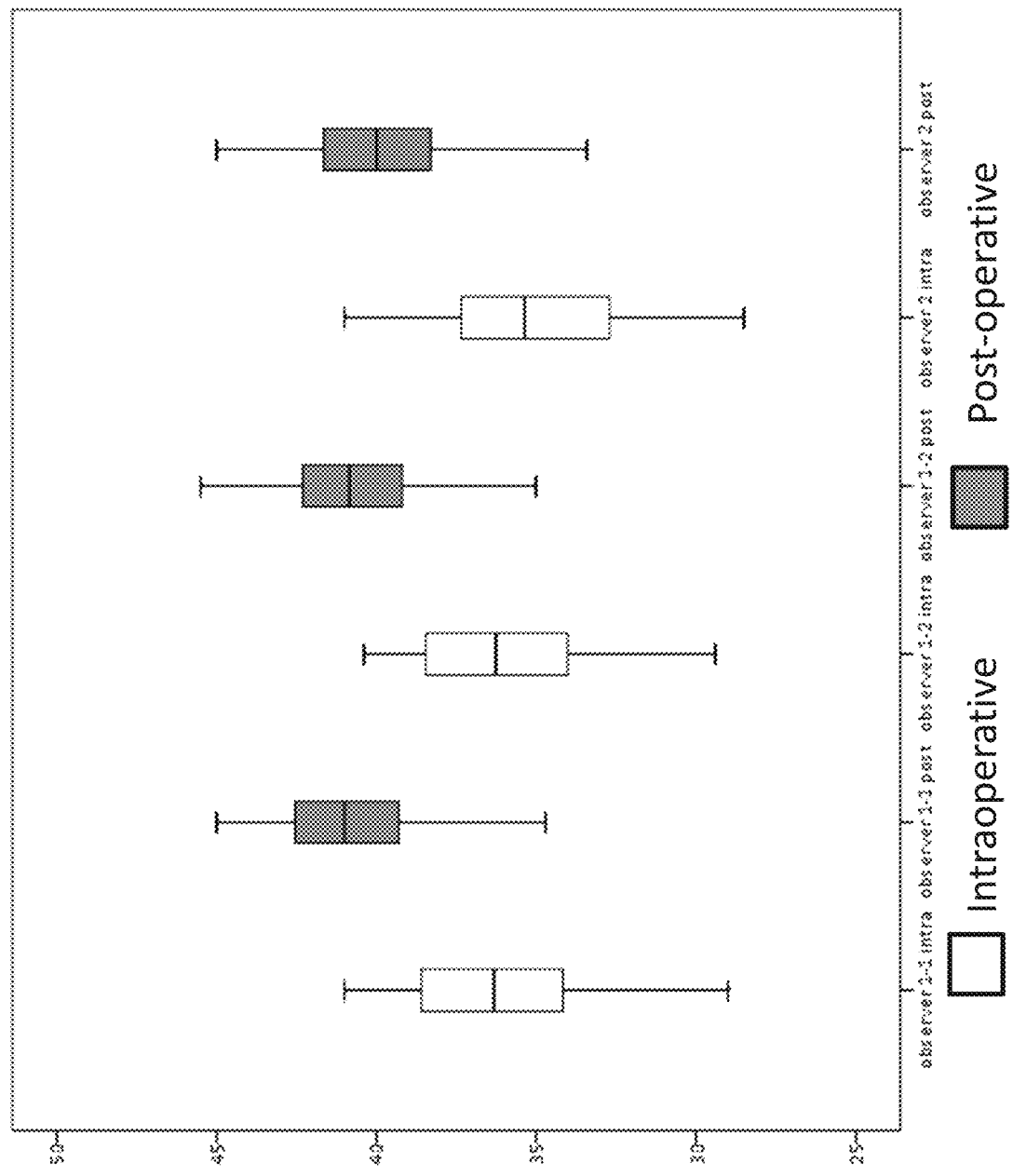
Figure 15:
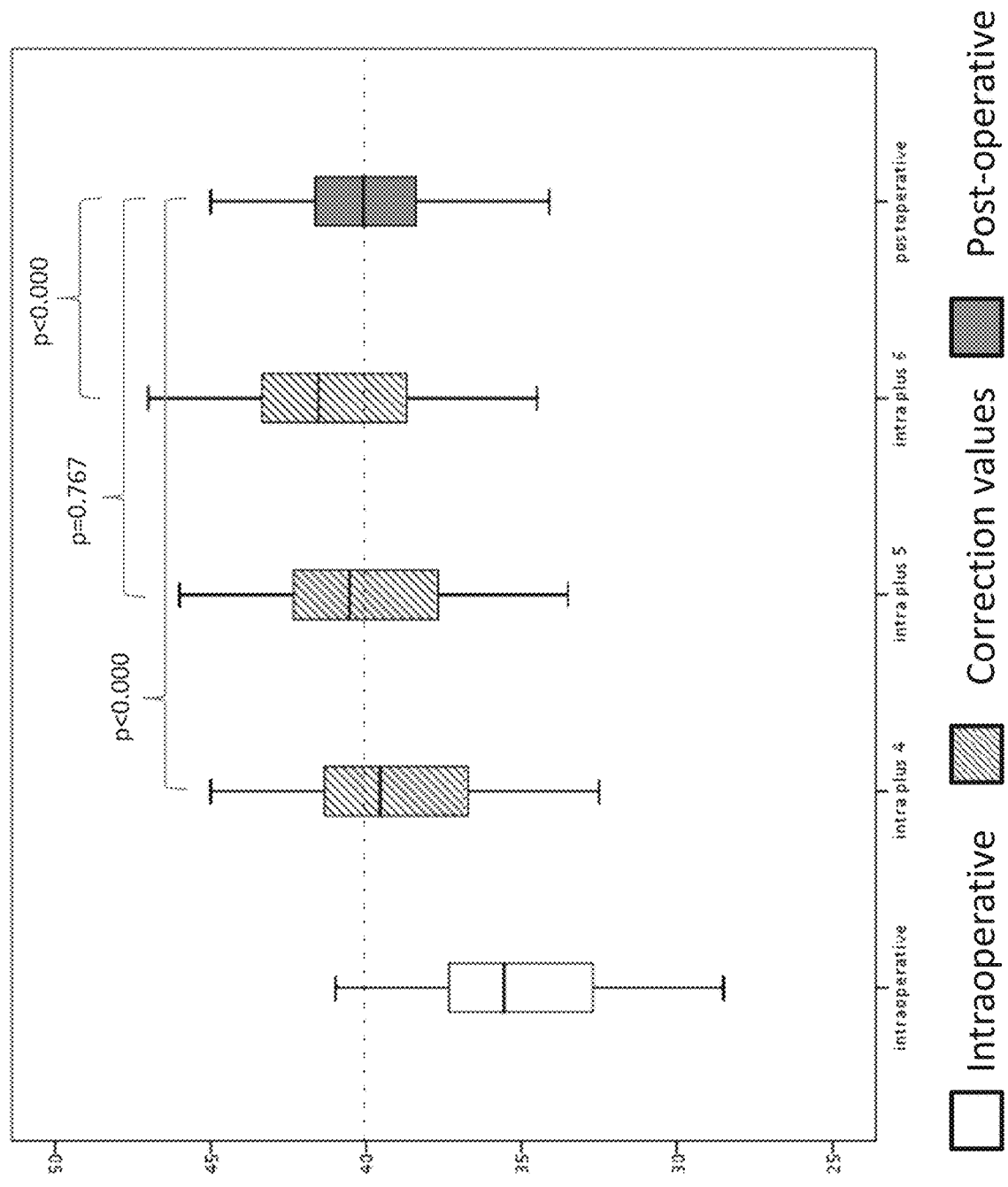
Figure 16:
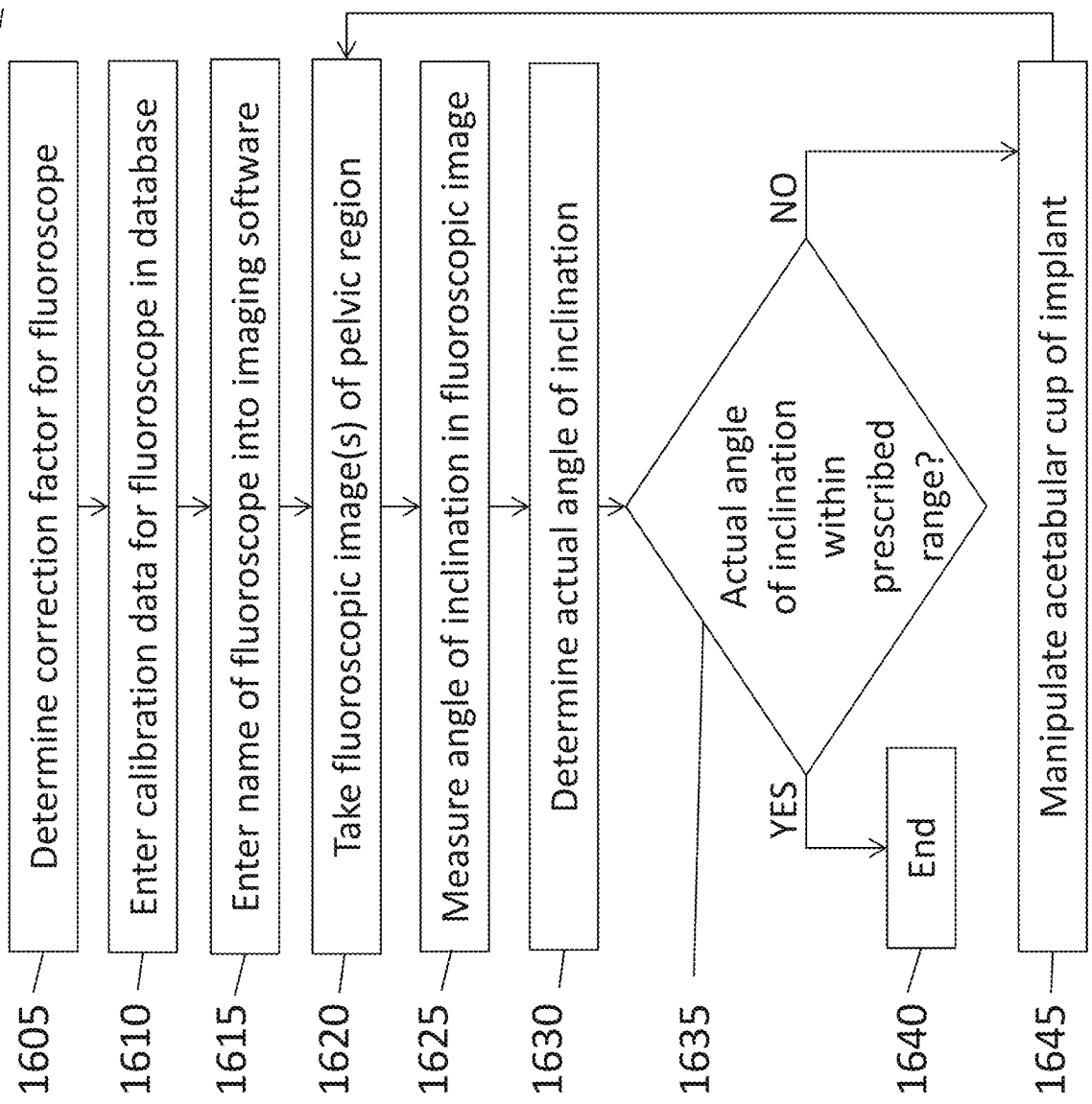
Figure 17:
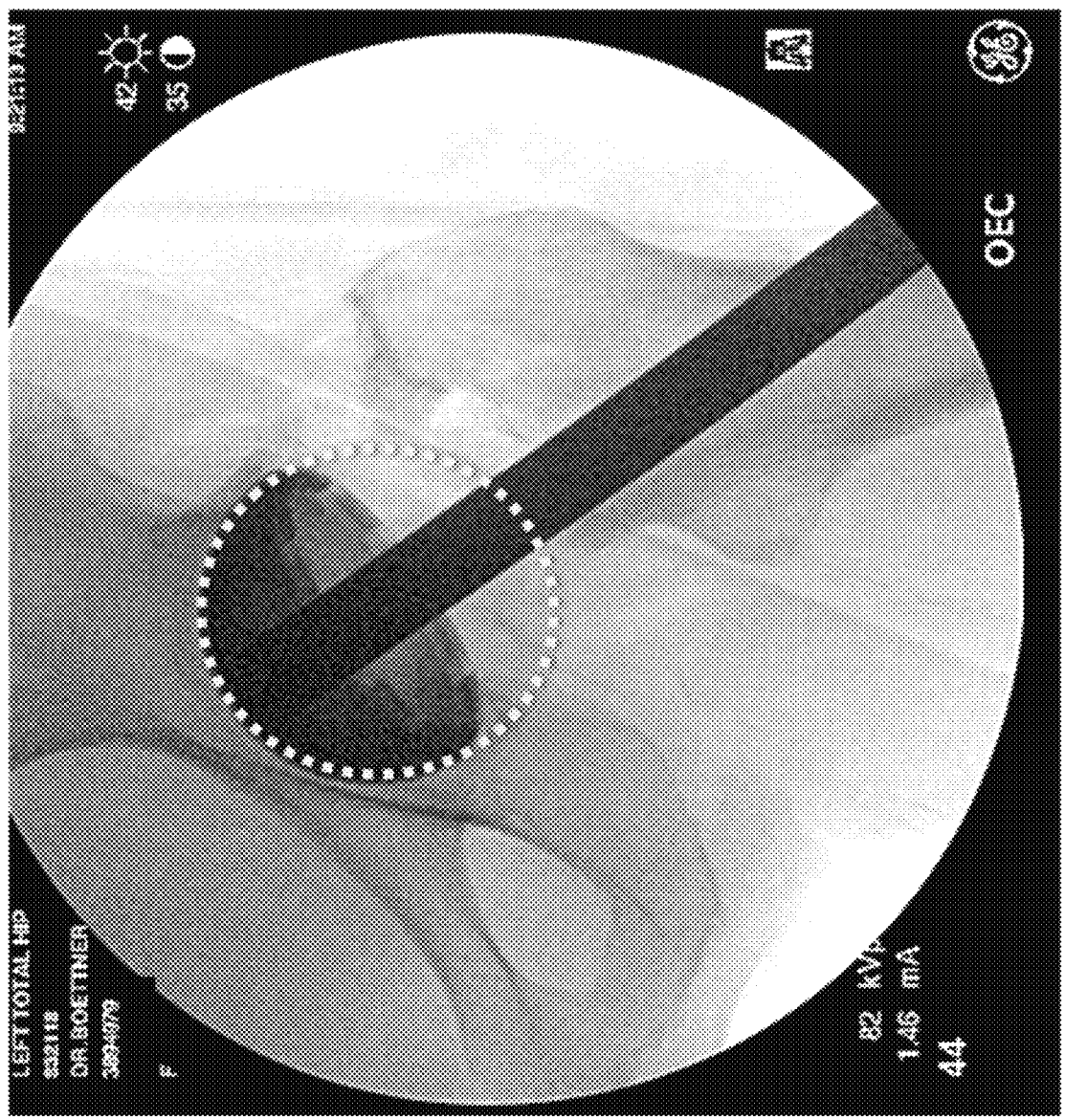
Figure 18:
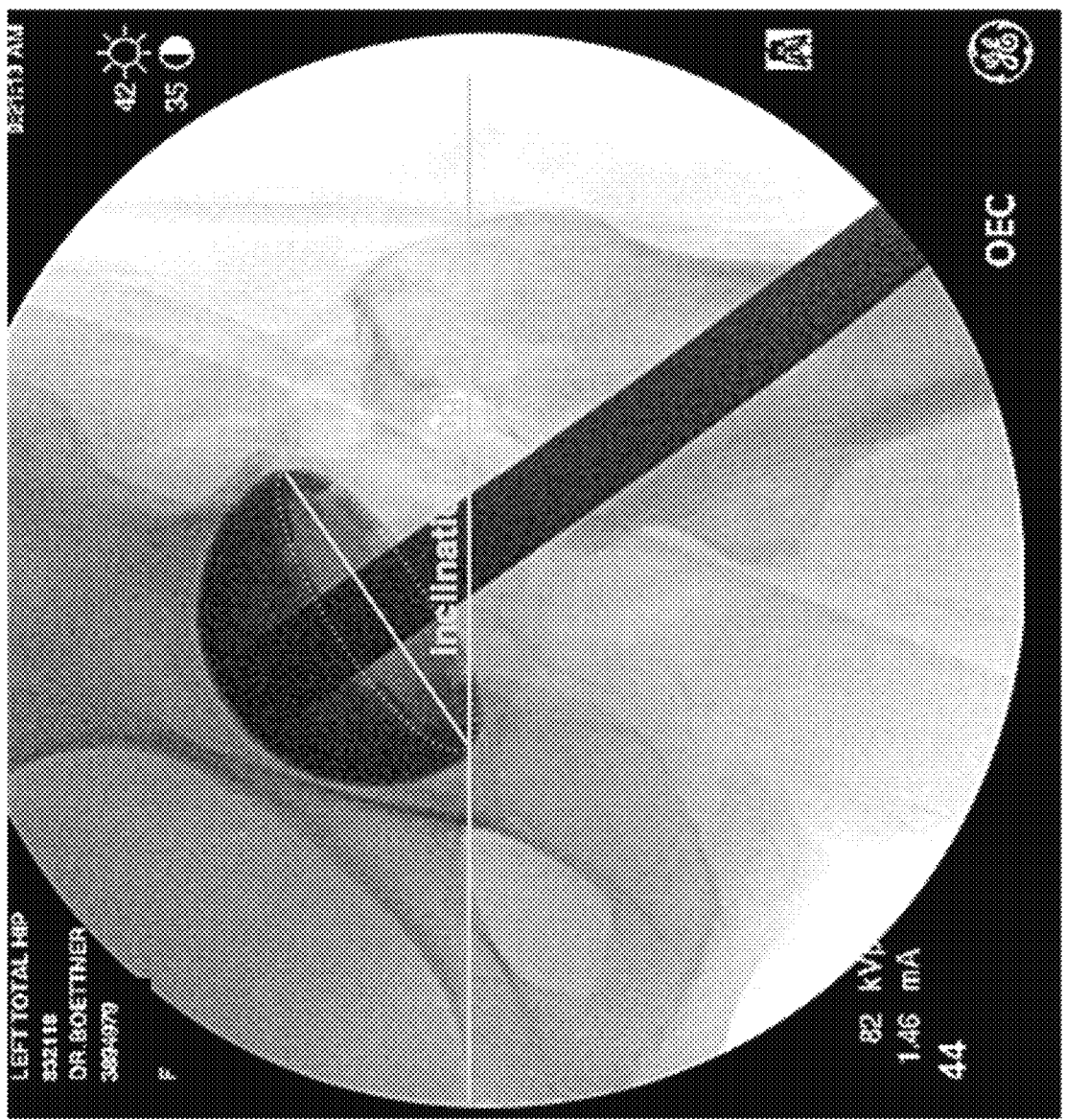
Figure 19:
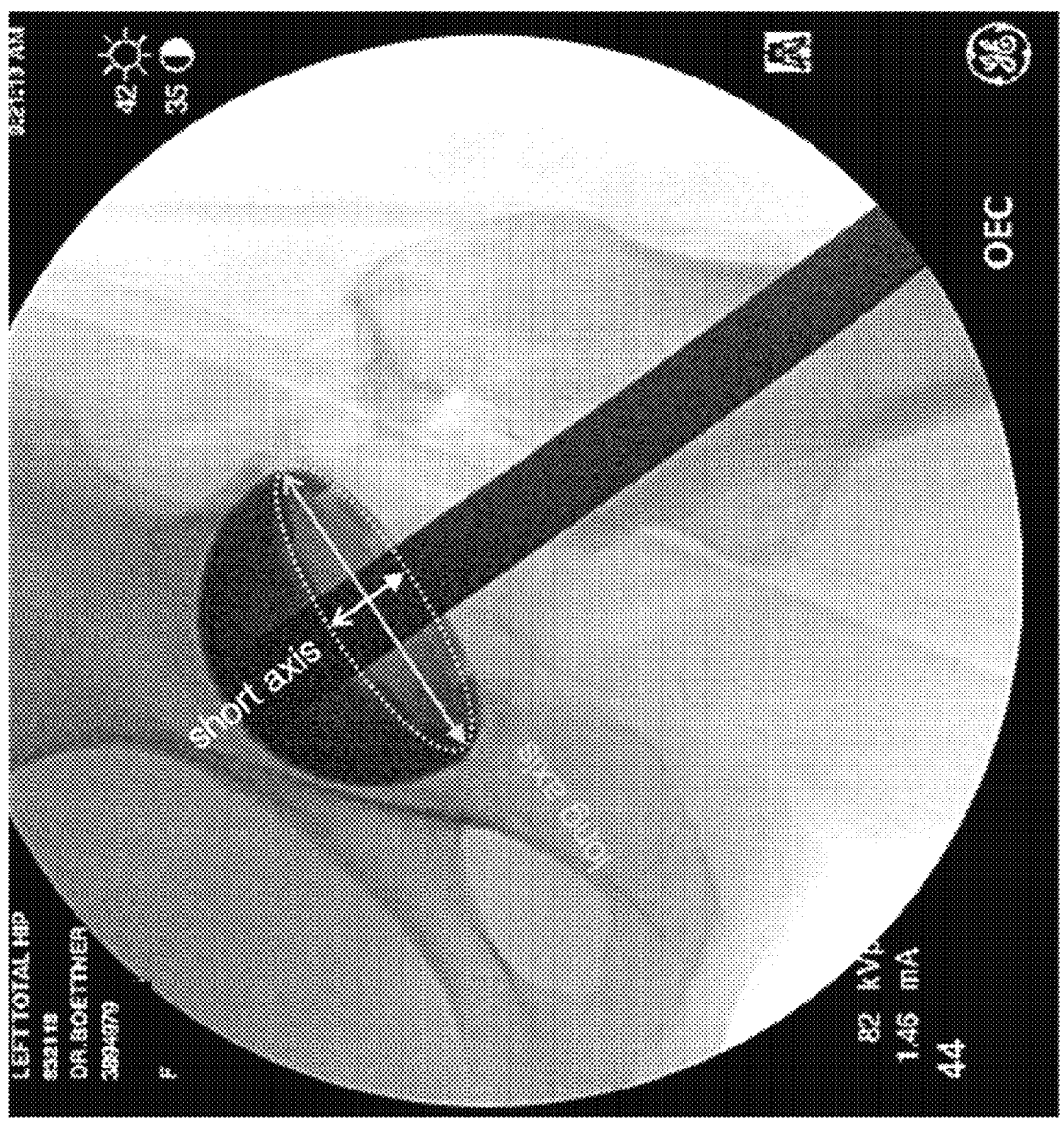
Figure 20:
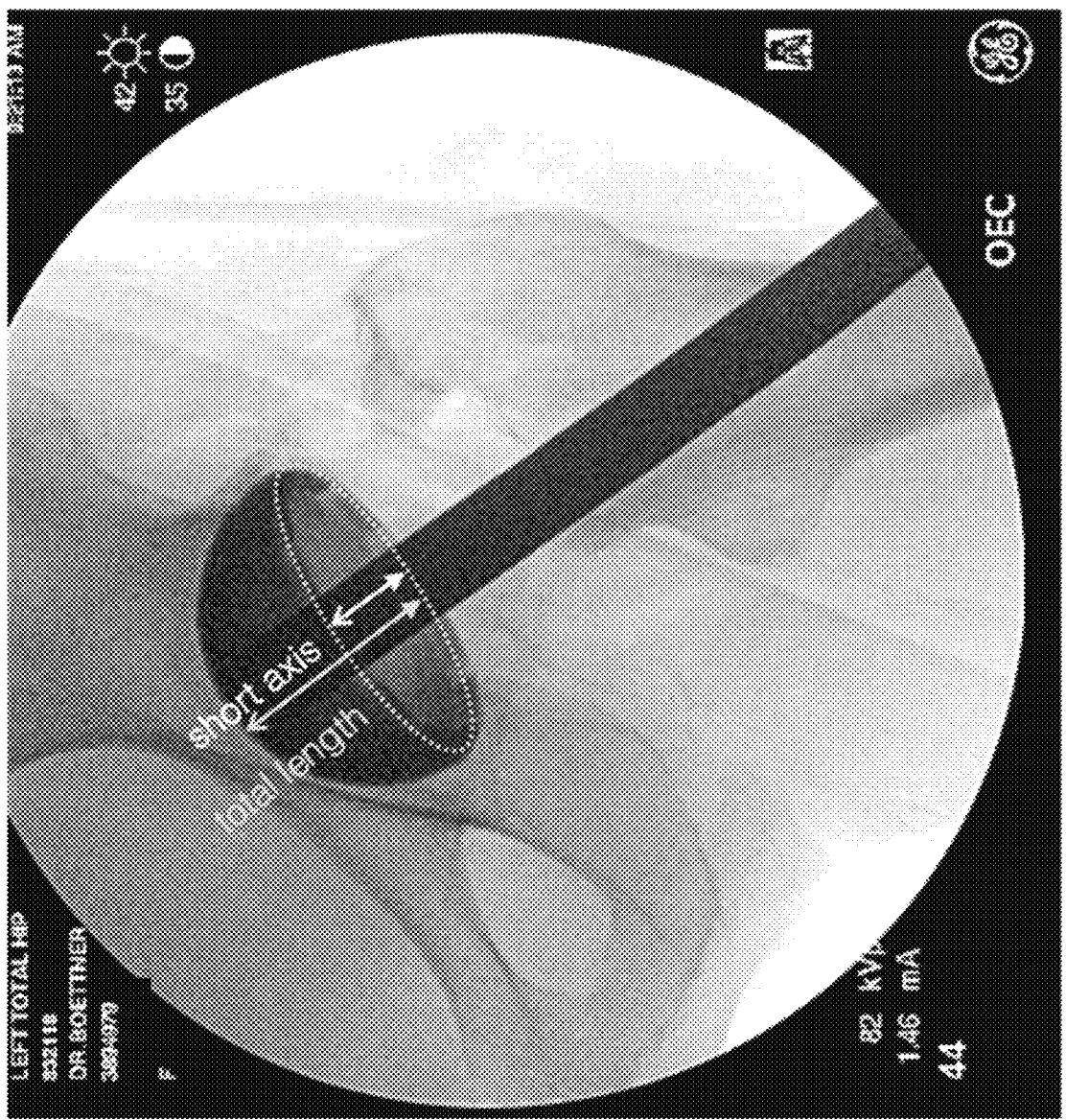
Figure 21:
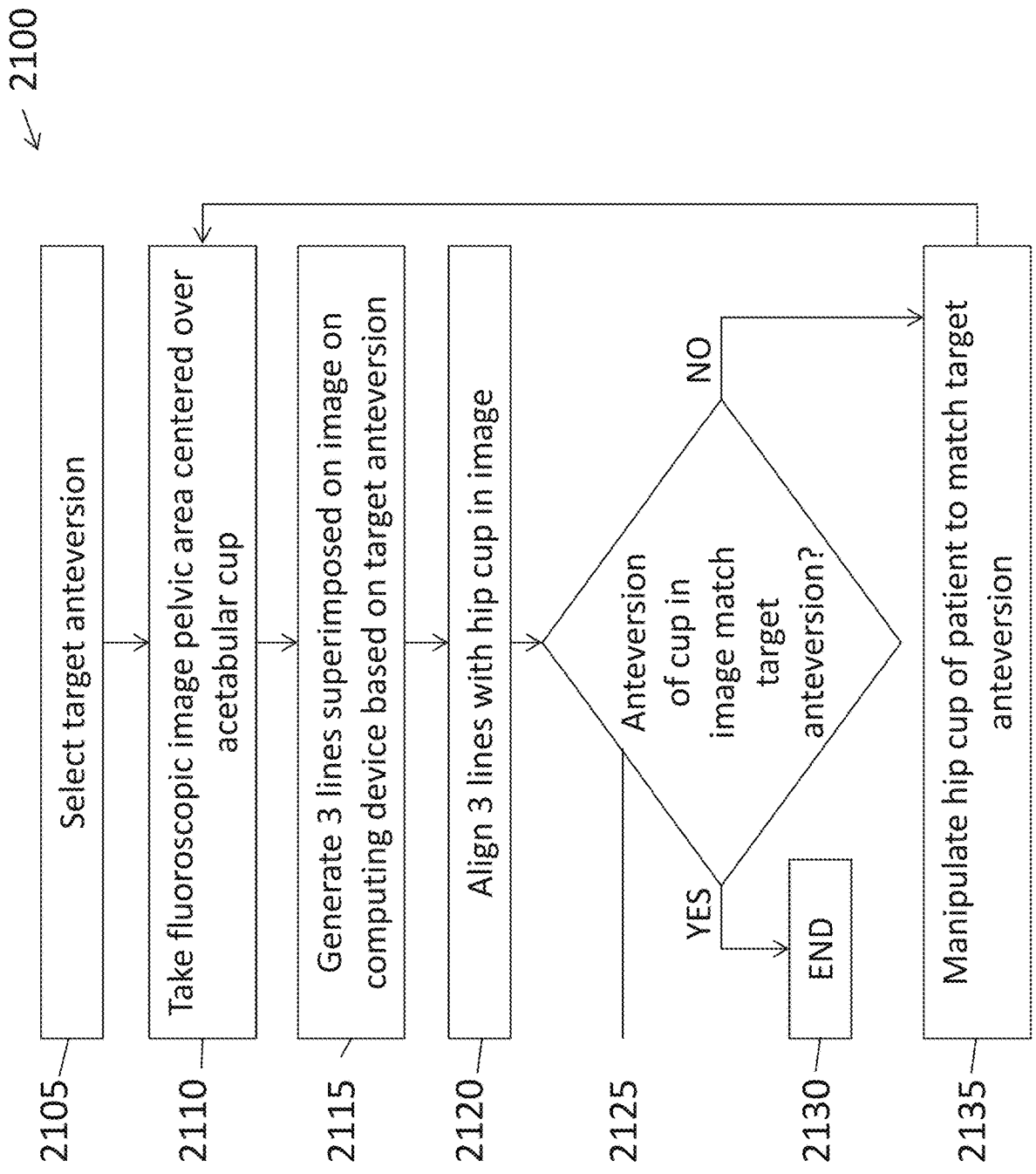
Figure 22:
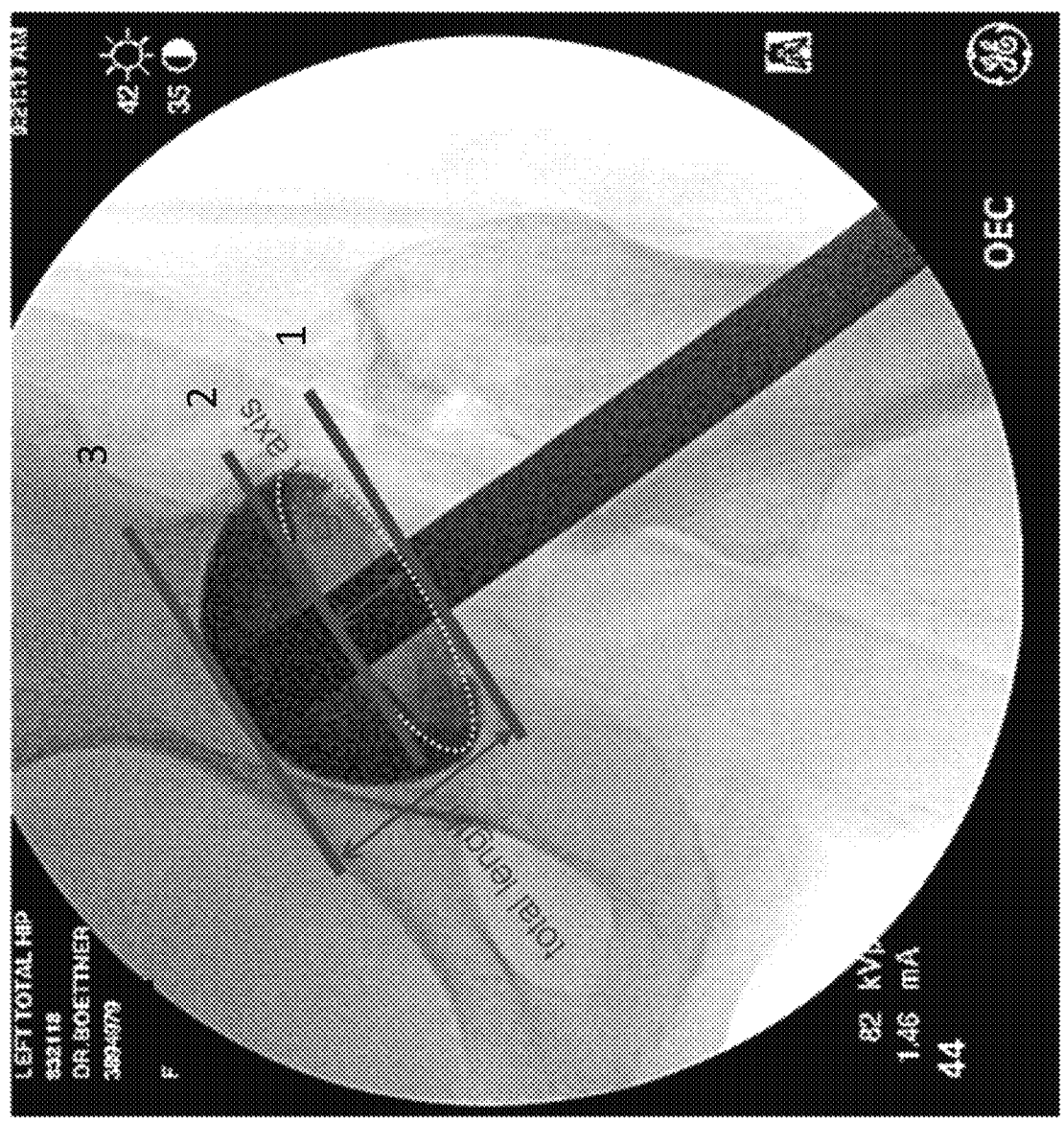
Figure 23:
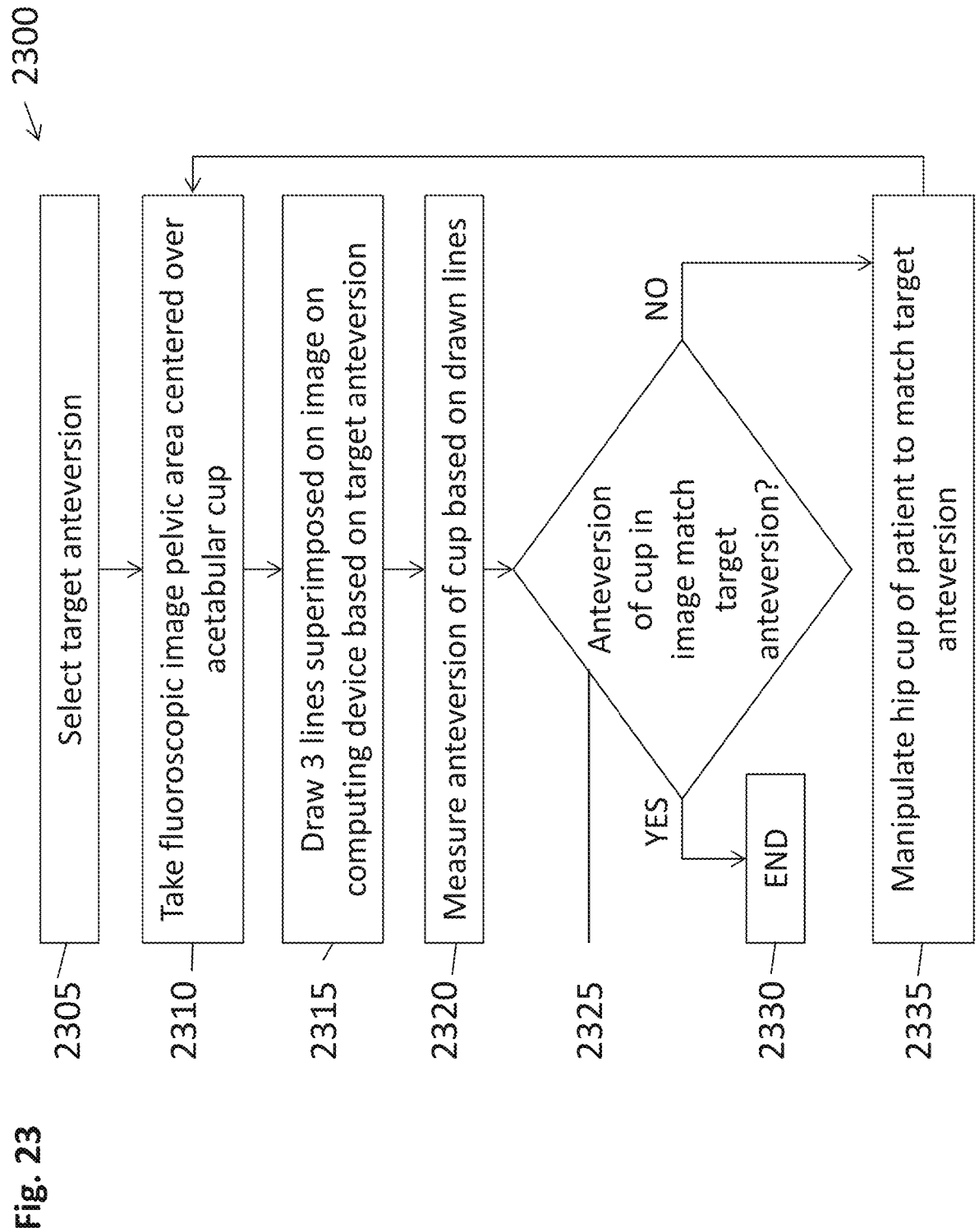
Figure 24:
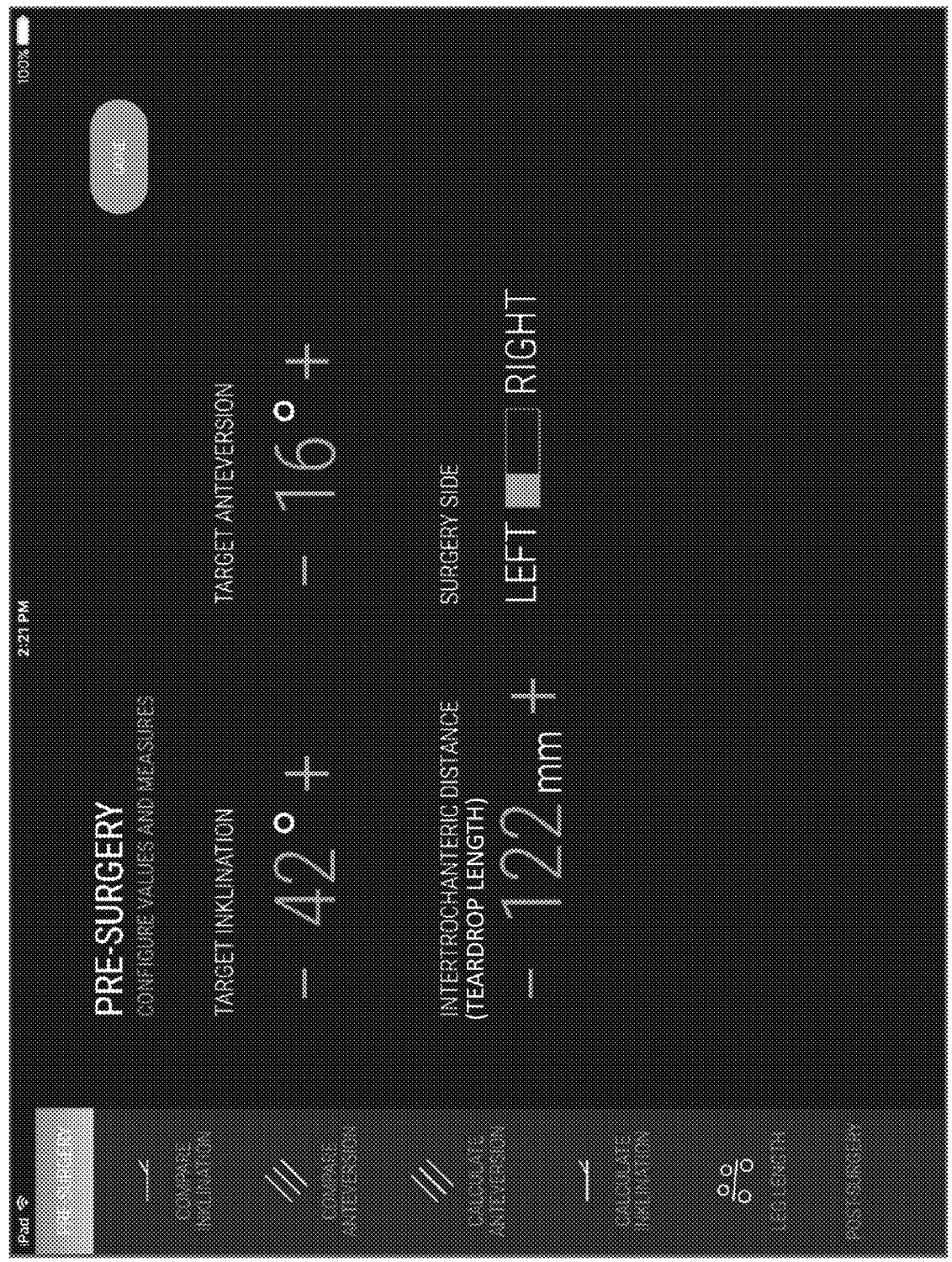
Figure 25:
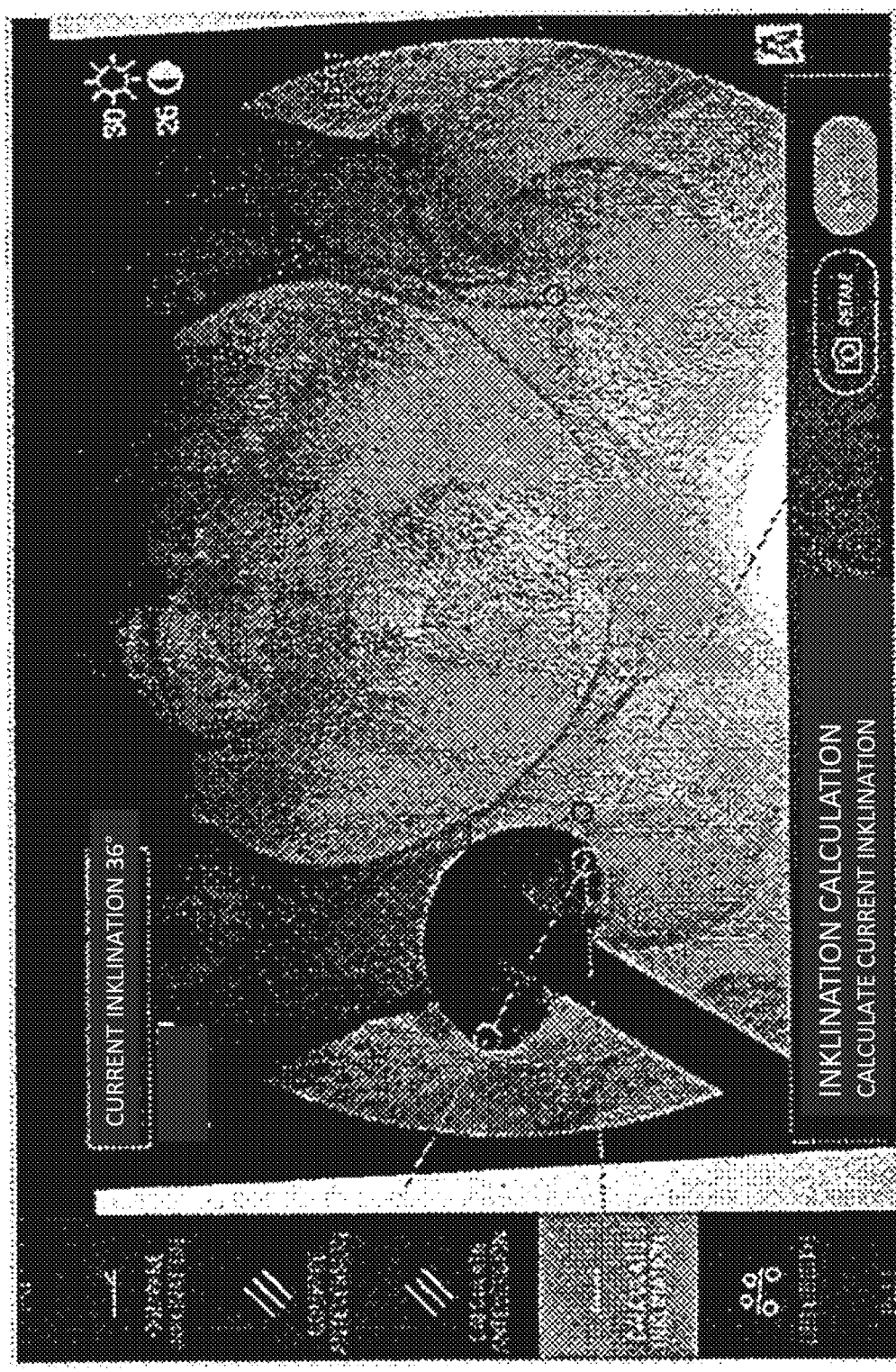
Figure 26:
Figure 27:
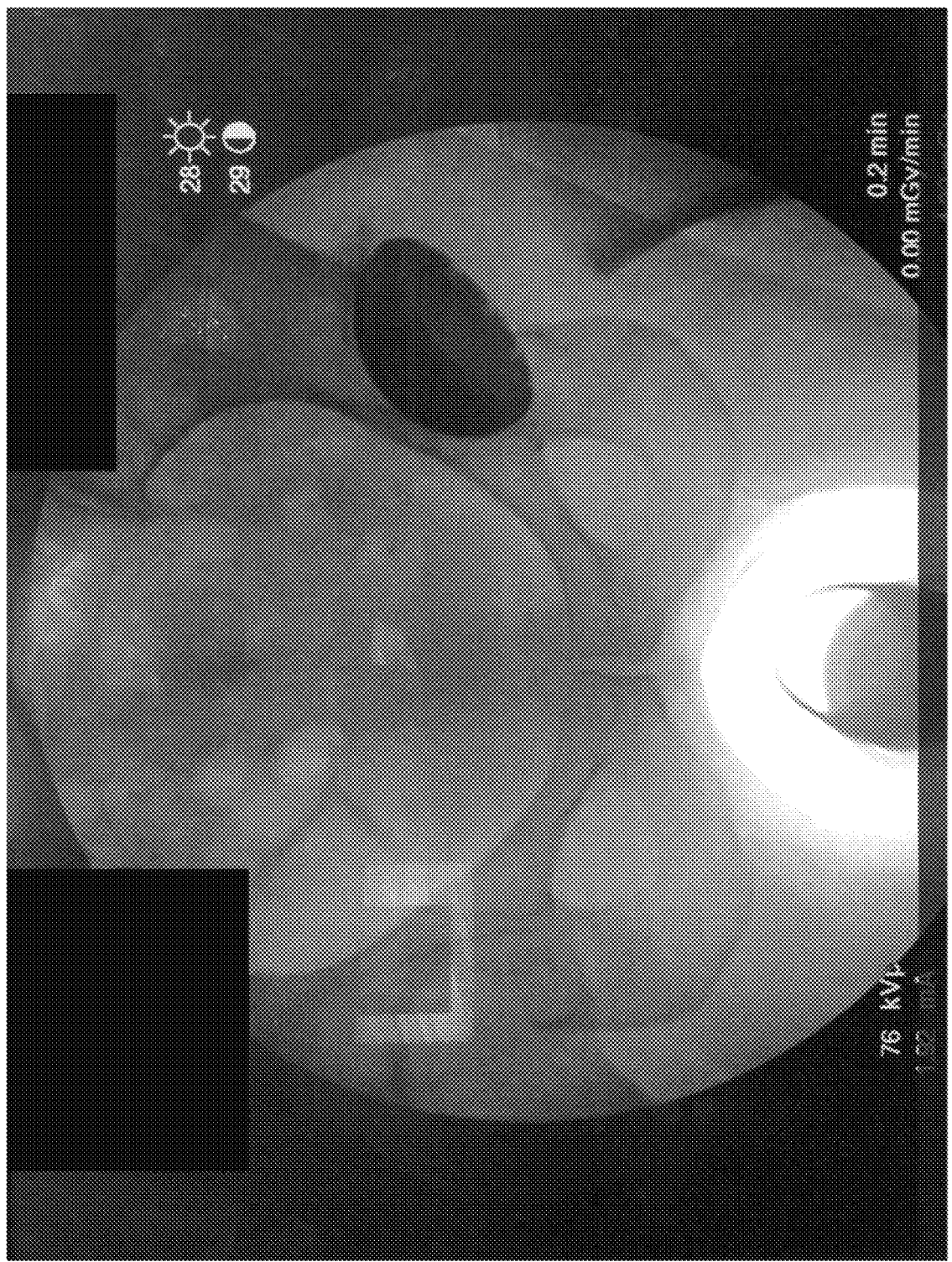
Figure 28:
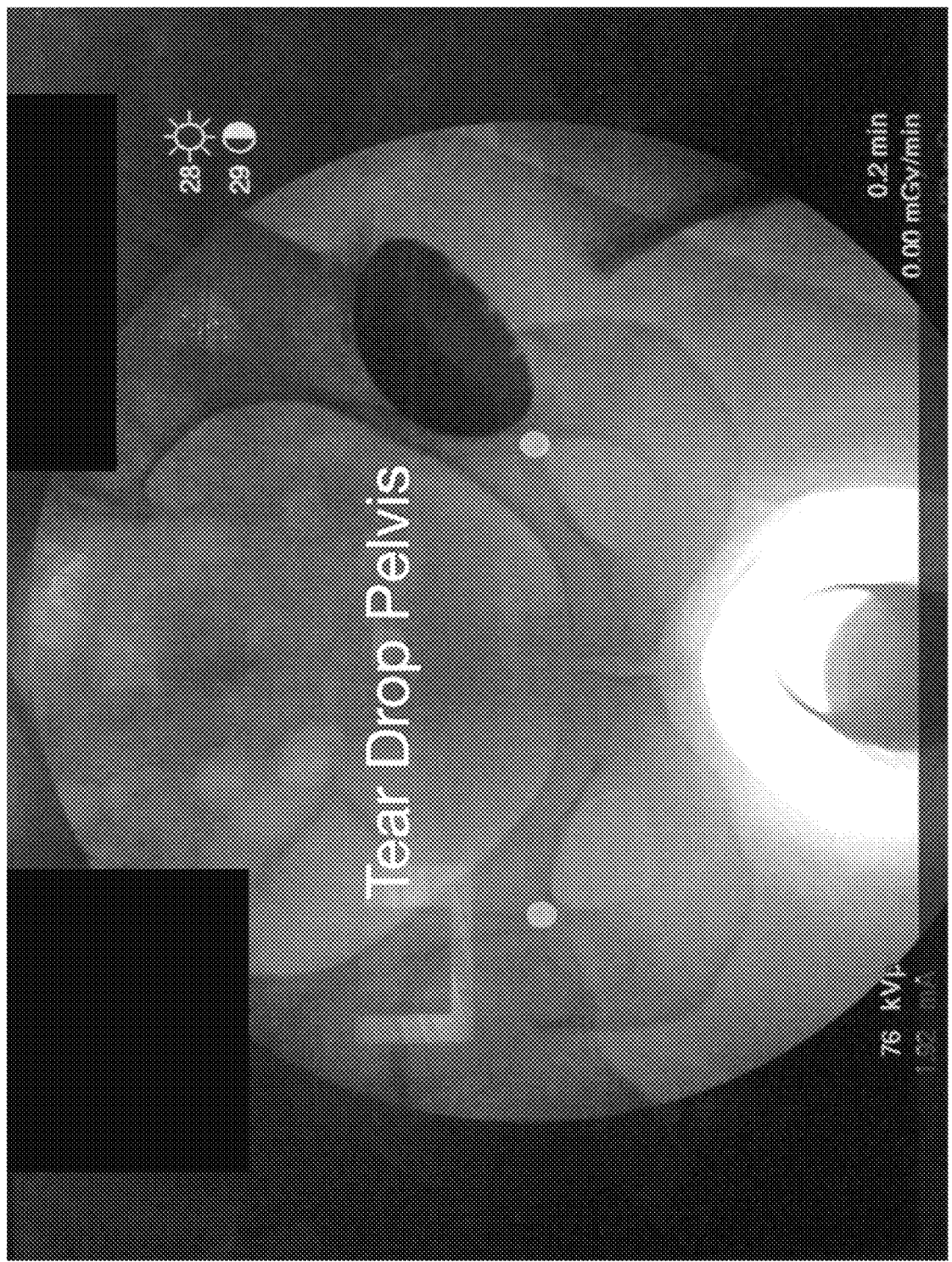

FIG. 4 displays an exemplary anterior posterior (AP) radiographic image of a human pelvis, in which a magnification ball (reference ball) is placed at the same distance to the radiograph as the hip osseous structures in accordance with one or more embodiments;

FIG. 5 shows the graphical user interface of an imaging software program determining the magnification factor of the radiographic image based on the actual size of the magnification ball and the size of the magnification ball as shown in the image in accordance with one or more embodiments;

FIGS. 6A-E show exemplary fluoroscopic images of the hip joint during THA. FIG. 6A shows an image having a reference line through the tear drop and the lesser trochanter, and FIGS. 6B-6E show an image featuring the acetabular component implant and various anatomical measurements in accordance with one or more embodiments;

FIG. 7 shows a fluoroscopic image of the pelvis of a patient including a distorted view of the inserted acetabular cup in accordance with one or more embodiments;

FIG. 8 provides a flow diagram illustrating a routine for correcting the magnification of a fluoroscopic image and determining leg length and offset distances in accordance with one or more embodiments;

FIG. 9 shows a radiographic image of the pelvis showing superimposed reference lines between anatomical landmarks on the pelvic area in accordance with one or more embodiments;

FIGS. 10A-D show exemplary implementations of a post having a magnification ball within it for positioning between the legs of a patient during a THA operation in accordance with one or more embodiments. FIG. 10A shows an image of the post attached to the patient table, while FIG. 10B provides a diagram showing various aspects of the post. FIGS. 10C-D show an exemplary fluoroscopic image of the post having a magnification ball within it;

FIG. 11 provides a flow diagram illustrating a modified routine for correcting the magnification of a fluoroscopic image and determining leg length and offset distances in accordance with one or more embodiments;

FIG. 12 shows a fluoroscopic image of the pelvis showing that the parallax effect is symmetrical around the central beam of the fluoroscopy unit in accordance with one or more embodiments;

FIG. 13 shows the fluoroscopic image of the pelvis as shown in FIG. 7, with superimposed lines for determining the radiographic inclination in accordance with one or more embodiments;

FIG. 14 displays a graph showing the measured radiographic inclination angles for intraoperative and postoperative images for three different measurements in accordance with one or more embodiments;

FIG. 15 displays a graph showing the difference between intraoperative and postoperative radiographic inclination values and the proposed correction values in accordance with one or more embodiments;

FIG. 16 provides a flow diagram illustrating a routine for radiographic inclination correction in accordance with one or more embodiments;

FIG. 17 shows a fluoroscopic image of the acetabular cup in which the central beam of the fluoroscope is centered over the acetabular component in accordance with one or more embodiments;

FIG. 18 shows the fluoroscopic image of FIG. 17 with superimposed lines showing the angle of inclination for the acetabular cup in accordance with one or more embodiments;

FIG. 19 shows the fluoroscopic image of FIG. 17 with superimposed lines showing the short axis and long axis of the acetabular cup in accordance with one or more embodiments;

FIG. 20 shows the fluoroscopic image of FIG. 17 with superimposed lines showing the short axis and total length of the acetabular cup in accordance with one or more embodiments;

FIG. 21 provides a flow diagram illustrating a routine for measuring the degree of anteversion of the acetabular cup in accordance with one or more embodiments;

FIG. 22 shows an exemplary fluoroscopic image of the acetabular cup featuring three superimposed lines for measuring the degree of anteversion in accordance with one or more embodiments;

FIG. 23 provides a flow diagram illustrating an alternative routine for measuring the degree of anteversion of the acetabular cup in accordance with one or more embodiments;

FIG. 24 shows an exemplary screen of a graphical user interface of imaging software in which the screen shows pre-surgery options for entering the target inclination, anteversion, and teardrop length of the patient in accordance with one or more embodiments;

FIG. 25 shows an exemplary screen of the graphical user interface of the imaging software during surgery in which lines are superimposed over the acetabular cup in the image and the angle of inclination for the acetabular cup is calculated in accordance with one or more embodiments;

FIG. 26 shows an exemplary screen of the graphical user interface of the imaging software during surgery in which three lines are superimposed over the acetabular cup in the image and the degree of anteversion for the acetabular cup is calculated in accordance with one or more embodiments;

FIGS. 27-34 illustrate a series of screens of a graphical user interface and representing a technique regarding modification of a radiographic image, including prior to measuring a distance or angle.

DETAILED DESCRIPTION OF CERTAIN EMBODIMENTS

By way of overview and introduction, various fluoroscopy-based methods and systems are described herein for making accurate measurements of a patient during a surgical procedure. More specifically, the present application provides for making accurate measurements of the hip area and hip implant during THA. While the present application focuses on fluoroscopy-based methods and systems for measuring portions of the pelvis and hip area accurately for patients undergoing THA, it should be understood that the present methods and systems can also be applied to fluoroscopic-based measurements for subjects or patients undergoing other types of procedures.

Acetabular Cup of Hip Implant

Figure 1:
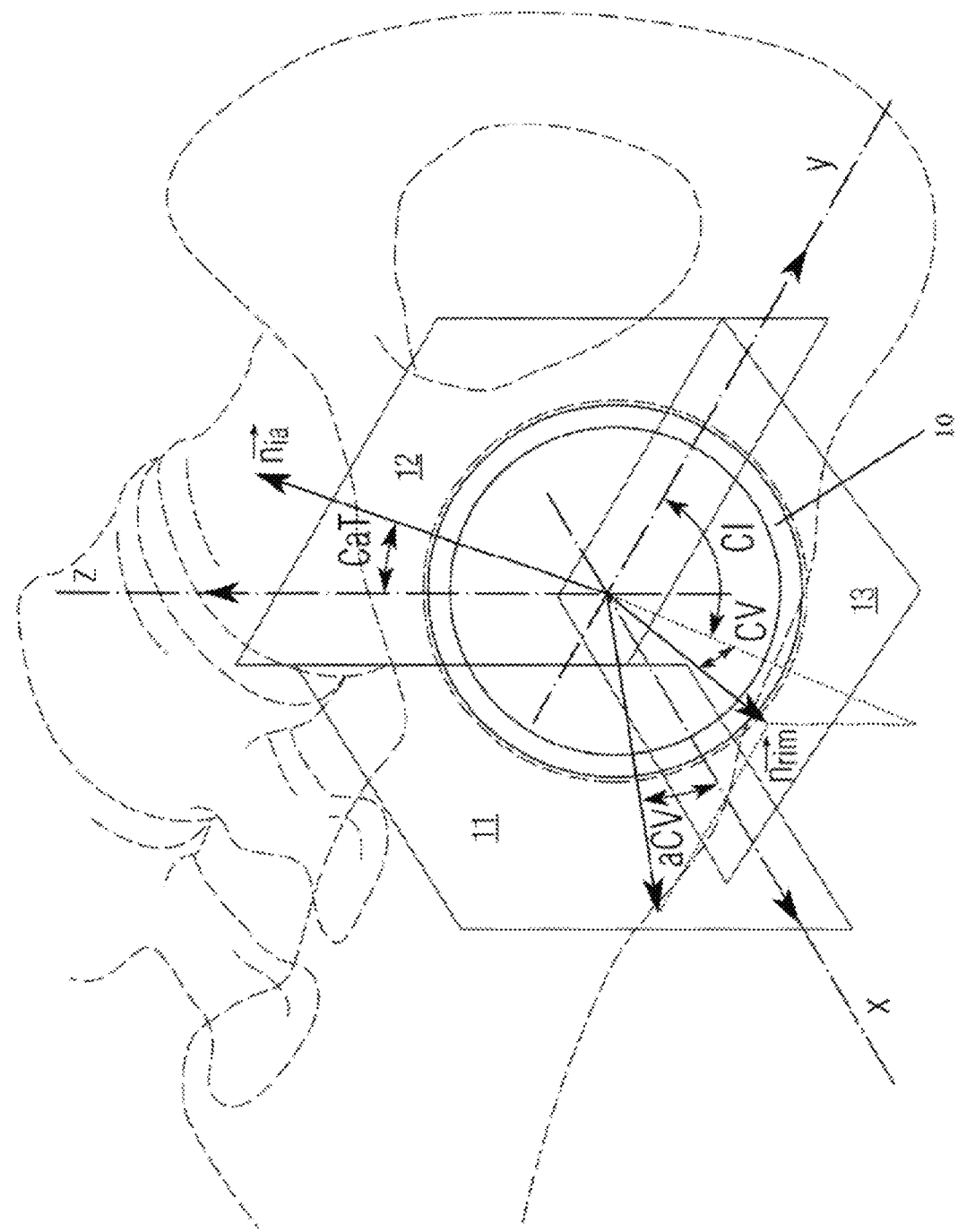

Descriptions herein regarding the position (orientation) of an acetabular cup of a hip implant include CV and CI, which refer to Murray's radiographic definition of anteversion and inclination, respectively, and as shown in FIG. 1. In FIG. 1, $\vec{n}_{rim}$ is the vector normal to the plane of the rim of the acetabular cup 10 and is defined by the inclination angle CI and the anteversion angle CV. aCV is the angle between the projection of $\vec{n}_{rim}$ on a transverse plane 11 and a coronal plane 13. $\vec{n}_{ia}$ is the vector normal to a plane of the image amplifier of the C-arm fluoroscope (e.g., a transverse plane at the bottom end of the image amplifier). CaT is the tilt angle that is to be applied to the C-arm fluoroscope to make the plane of the image amplifier perpendicular to the plane of the rim of the cup, and corresponds to the angle between $\vec{n}_{ia}$ and the z-axis. The sagittal plane is shown at 12. In one embodiment, when the plane of the image amplifier is made perpendicular to the plane of the rim of the cup, a center longitudinal axis (along which the beam travels) of the image amplifier is parallel (or coplanar) to the plane of the rim of the cup (the center longitudinal axis can be coaxial with the vector $\vec{n}_{ia}$ which can be coplanar to the rim's plane).

CV is thus defined as the angle between the vector perpendicular to the plane of the rim of the cup and the coronal plane 13. CI is thus defined as the angle between the sagittal plane 12 and the projection of the vector perpendicular to the plane of the rim of the cup on the coronal plane 13. Murray's definition of the anatomic anteversion angle (aCV) corresponds to the angle between the coronal plane 13 and the projection of the vector perpendicular to the plane of the rim of the cup 10 on the transverse plane 11. As CV and aCV are different projections of the same vector, they are dependent and bound by the relation:

$$CV = \tan^{-1}[\tan(aCV) \sin(CI)]$$

Figure 2:
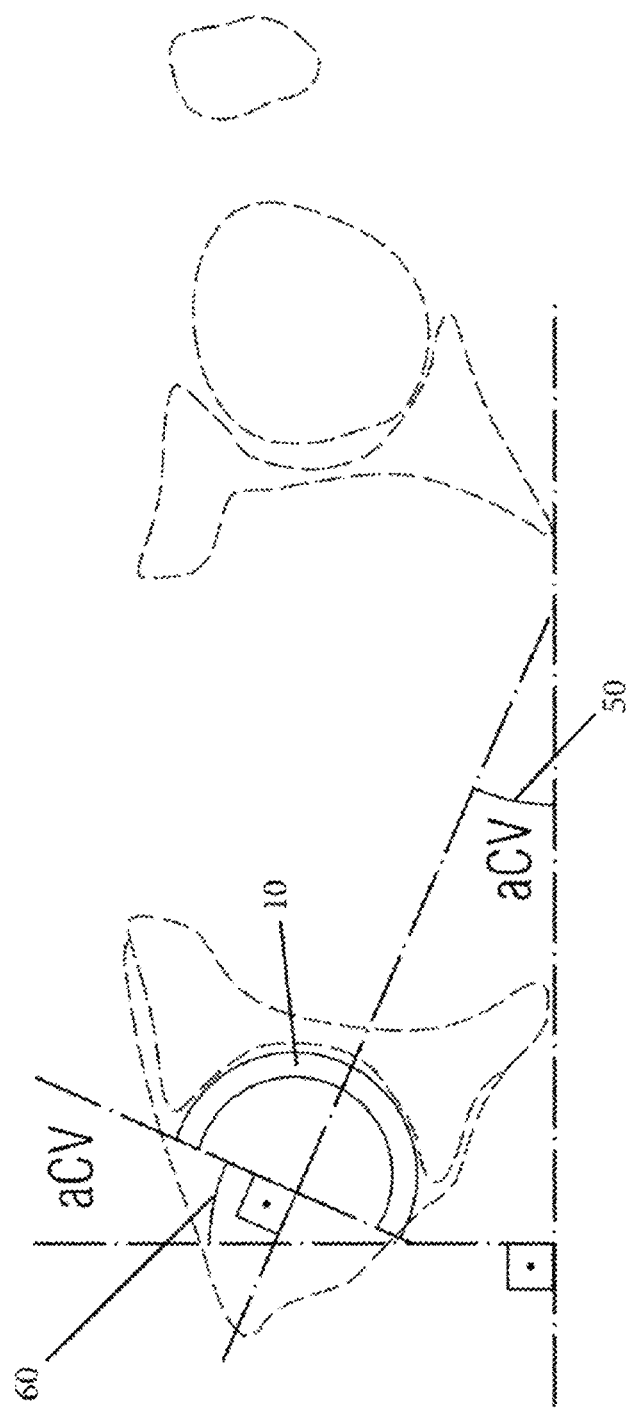
FIG. 2 illustrates two equivalent aCV measuring techniques on CT-scan images in which: the reference line of the coronal plane passes through the ischial spines; aCV is the angle between the coronal plane and the line perpendicular to plane of the rim of the cup; and aCV is the angle between a line parallel to the sagittal plane and a line parallel to plane of the rim of the cup.

This relation proves useful to compare experimental and control (CT-scan) cup anteversion assessment methods because the evaluation of CV on CT-scan images is challenging whereas the measurement aCV is straightforward as depicted in FIG. 2. FIG. 2 presents two equivalent aCV measuring techniques on CT-scan images. The reference line of the coronal plane passes through the ischial spines. aCV is the angle between the coronal plane and the line perpendicular to the plane of the rim cup (as depicted at 50). aCV is the angle between a line parallel to the sagittal plane and a line parallel to the plane of the rim of the cup (as depicted at 60).

Fluoroscope-Based Systems of Measurement

As mentioned herein, the present application is directed to improved systems and methods for measuring aspects of the hip and pelvis area during a THA operation using radiography and intraoperative fluoroscopy. These methods can include a number of steps that are each described in detail herein and in which the patient is in a supine position.

Figure 3A:
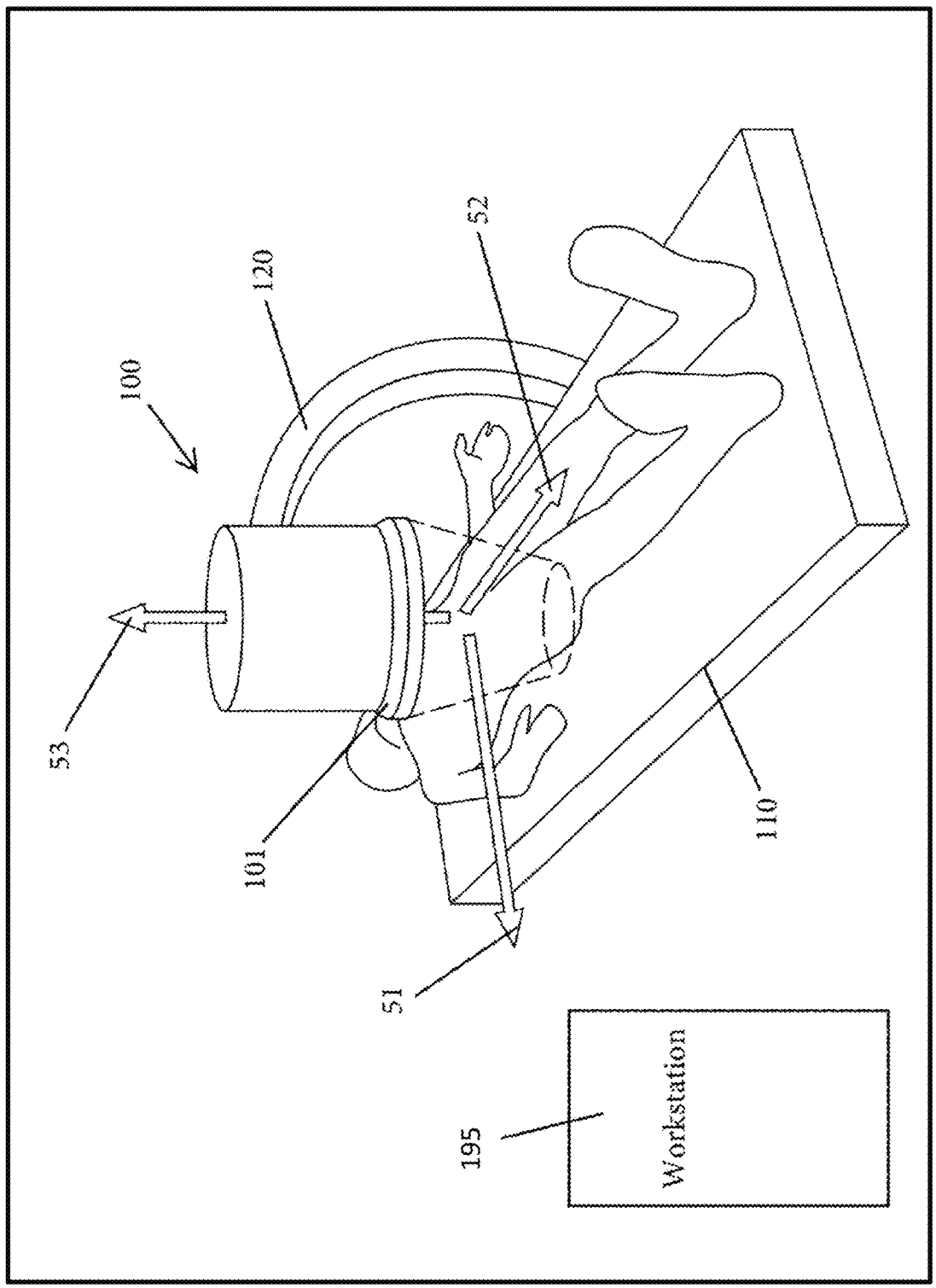
FIG. 3A is a perspective view of a fluoroscopic system positioned perpendicular to a longitudinal axis of an operating table in accordance with one or more embodiments.

FIG. 3A illustrates an exemplary imaging system (or "fluoroscopy system") 100 that comprises an x-ray imaging system in the form of a fluoroscope. The fluoroscopy system 100 includes an x-ray image intensifier (image amplifier) 101 that is configured to convert x-rays into visible light at higher intensity than do mere fluorescent screens. The image intensifier 101 allows low-intensity x-rays to be converted to a conveniently bright visible light output. The fluoroscopy system 100 traditionally contains a low absorbency/scatter input window, typically aluminum, input fluorescent screen, photocathode, electron optics, output fluorescent screen and output window. These parts are all typically mounted in a high vacuum environment within glass or more recently, within metal/ceramic. By its intensifying effect, the fluoroscopy system 100 allows the viewer to more easily see the structure of the object being imaged than fluorescent screens alone, whose images are dim.

The exemplary imaging system 100 shown in FIG. 3A is configured as a C-arm based system, which is commonly used for studies requiring the maximum positional flexibility. The fluoroscopy system 100 has a patient support (e.g., a table) 110 which allows the patient to lie in a supine position. The fluoroscopy system 100 can also include a C-arm unit 120 (which has a "C" shape) that is positioned relative to and is movable relative to the table 110. The C-arm 120 works in conjunction with patient table 110 that is specifically designed for X-ray imaging. The table 110 allows for free positioning of the C-arm 120 around the patient. The table 110 is also X-ray translucent so as to not interfere with imaging. The system 100 can further include a workstation 195 which can be detached and remote from the C-arm 120.

Figure 3B:
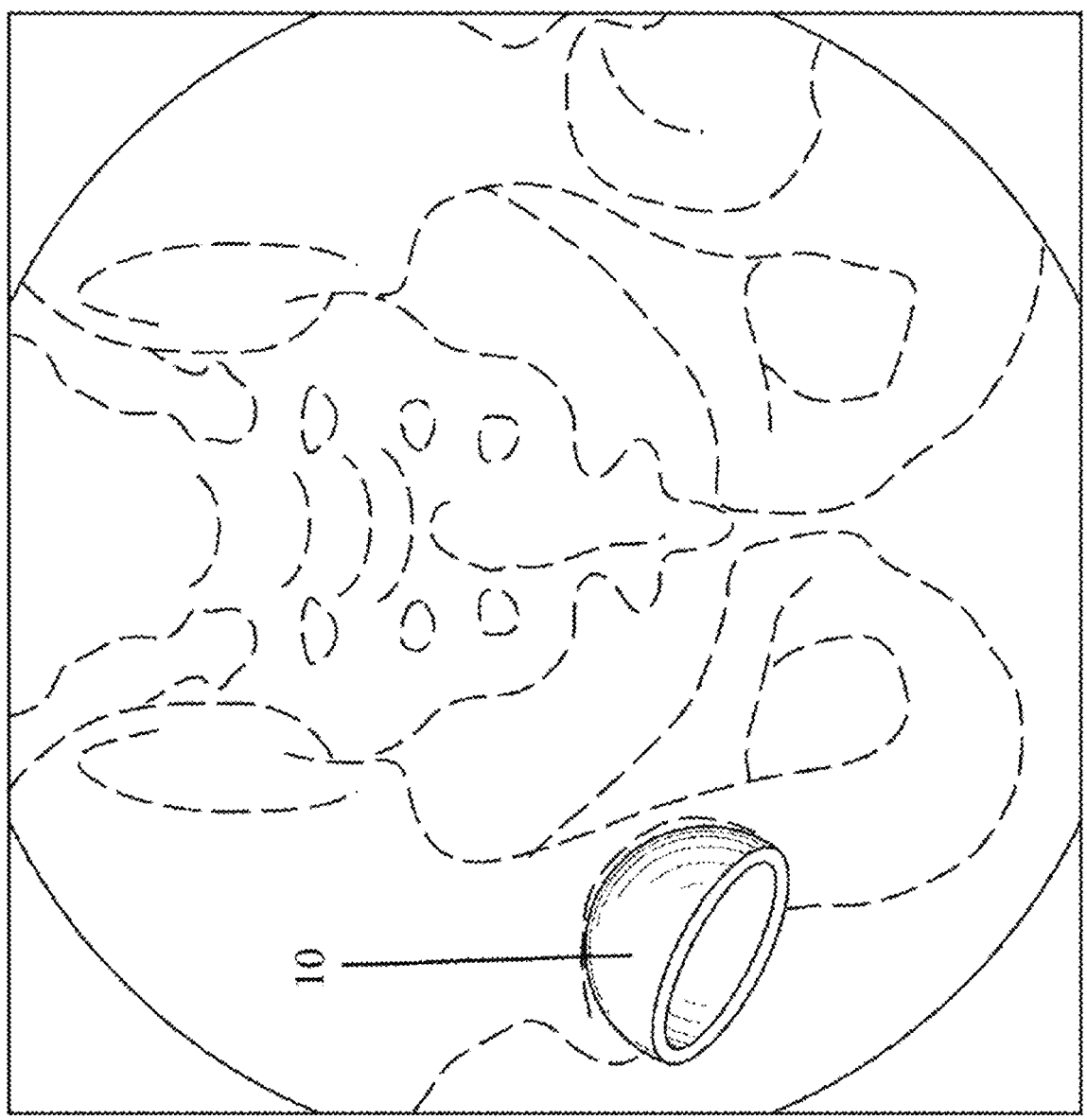
FIG. 3B is an anteroposterior (AP) image (radiograph) of the pelvis showing a particular view in which the acetabular cup rim appears elliptical.

In FIG. 3A, the fluoroscopy system (C-arm 120) is positioned perpendicular to the longitudinal axis of the operating table 110. The x-axis of the three-dimensional frame is perpendicular to the sagittal plane (FIG. 3A, arrow 51), the y-axis parallel to the cranio-caudal axis of the body of the patient (FIG. 3A, arrow 52) and the z-axis perpendicular to the coronal plane (FIG. 3A, arrow 53). In FIG. 3B, an anteroposterior view of the pelvis is shown and it will be appreciated that the rim of the acetabular cup 10 can appear elliptical in such view with the patient lying in the supine position on the table (110).

Figure 3C:
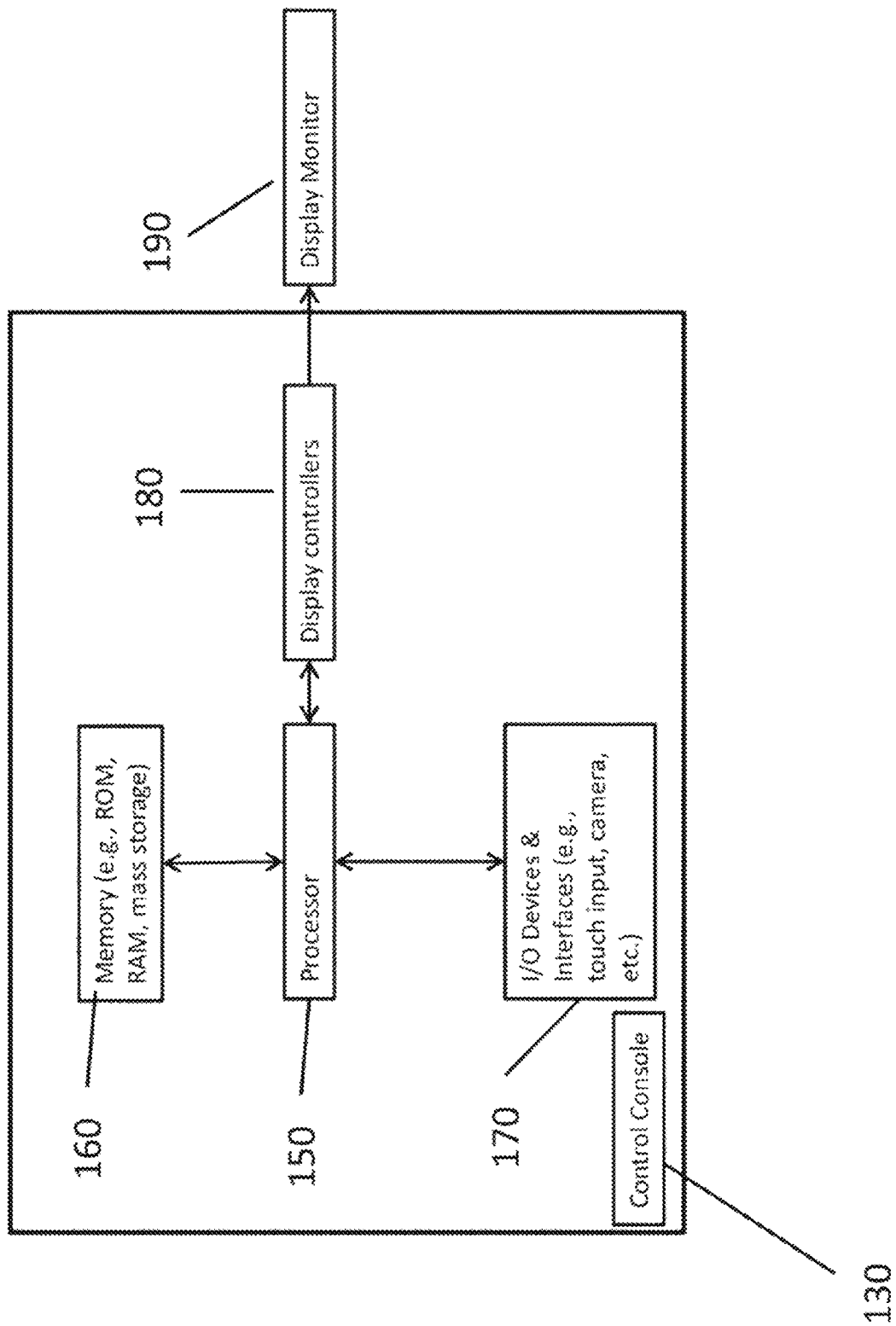
FIG. 3C is a block diagram illustrating an exemplary hardware arrangement included with the fluoroscopic system of FIG. 3A, in accordance with one or more embodiments.

FIG. 3C illustrates an exemplary hardware arrangement included with the fluoroscopic system of FIG. 3A. As shown in FIG. 3C, the fluoroscopy system 100 can also include other devices and more particularly, an imaging device/control console 130, one or more display controllers 180, one or more display monitors 190, and image processing and recording devices. Imaging device/control console 130 can perform many different movements of the C-arm 120. For example, the C-arm 120 has the following range of movements: raise, lower, extend, rotate and tilt. In one or more embodiments, the fluoroscopy system 100 employs hardware and software that provide functionality to measure intraoperative acetabular cup anteversion during total hip arthroplasty. Computer programs (e.g., imaging software) and other executable instructions and data can be stored on a machine-readable medium that is accessible by one or more processors 150 for providing functionality shown and described herein.

Figure 3D:
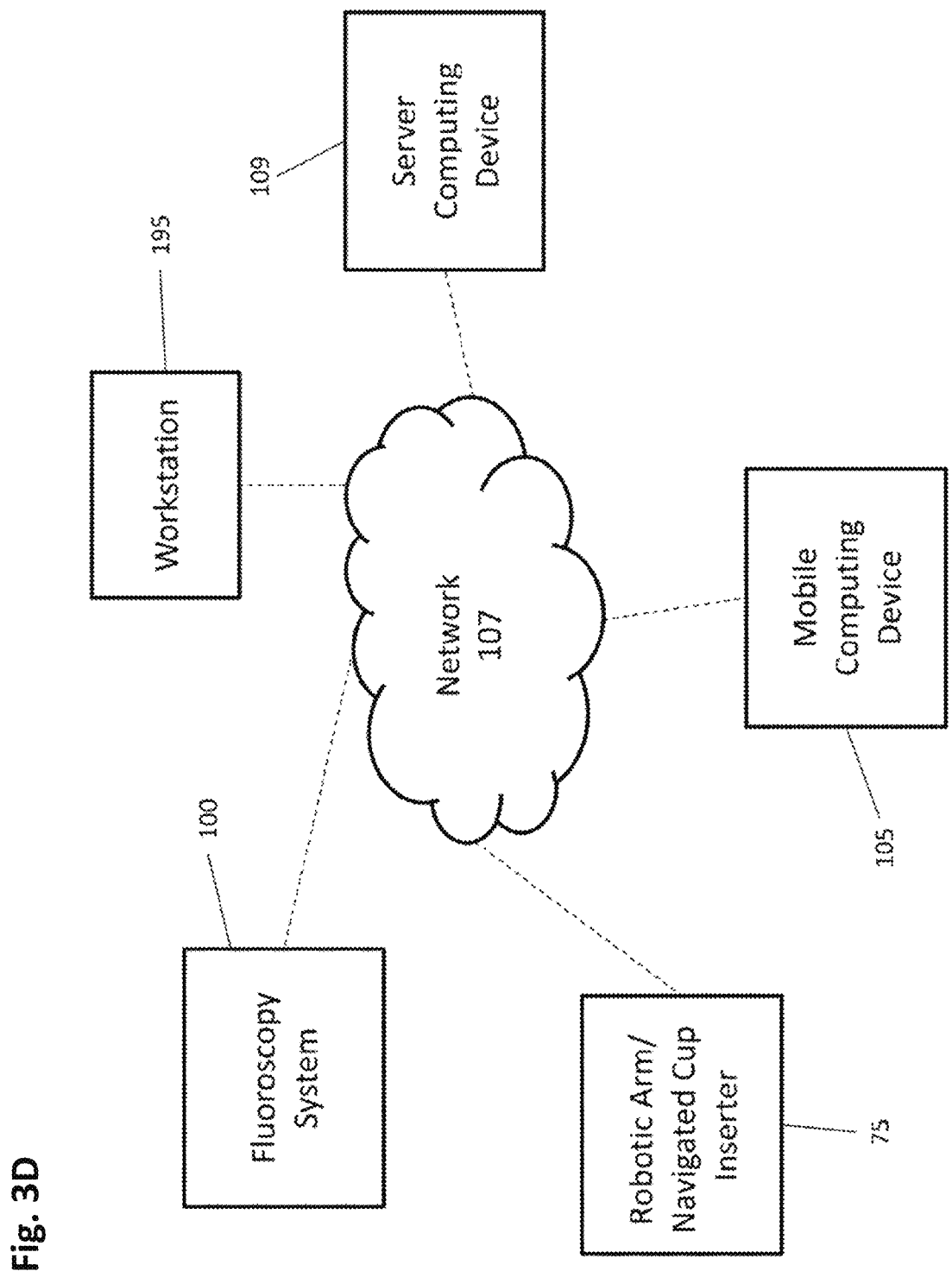
FIG. 3D is a block diagram illustrating an exemplary network configuration in accordance with one or more embodiments.

In one embodiment disclosed herein as shown in FIG. 3D, the fluoroscopy system 100 communicates with a main or server computing device 109 and/or a mobile computing device 105 (e.g., a tablet) over a communications network 107 to allow the surgeon (or other user) to view the images (radiographic images) generated by the fluoroscope and also permit, via a user interface, the user to provide input that is used to calculate certain angles (inputs) that are used to calculate the anteversion angle of the acetabular cup. These details are described in more detail herein. This arrangement allows for the surgeon to view substantially in real-time radiographic images of the surgical site including the acetabular cup position and also allows the surgeon to control certain movements of the surgical equipment. In other arrangements, the actual subsequent cup positioning step(s) can be performed by a user controlled robotic arm or navigated insertion tool (navigated cup inserter) that communicates with and receives control signals from a processor 150 (e.g., associated with a server computing device).

With continued reference to FIG. 3D, various forms of computing devices are accessible to the network 107 and can communicate over the network to the various machines that are configured to send and receive content, data, as well as instructions that, when executed, enable operation of C-arm unit 120. The content and data can include information in a variety of forms, including, as non-limiting examples, text, audio, images, and video, and can include embedded information such as links to other resources on the network, metadata, and/or machine executable instructions. Each computing device can be of conventional construction, and while discussion is made in regard to servers that provide different content and services to other devices, such as mobile computing devices 105, one or more of the server computing devices 109 can comprise the same machine or can be spread across several machines in large scale implementations, as understood by persons having ordinary skill in the art. In relevant part, each computer server has one or more processors, a computer-readable memory that stores code that configures the processor to perform at least one function, and a communication port for connecting to the network 107. The code can comprise one or more programs, libraries, functions or routines which, for purposes of this specification, can be described in terms of a plurality of modules, residing in a representative code/instructions storage, that implement different parts of the process described herein.

Further, computer programs (also referred to herein, generally, as computer control logic or computer readable program code), such as imaging software, can be stored in a main and/or secondary memory and implemented by one or more processors (controllers, or the like) to cause the one or more processors to perform the functions of the invention as described herein. In this document, the terms "memory," "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like. It should be understood that, for mobile computing devices (e.g., tablet), computer programs such as imaging software can be in the form of an app executed on the mobile computing device.

Referring again to FIG. 3A, the C-arm 120 can be tilted in order to provide an accurate image of the pelvic area during THA. In one or more embodiments, the C-arm tilt angle can be used to determine the anteversion angle of the acetabular implant. In one or more embodiments, the C-arm tilt angle and anteversion angle can be determined as discussed in U.S. application Ser. No. 15/501,671 ("'671 application") filed on Aug. 5, 2016, the contents of which are hereby incorporated by reference in its entirety. As discussed in the '671 application, the intraoperative cup (acetabular component) anteversion can be calculated based on the measured acetabular component abduction angle and the measures C-arm tilt angle (CaT). In one or more embodiments, the intraoperative cup anteversion can be automatically calculated by the control console 130 as the CV and CI angles are measured. More particularly, the following equation expresses the CV (angle) as a function of the CI (angle) and the CaT angle:

$$CV = \tan^{-1}[\tan(CaT)\sin(CI)]$$

Referring again to FIG. 3A, the workstation 195 can be configured as a standalone unit or an integrated component within the fluoroscopy system 100. In one or more embodiments, operation of the C-arm 120 is navigated at the workstation 195 and can include the following: power switch, exposure switch, brake pedal, controls radiographic settings, fluoroscopic settings, hard disk, optical disk, writer/rewriter, DVD-R/RW- PACS, advanced image quality enhancement software, noise reduction, zoom control, save and swap images, and single or dual monitors. The C-arm 120 is defined by a curved arm with an x-ray tube (x-ray source) mounted on one end of the arm and the image intensifier 101 (image amplifier) or flat-panel digital detector on the other end of the arm. The image amplifier 101 is defined by a plane that passes therethrough, as discussed herein. Furthermore, the C-arm 120 is constructed to be movable in a controlled manner relative to the support table 110 and, thus, relative to the patient. In some embodiments, the C-arm 120 can perform both linear and rotating motions for optimum positioning with respect to the patient.

Referring again to FIG. 3C, in one or more embodiments the fluoroscopy system 100 uses a camera (e.g., I/O device 170) to scan and transmit the radiographic image to a remote display monitor (e.g., processor 150 instructs display controller 180 to display the image on display monitor 190). Flat-panel detectors use a scintillator material to convert x-rays to visible light, which is translated into a signal suitable for digital display. It will be appreciated that the foregoing is only a description of one exemplary system 100.

In one or more embodiments, the control console 130 is physically integrated with C-arm 120, resides in a structure entirely separate from the C-arm, or is partially integrated with the C-arm and partially separate. The control console 130 (occasionally collectively or individually referred to herein as "processor") can include one or more data processing apparatuses that can include, for example, mobile computing devices 105 such as tablet computing devices, smartphones, personal digital assistants or the like, as well as laptop computers and/or desktop computers.

In other embodiments, the control console 130 may be a network computer (109) or an embedded processing apparatus within another device or consumer electronic product. As noted herein, the control console 130 can be configured to access one or more databases such as provided in memory 160, and usable the present application. Such databases can include, for example, image files, video content, documents, audio/video recordings, metadata and other information. For example, the control console 130 can store radiographs or anteversion measurements made by the fluoroscopy system 100. Control console 130 can also communicate with devices comprising databases using any known communication method, including a direct serial, parallel, universal serial bus ("USB") interface, or via a local or wide area network.

In one or more embodiments, the control console 130 can provide at least some of the functionality in accordance with the teachings herein. Control console 130, server computing device 109 and/or mobile computing device 105 can be configured to include one or more microprocessors 150 and/or other connected system components (e.g., multiple connected chips) or the control console 130 may be configured with system-level on a chip.

As noted herein, the control console 130, server computing device 109 and/or mobile computing device 105 includes memory 160 (e.g., non-transitory processor readable media) which is accessible and/or coupled to the processor(s) 150. The memory 160 may be used for storing data, metadata, and programs for execution by the microprocessor(s) 150. The memory 160 may include one or more of volatile and non-volatile memories, such as Random Access Memory ("RAM"), Read Only Memory ("ROM"), Flash, Phase Change Memory ("PCM"), or other type.

The control console 130 can also be configured to include one or more input or output ("I/O") devices and interfaces 170, which are provided to allow a user to provide input to, receive output from, and otherwise transfer data to and from the system. These I/O devices may include a mouse, keypad or a keyboard, a touch panel or a multi-touch input panel, camera, network interface, modem, other known I/O devices or a combination of such I/O devices. The touch input panel may be a single touch input panel which is activated with a stylus or a finger or a multi-touch input panel which is activated by one finger or a stylus or multiple fingers, and the panel is capable of distinguishing between one or two or three or more touches and is capable of providing inputs derived from those touches to the control console 130. The I/O devices and interfaces 170 may include a connector for a dock or a connector for a USB interface, FireWire, etc. to connect the system 100 with another device, external component, or a network.

Moreover, a display controller 180 and display device 190 can provide a visual user interface for the user; this user interface may include a graphical user interface which, for example, is similar to that shown on a desktop, laptop, tablet or mobile device when running Mac OS, Windows OS, Android, Linux, or other common operating system software. Further, one or more buses can be included that interconnect various modules, such as illustrated in the block diagram shown in FIG. 3C.

It will be appreciated that additional components, not shown, may also be part of or otherwise accessible to the control console 130, and, in certain embodiments, fewer components than that shown in FIG. 3C may also be used in control console 130. The computer-implemented methods may be carried out in a computer system or other data processing system in response to its processor or processing system executing sequences of instructions contained in a memory, such as memory 160 or other machine-readable storage medium. In various embodiments, hardwired circuitry may be used in combination with the software instructions to implement the present embodiments. Thus, the techniques are not limited to any specific combination of hardware circuitry and software, or to any particular source for the instructions executed by the control console 130.

Referring again to FIG. 3D, as mentioned herein, in one or more embodiments, a robotic implementation of the present invention is provided such that the acetabular cup can be grasped by a controllable robotic arm 75 (FIG. 3D). The controllable robotic arm 75 can include or otherwise be accessible by processors and communication modules that are in communication over network 107 with one or more of the fluoroscopy system 100, the main computing device 109, and the mobile computing device 105. The robotic arm 75 can be configured with one or more robotic grippers that are each configured to grasp a handle (post) that is coupled to the acetabular cup 10 to allow for repositioning of the acetabular cup 10 relative to the patient's body. The robotic arm 75 can thus either control: cup position, or direct the C-arm (120). Alternatively, a navigated instrument can be directed to help adjust the cup position until the cup is in line (in registration) with the data (e.g., visual radiographic image guidance, an output indicating target cup position achieved, etc.) provided by the control panel. In other words, the navigated instrument is in communication with the hardware described herein and can be configured to adjust the position of the acetabular cup. Since the navigated instrument includes navigational markers, the location of the navigated instrument can be calculated and since the navigated instrument is coupled to the cup, the cup's movements can be detected and measured. The control console or other hardware described herein can thus provide instructions (which can be displayed on the display) to the user directing how the acetabular cup should be positioned and/or repositioned with the patient.

The robotic arm 75 can further include navigational markers (e.g., tracking elements) and navigation software can be executed via one or more processors to control the movement of the robotic arm 75. In addition, one or more tracking elements can be associated with the patient (i.e., can be coupled to a bone (e.g., pelvis bone) of the patient) to allow for measurement and tracking of not only the location of the robotic arm and thus, the acetabular cup but also the location and position of the patient (e.g., pelvic bone). In this manner, the robotic arm 75 can be controlled and moved relative to the surrounding anatomical landscape to allow for positioning and/or repositioning of the acetabular cup.

Method for Correcting Fluoroscopic Magnification

During a THA procedure, fluoroscopy can be used to allow the physician to view real-time X-ray images of the hip area on a display. In order to properly position the hip implant during THA, the physician must have accurate measurements of the hip area of the patient, as well as accurate measurements of the orientation of acetabular cup of the implant. Fluoroscopy, however, can result in an image of the hip area and implant that are magnified and/or distorted, which make it difficult to determine actual measurements of the patient and the implant from the fluoroscopic images alone.

For certain types of procedures, conventional x-rays (radiographs) can be taken of the surgical area prior to commencing the surgical procedure. Like fluoroscopic images, radiographs can also have a magnification because of the differences in the distance of the object being imaged relative to the film. Specifically, the larger the distance between the imaged object and the film, the larger the magnification of the image is. Conventionally, in order to account for this magnification issue for radiographs, a magnification ball of a known diameter (e.g., 25 mm) is used as a reference in the image. The magnification ball is placed at the same distance from the imaging machine as the area on the patient that is being imaged, such that when the radiograph of the area on the patient is taken, the magnification ball can be used to determine the magnification of the resulting image.

For example, FIG. 4 displays an exemplary anterior posterior (AP) radiographic image of a human pelvis, in which a magnification ball (reference ball) of 25 mm size is placed at the same distance to the radiograph as the hip osseous structures. As such, by knowing the size of the magnification ball, a measurement of the magnification ball in the radiographic image can be compared with the actual size of the magnification ball to determine the amount of magnification ("magnification factor") of the radiographic image. This magnification factor can then be used to determine the actual measurements of the hip structures from the radiographic image.

The magnification factor can be determined manually or via imaging software, as shown in FIG. 5. The image of FIG. 5 shows the graphical user interface of an imaging software program (e.g., PACS imaging software) determining the magnification factor (magnification scale) of the radiographic image based on the known, actual size of the magnification ball and the size of the magnification ball as shown in the image.

Conventional radiography cannot be utilized during a surgical procedure such as THA. As such, fluoroscopy (e.g., a C-arm fluoroscope) is used for intraoperative imaging, as the fluoroscopy unit is mobile and can be utilized in an operating room. Fluoroscopic images are difficult to standardize, as fluoroscopy machines from different manufacturers have differing amounts of magnification and distortion relative to one another. While, in theory, a magnification ball can be used in fluoroscopy in a similar fashion as used for standard pre- and post-operative radiographic images, the use of a magnification ball in this way during surgery would be problematic as the surgical field needs to remain sterile. Further, the use of a mobile reference point such as a magnification ball during surgery can carry the risk of the ball being displaced into the surgical wound during the procedure.

As such, the current standard for THA procedures has been to utilize the size of the acetabular component of the replacement hip implant as the mobile reference point. More specifically, the inserted metal acetabular component implant has a known diameter, and this known diameter can be used to determine the magnification factor in the fluoroscopic images. For example, when using software for imaging position, one can use the acetabular component on the image to calculate the magnification of the image and correct measurements for leg length. This is the current standard for most software applications that attempt to correct magnification during THA.

FIG. 6A-E shows exemplary fluoroscopic images of the hip joint during THA, which shows the acetabular component implant. In order to ensure that the leg of the patient that includes the hip implant will operate in harmony with the other leg of the patient, the leg length for each leg and the offset for each hip must be measured and compared to determine if any adjustments need to be made in the implant.

Measuring Leg Length

Figure 6B:
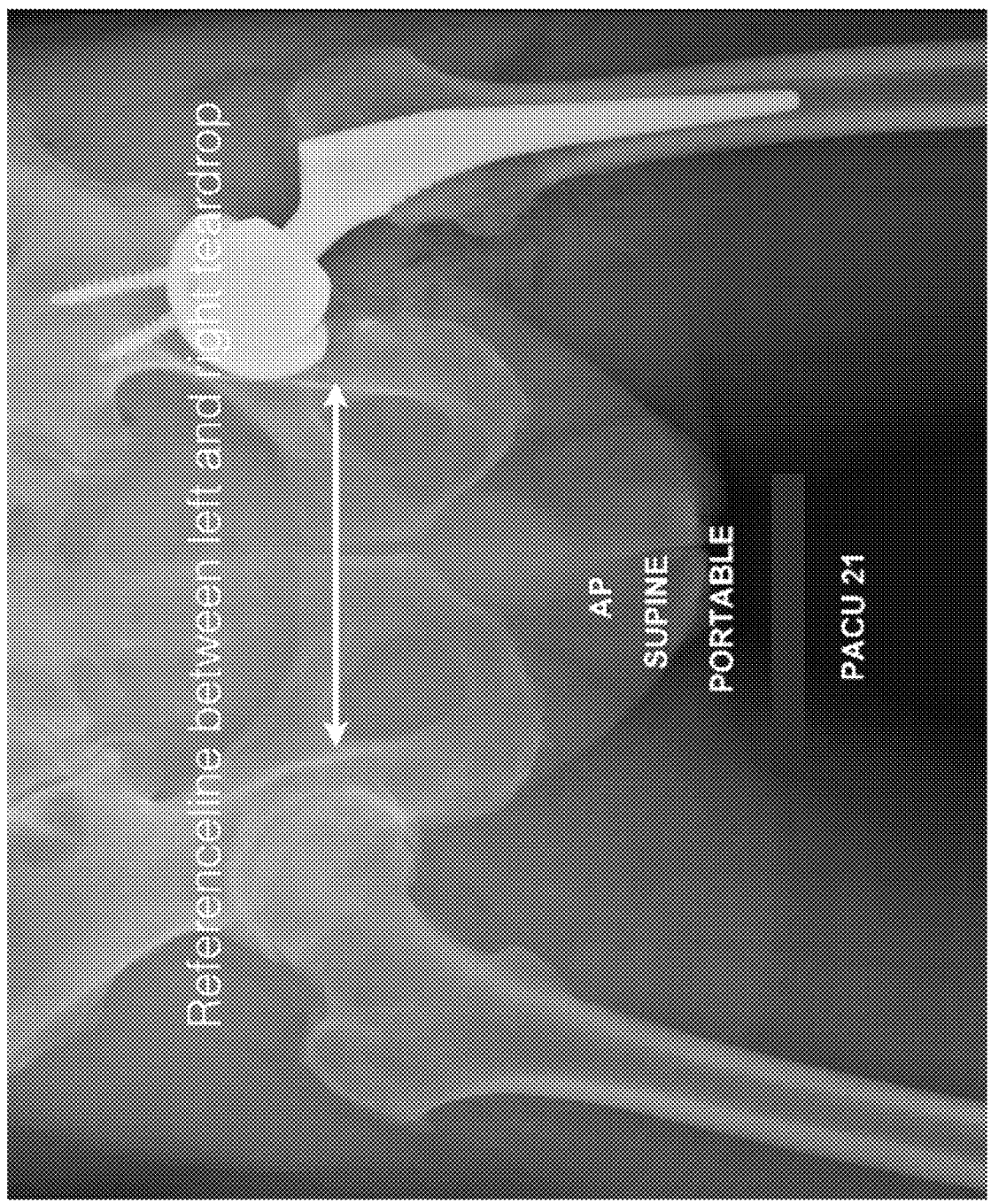

For the measurement of the leg length, one has to visualize both hip joints to compare the position of the left and right leg and ultimately calculate leg length discrepancy. As shown in FIG. 6A, using a superimposed reference line through both pelvic tear drops, the leg length is measured as the distance between the tear drop line and the lesser trochanter 605 on each side. FIG. 6B shows a zoomed out image of the hips showing the superimposed reference line between the right and left teardrop.

As shown in FIG. 6A, the leg length discrepancy between the legs is the difference between distance X and distance Y. A difference between X and Y will be recognized as a difference in leg length after surgery and can be felt by the patient as an unevenness of the legs. Lengthening of the operated leg can result in stiffness as well as a limp while shortening of the operated leg can result in insufficient muscle tension and muscle weakness resulting in a limp or instability of the hip.

To measure leg length, it is important to visualize both hips on one screen at the same time to compare a selected reference point on the femur (lesser trochanter) to a reference line aligned with the pelvis (inter tear drop line).

Measuring Offset of the Hip

Figure 6C:
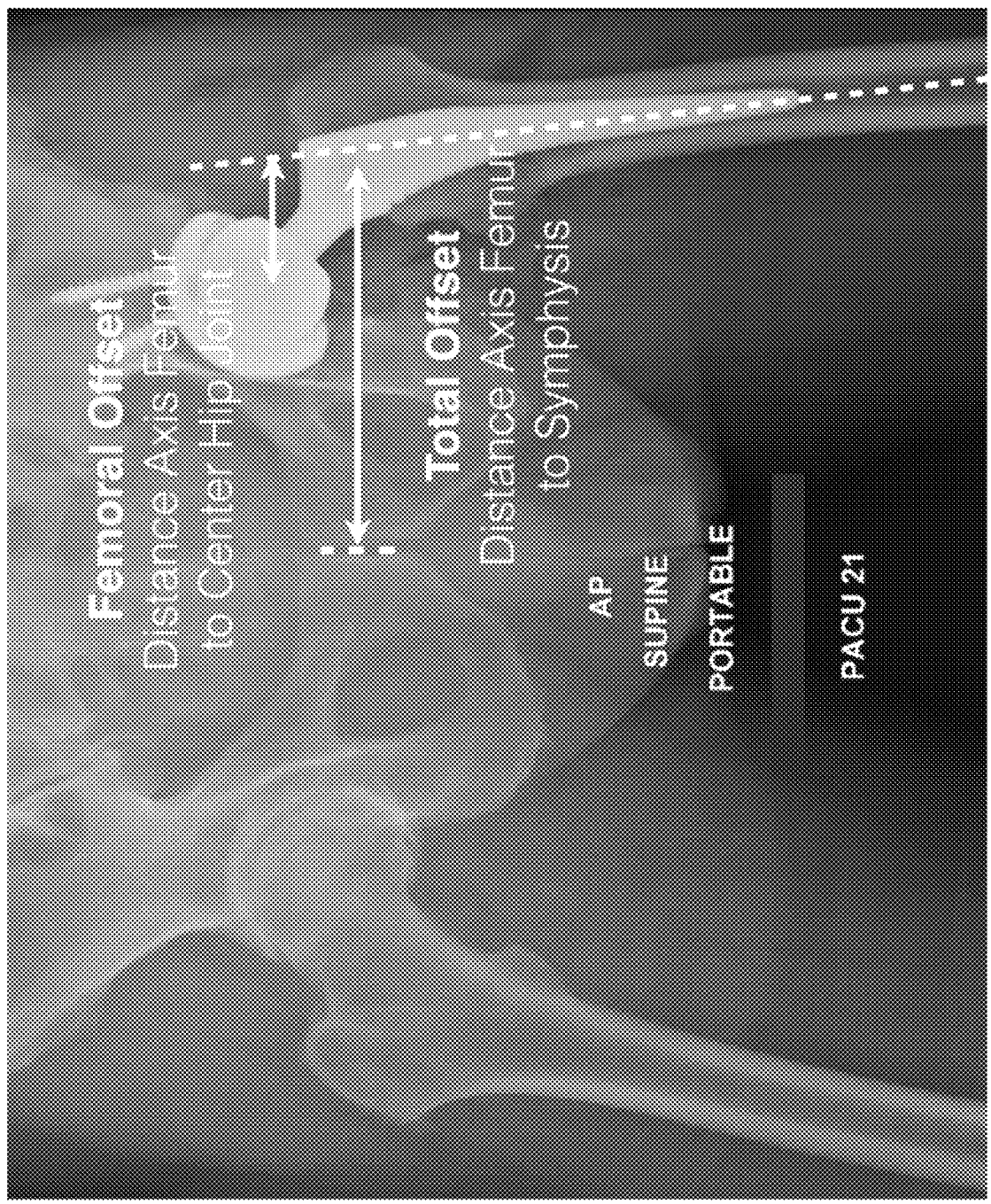
Figure 6D:
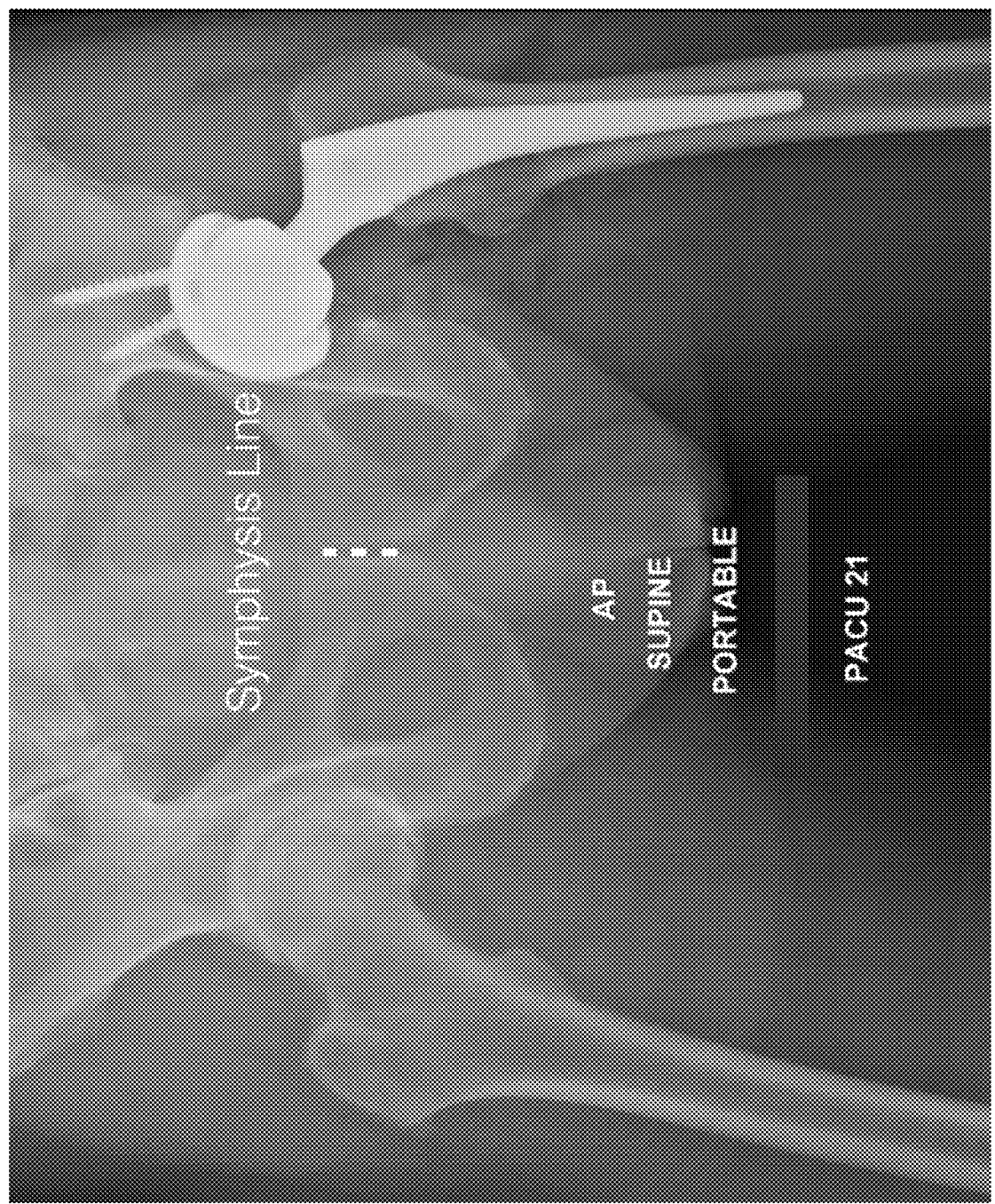
Figure 6E:
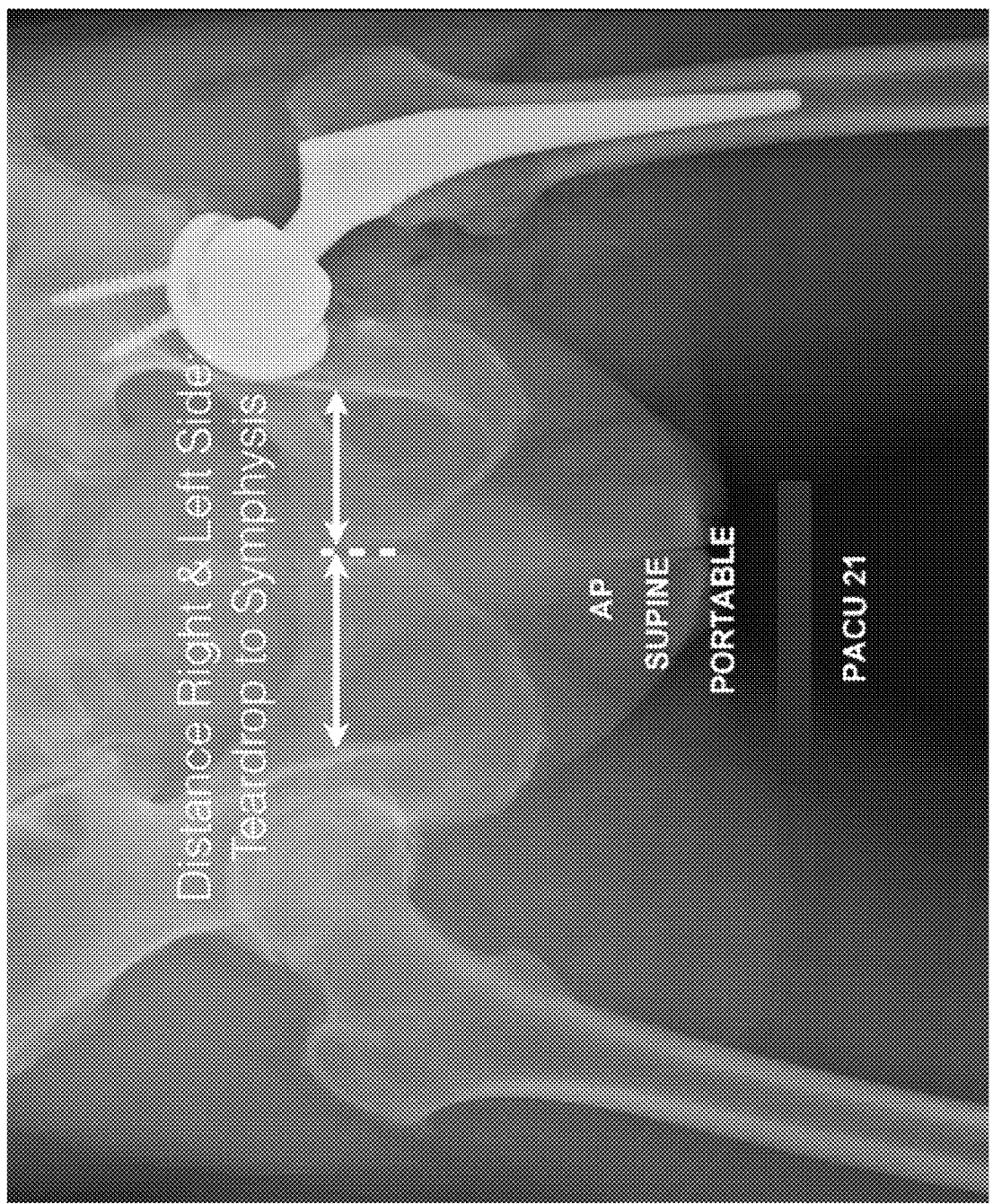

Visualizing both hips in the image is also important for measuring the offset of the hip during a THA procedure. The implantation of the femoral component (implant) influences the femoral offset and total offset of the hip joint. FIG. 6C shows the femoral offset (distance between the axis of the femur and the center of the femoral head, and the total offset, i.e., the distance between the axis of the femur and the symphysis. The femoral offset and the total offset can be measured and compared between left and right side of a patient. The distance between the symphysis and the teardrop on each side can also be measured (see FIG. 6E). Restoration of the offset (femoral and total) is important to optimize the function of the particular muscles especially the abductor muscle and to control the tension of the IT band. In particular, optimal restoration of the femoral offset minimizes postoperative stiffness, trochanteric bursitis and limping. If the pelvis is tilted, then the distance between the tear drop and the symphysis becomes larger on one side than the other as shown in FIGS. 6D-E. The ratio between the distance between teardrop and symphysis on both sides can be used to calculate a correction factor to compare the offset of the hip on both sides. For instance, if the distance between the symphysis and right teardrop is 60 mm and the distance between the symphysis and the left teardrop is 40 mm, the ratio between both is 3:2. This ration of 3:2 can then be used to calculate the difference in total offset. For example, if in this example the total offset of the right side is 120 mm and the total offset on the left side is 90 mm than the difference in offset is calculated as 120 mm/3−90 mm/2=40 mm−45 mm=−5 mm. Suggesting that the left hip has 5 mm more offset than the right side.

When both hips are displayed on one image, the acetabular component is imaged on the border of the image away from the central beam of the fluoroscope (e.g., C-arm fluoroscope). However, the image of objects outside of the central beam of the fluoroscope is then distorted, which is understood as the parallax effect. The amount of distortion of the image as a result of the parallax effect is larger the farther away an image is from the central beam of the fluoroscope. When utilizing fluoroscopy for intraoperative imaging, the effect can be easily visualized on the image itself.

For example, FIG. 7 shows a fluoroscopic image of the pelvis of patient including the inserted acetabular cup component. As shown in FIG. 7, the acetabular cup, which is spherical in nature, is distorted in the fluoroscopic image into an oval shape as a result of not being positioned within the central beam of the C-arm fluoroscope. As such, using the acetabular cup's dimensions in the fluoroscopic image as a reference point for measuring other aspects of the pelvic area can lead to inaccurate measurements due to the distortion of cup in the image. Additionally, sometimes the fluoroscopic image of the acetabular cup does not show the entire cup due to the location of the fluoroscope (see FIG. 6A). Thus, in fluoroscopic images such as those shown in FIGS. 6A and 7, both distortion and an incomplete image of the acetabular cup prevent the cup from being used as a viable reference point for measuring other aspects of the hip area.

Accordingly, in at least one aspect, the present application provides a new method for correcting the magnification of the fluoroscopic image in order to accurately determine the dimensions of certain aspects of the hip area during a THA procedure.

Turning now to FIG. 8, a flow diagram is described showing a routine 800 that illustrates a broad aspect of the method for correcting the magnification of the fluoroscopic image in accordance with one or more embodiments. It should be appreciated that several of the logical operations described herein are implemented as a sequence of computer-implemented acts or program modules running on one or more computing devices that are operatively connected to the fluoroscopy system (e.g., mobile computing device, server computing device) and/or as interconnected machine logic circuits or circuit modules within the system. Accordingly, the logical operations described herein are referred to variously as operations, steps, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

The process begins at step 805 where a radiographic image (conventional x-ray image) of the pelvic area of a patient is taken. A reference ball with a known diameter is placed in close proximity to the hip prior to the radiograph (x-ray) being taken such the ball is displayed in the radiographic image. Accordingly, radiographic image, such as the one displayed in FIG. 4, is taken such that the reference ball and the structures of the hip joint are visible in the image.

At step 810, the diameter of the reference ball in the radiographic image is measured and compared with the known diameter of the actual reference ball to determine the magnification amount (magnification factor) of the radiographic image. In one or more implementations, this step can be a computer-implemented step executed via imaging software, as exemplified in FIG. 5. For example, as shown in FIG. 5, a computing device (e.g., mobile computing device) executing the imaging software can be configured to detect the diameter of the reference ball in the image (e.g., 31.2 mm) and via input on the computing device, a user can input the actual diameter of the reference ball (e.g., 25 mm). Based on the actual diameter of the reference ball and the determined size of the ball in the image, the imaging software is configured to determine the magnification factor of the radiographic image (e.g., approximately 120%).

At step 815, a reference line is created in the radiographic image and the determined magnification factor is used to measure a reference line in the radiographic image between two anatomical landmarks on the pelvic area of the patient. In one or more implementations, the reference line can be the line between the left "tear drop" and right "tear drop" on the floor of the acetabulum. Alternatively, the reference line can be a line between the ends of the lower portion of the obturator foramen or a line between the tips of the tuber ischiadicum. Exemplary reference lines are shown in FIG. 9. In one or more embodiments, step 815 can be a computer-implemented step in which a user using the graphical user interface of the imaging software can select two anatomical landmarks in the radiographic image, and the processor executing the imaging software is configured to then create a line between the two chosen anatomical points (see FIG. 9). In one or more implementations, the anatomical landmarks can be selected by the user (e.g., physician) by hand via a touchscreen on a tablet, for example, or by use of an instrument operatively connected to the computing device (e.g., mouse, touchscreen stylus). Once the line has been created, the processor executing the imaging software is configured to measure the actual length between the selected anatomical landmarks. The reference line is established in order to accurately measure the leg lengths (distance between the tear drop line and the lesser trochanter of each femur) of the patient, as discussed in further detail below.

Appropriate restoration of the distance Y on the hip implant based on Distance X (see FIG. 6) allows one to control hip joint-related leg length. For example, referring back to FIG. 6A, increasing Distance Y on the hip implant will result in a longer left leg which can have implications for function. Increased length can increase soft tissue tension and result in stiffness. Shortening of the distance compared to the other side can result in instability or inadequate muscle tension resulting in muscle weakness.

At step 820, imaging software is configured to determine the magnification factor of the fluoroscopy based on the determined length of the reference line. More specifically, one or more fluoroscopic images of the pelvic area of the patient are taken during the THA procedure. For instance, in at least one implementation, via the imaging software running on the computing device, a user can re-create the same reference line (i.e., a line created between the two anatomical landmarks) created in the radiographic image in the fluoroscopic image. The line creation in the fluoroscopic image can be accomplished via user input in substantially the same way as discussed in step 815 with the radiographic image (i.e., selecting the two anatomical landmarks in the image and creating a line connecting the two). After creation of the reference line in the fluoroscopic image, the processor executing the imaging software is configured to determine the actual length measurement of the reference line.

At step 825, the actual leg length distance and offset in the patient is determined based on the calculated magnification factor of the fluoroscopy. Specifically, in one or more embodiments, the user using the graphical user interface of the imaging software can select the two end points of the leg length, and the processor can then be configured to create a line between the two selected end points, representing the leg length. Similarly, the user using the graphical user interface of the imaging software can select the two end points of the offset distance (femoral and/or total), and the processor can then be configured to create a line between the two selected end points, representing the offset distance. Based on the magnification factor as determined at step 820, the processor executing the imaging software is configured to determine the actual leg length and offset distances. The leg length and offset distances between each leg of the patient can be compared to determine if any adjustment need to be made to the implant. At step 830, the method ends.

In one or more alternative embodiments, a modified method for correcting the magnification of the fluoroscopic image can be utilized. In this method, a reference ball (magnification ball) having a known diameter is used during both radiography and intraoperative fluoroscopy to correct the magnification of the fluoroscopic image and determine the leg length of the patient. As mentioned above, the use of a reference ball during intraoperative fluoroscopy is typically not preferred as the surgical environment must remain sterile. However, in this method, the reference ball is placed within the post.

Exemplary implementations of the post between the legs of a patient and the reference ball are shown at FIGS. 10A-D. In particular, FIG. 10A shows an implementation of the post 1005, where the post is fixed onto the operating table and the reference ball 1010 with a known diameter is placed within the post 1005 in accordance with one or more embodiments. FIG. 10B shows a diagram of the reference ball 1010 within the post 1005 in accordance with one or more embodiments. In the embodiment of FIG. 10B, the post 1005 can include a cylindrical padded positioning tool (padding) 1015 that is placed between the legs of the patient. It functions as a resistance on the pelvis that allows one to place traction on both legs and position and stabilize the pelvis. The padding 1015 also minimizes pressure on the patient's pelvis. Additionally, the post 1005 can include an adjustment tool 1020 for vertically adjusting the height of the magnification ball (reference ball) 1010 within the post 1005. It should be understood that, in other implementations, the reference ball can be attachable and moveable along the post in any number of ways as would be understood by a person of ordinary skill in the art.

FIGS. 10C-D show a fluoroscopy image of the hip area, including the magnification ball within the post. In particular, FIG. 10C highlights the post 1005 (radiolucent post) in the image, and FIG. 10D highlights the magnification ball 1010 within the post in the image. Because the post is within the fluoroscopy image due to its proximity to the pelvis, the reference ball placed within the post is visualized within the fluoroscopy image. The height of the reference ball within the post is vertically adjustable such that the reference ball can be positioned approximately adjacent to the hip. For example in a small patient, the reference ball within the post might be lowered, while in a larger patient it might be adjusted to a higher position. Since parallax image distortion is symmetric around the central beam of the fluoroscopy unit, one can ultimately determine specific magnification of the ball when visualized in any position of the ball and all the position and size of the ball on a fluoroscopy image to standardize the magnification of the entire fluoroscopy image.

FIG. 11 illustrates a flow diagram showing a routine 1100 that illustrates a broad aspect of this modified method. The process begins at step 1105 wherein a post is positioned between the patient's legs prior to THA surgery. At step 1110, one or both of the legs of the patient are secured to the post to keep the patient's pelvic area steady during the surgery. The post is configured to receive a reference ball (magnification ball) as discussed in further detail below.

At step 1115, a reference ball with a known diameter is positioned inside the post. Its position height within the post can be adjusted using an external adjustment tool (see FIG. 10B) such that the reference ball is aligned with the level of the hip of the patient. The post, because of its proximity to the pelvis, is visualized within the image.

At step 1120, one or more fluoroscopic images of the pelvic area of the patient are taken during the THA procedure. Because the reference ball has a known diameter and is placed at the level of the hip (step 1115), the ball is displayed in the one or more fluoroscopic images. Accordingly, the one or more fluoroscopic images are taken such that the reference ball and the structures of the hip joint are visible in the image(s).

At step 1125, the diameter of the reference ball in the fluoroscopic image is measured and compared with the actual (known) diameter of the reference ball to determine the magnification factor of the fluoroscopic image. In one or more implementations, this step can be a computer-implemented step executed via imaging software. For example, the computing device executing the imaging software can be configured to detect the diameter of the reference ball in the image, and via input on the computing device, a user can input the actual diameter of the reference ball. Based on these two measurements, the computing device executing the imaging software can be configured to determine the magnification factor of the fluoroscopic image.

At step 1130, the leg length (the distance between the tear drop line and the lesser trochanter) for both sides of the hip of the patient is determined based on the magnification factor of the fluoroscopic image. Specifically, in one or more embodiments, the user using the graphical user interface of the imaging software can select the two end points of the leg length in the fluoroscopic image, and the processor of the computing device can then be configured to create a line between the two selected end points, representing the leg length. Similarly, the user using the graphical user interface of the imaging software can select the two end points of the offset distance (femoral and/or total), and the processor can then be configured to create a line between the two selected end points, representing the offset distance. Based on the magnification factor as determined at step 1025, the processor executing the imaging software is configured to determine the actual leg length and offset distances. The leg length and offset distances between each leg of the patient can be compared to determine if any adjustment need to be made to the implant. At step 1135, the method ends.

In one or more implementations, the magnification can change throughout the fluoroscopic image based on the parallax effect. More specifically, the parallax effect is symmetric around the central beam of the fluoroscopy unit with increased parallax the further one moves away from the central beam, as shown in the fluoroscopic image of FIG. 12. The known magnification and distortion of the reference ball 1010, as shown in FIG. 12, can be used to adjust distortion secondary to parallax and magnification throughout the entire fluoroscopy image. Specifically, in one or more embodiments, the user using the graphical user interface of the imaging software can select the reference ball and the processor executing the software can then be configured to standardize the magnification and angular distortions throughout the fluoroscopic image.

Method for Correcting Radiographic Inclination

In addition to complications related to magnification, distortion in fluoroscopic images can affect the accuracy of measurements. Specifically, stereometric effects in two-dimensional projections can affect angle measurements on radiographs. Furthermore, it can impair comparability between intraoperative fluoroscopy and pre- or postoperative standardized radiographic imaging.

With regards to THA procedures, distortions in radiographic and fluoroscopic images can affect the angle measurements of the acetabular cup and, in particular its inclination (CI). Therefore, a standardized technique with regards to these stereographic effects and its pitfalls is needed to achieve reliable intraoperative estimation of the actual acetabular cup inclination.

Radiographic Inclination Study 121 consecutive THA operations were performed in 113 patients using the DAA with intraoperative standardized c-arm fluoroscopy imaging. Every patient received a standardized pre-operative and post-operative standing anterior to posterior (ap) pelvic view with the x-beam of the fluoroscope centered on the symphysis pubis of the patient. The distance between the acetabular plane and the source or fluoroscope (i.e., source-to-object distance) was 100 cm.

The intraoperative c-arm fluoroscopy was performed after insertion of the definite acetabular component (cup). Radiographic inclination of the acetabular cup was defined as angle ρ between the long axis of the projected ellipse of the cup opening and the inter tear-drop line. The angle ρ was measured in the preoperative, intraoperative and postoperative pelvis a.p. view. All radiographic measurements were performed using orthotool box, Sectra PACS software package IDS7.

FIG. 13 shows the same exemplary radiographic image of the hip as shown in FIG. 7. The image of FIG. 13, however, shows how the distortion of the lateral part of the acetabulum influences the measurement of the radiographic inclination. Specifically, as shown in FIG. 13, the inclination angle ABC (i.e., the radiographic inclination angle of the rim of the acetabular component with distortion) is smaller than the angle ABD that would be measured without distortion (i.e., the actual inclination angle of the rim of the acetabular component).

In each of the 121 hips of the study, the mean radiographic inclination of the cup was 35.2 degrees (28.5-41.0, SD 2.81) for intraoperative measurements and 40.1 degrees (34.1-45.0, SD 2.26) for postoperative measurements, as exemplified in FIG. 14. More specifically, FIG. 14 shows the measured radiographic inclination for intraoperative and postoperative images for three different measurements. In each of the three series, there was an approximately equal difference between intra- and postoperative radiographic inclination (4.62°, 4.80°, 4.93°).

The measurements showed a "very strong" ICC for intra-observer (0.91 intraoperative radiographic inclination, 0.92 postoperative radiographic inclination) and for inter-observer (0.85 intraoperative radiographic inclination, 0.85 postoperative radiographic inclination) correlation. The difference between intraoperative and postoperative radiographic inclination was 5° (r=0.538, p<0.000) as shown in FIG. 15. More specifically, FIG. 15 shows the average intraoperative and postoperative radiographic inclination values. The hatched boxes display mathematical results of different correction values (+4°, +5°, +6°) added to the measured intraoperative radiographic inclination. When applying a correction factor of +4° for intraoperative RI, no significant difference to postoperative radiographic inclination is observed.

The accepted target zone for radiographic inclination is between 35° and 45°. As such, based on the measured correction factor of 4° as determined in the 2016 study, we suggest surgeons should aim for a radiographic inclination during surgery (intraoperative) between 36° and 41° so that even accounting for the correction factor, the radiographic inclination will remain in the target zone. In the study, 56 intraoperative images showed a radiographic inclination within this zone. All 56 cups with an intraoperative radiographic within the range of 36° to 41° had a postoperative inclination within the safe zone (mean 40.8°, 37.5° to 45.0°, SD1.87).

Radiographic Inclination Correction Method

In at least one aspect, the present application provides a new method for correcting the radiographic inclination using the correction factor determination from the above study. Specifically, the present method uses intraoperative fluoroscopic images to determine the actual acetabular inclination of the hip implant. Because of the location of the acetabular component during fluoroscopy—outside of the central beam of the fluoroscope—there is a distortion that results in a change of the inclination angle during intraoperative measurements, as shown by the study above. Accordingly, the present method is used to correct the distorted inclination angle in the fluoroscopic image.

FIG. 16 provides a flow diagram showing a routine 1600 for radiographic inclination correction. As shown at FIG. 16, the method begins at step 1605, where the correction factor for the specific fluoroscope is determined. Different fluoroscope models will generally have differing distortion amounts. Accordingly, the correction factor for the model of fluoroscope to be used must be determined. The fluoroscope-specific correction factor can be determined based on the methods of the radiographic inclination study discussed above. Specifically, intraoperative fluoroscopic images and postoperative radiographic images can be taken for a representative number of THA patients to determine the average difference in inclination angle between the two images (i.e., the correction factor). In at least one alternative implementation, the correction factor can be determined by taking fluoroscopic images of patients in which the angle of inclination is already known. Accordingly, the angle of inclination shown in the fluoroscopic images is compared with the actual, known angles of inclination, and the average difference between them is considered the correction factor.

At step 1610, calibration data for the specific fluoroscope can be entered into a database that is operatively connected to an image software program running on the computing device. The calibration data can include the model of fluoroscope as well as the determined correction factor for that model of fluoroscope. The calibration data can be saved in the database operatively connected to the computing device(s) of the system, along with calibration data for other fluoroscope models such that the user can access the correction factors for various types of fluoroscopes via the imaging software.

In one or more embodiments, when the correction factor for the fluoroscope to be used in a particular THA procedure is already saved in the database accessible by the imaging software, steps 1605 and 1610 can be omitted.

At step 1615, prior to beginning a THA operation, the fluoroscope model to be used during the procedure is entered into the imaging software. Specifically, in one or more embodiments, the user (e.g., physician) using a computing device (e.g., tablet) operatively connected to the fluoroscope (e.g., c-arm fluoroscope) enters the model of the fluoroscope into the graphical user interface of the imaging software program via user input.

At step 1620, during the THA operation, one or more fluoroscopic images of the pelvic region of the patient are taken, wherein the images include the acetabular cup of the implant.

At step 1625, the angle of inclination of the acetabular cup in the fluoroscopic image is measured. In one more embodiments, the angle of inclination is determined via the imaging software. For example, the computing device (e.g., tablet) executing the imaging software can be configured to allow the user (e.g., physician) to draw (superimpose) three points on the fluoroscopic image at the acetabular cup, and the software can then be configured to draw (superimpose) lines between those points to create the angle of inclination (see points A, B, and C in FIG. 13). Alternatively, the computing device executing the imaging software can be configured to allow the user to draw (superimpose) the lines on the acetabular cup in the image, and the imaging software can then be configured to determine the angle created between the lines (i.e., the angle of inclination). In another implementation, the computing device executing the imaging software can be configured to automatically detect the acetabular cup in the image, and then generate (superimpose) lines that create a proposed angle of inclination on the image at the acetabular cup. The user can then optionally modify the superimposed lines if the lines are not aligned correctly on the acetabular cup in the image. It should be understood that the imaging software, in accordance with other embodiments, can use other, alternative means for measuring the angle of inclination in the fluoroscopic image as would be understood in the art.

At step 1630, the actual angle of inclination in the acetabular cup of the patient is determined based on the determined correction factor of the particular fluoroscope. The correction factor, as determined at step 1605, is added to the angle of inclination measured at step 1625 to arrive at the actual angle of inclination in the acetabular cup. In the radiographic inclination study discussed above, the correction factor was 4°, and thus 4° was added to the angle of inclination from the fluoroscopic image to arrive at the actual angle of inclination from the acetabular cup. However, it should be understood that different model fluoroscopes can have differing distortion amounts, and thus the correction factor for the various models of fluoroscopes can vary. In one or more implementations, step 1630 can be a computer-implemented step executed via the imaging software. For example, a computing device (e.g., mobile computing device) executing the imaging software can be configured to retrieve the correction factor for the fluoroscope from the database. Based on the retrieved correction factor and the measure angle of inclination in the fluoroscopic image, the computing device executing the imaging software can be configured to determine the actual angle of inclination in the acetabular cup.

Once the actual angle of inclination in the acetabular cup is determined, at step 1635 it is determined whether the actual angle of inclination is within the accepted target zone ("safe zone") for inclination—35°-45° as discussed above. This target zone or safe zone maximizes the stability of the hip and helps to minimize wear on the implant material. If the actual angle of inclination is within the accepted target zone, then the method ends as step 1640.

If, however, the actual angle of inclination is not within the accepted target zone of 35°-45°, then the method continues at step 1645, where the acetabular cup of the hip implant is manipulated by the user (e.g., physician) in the body of the patient in an effort to change the angle of inclination of the acetabular cup such that it is in the target zone. The acetabular cup of the hip implant can be manipulated using any number of techniques as is known in the art. For example, in one or more embodiments, the positioning or manipulation of the acetabular cup can be performed via a user-controlled robotic arm or navigated insertion tool (navigated cup inserter) that communicates with and receives control signals from a processor operatively connected to the fluoroscopy system.

After the manipulation of the acetabular cup at step 1640, the method returns to step 1620, where one or more fluoroscopic images of the pelvic region are taken. The angle of inclination in the fluoroscopic image is then re-measured at step 1625 and the actual angle of inclination for the acetabular cup (in its manipulated position) is then determined at step 1630. Next it is again determined whether the actual angle of inclination is within the target zone at step 1635. If so, the method ends at step 1640, but if not, then the method again moves to step 1645 where the acetabular cup of the hip implant is again manipulated by the user (e.g., physician) in an effort to change the angle of inclination such that it is in the target zone.

Method for Measuring Inclination and Anteversion

As mentioned above, when the acetabular cup is outside of the central beam of the fluoroscope, distortion in the fluoroscopic image occurs. However, if the central beam of the fluoroscope is centered over the acetabular component, the resulting fluoroscopic image shows little to no distortion of the acetabular cup. Accordingly, when the central beam of the fluoroscope is centered over the acetabular component, the measurements of the acetabular cup, namely inclination and anteversion, can be made without a correction factor. This is exemplified in FIG. 17, which shows a fluoroscopic image of the acetabular cup in which the central beam of the fluoroscope is centered over the acetabular component. Accordingly, in the image of FIG. 17, there is no distortion in the acetabular cup as the acetabular cup is shown in its actual shape—a spherical shape—as compared with a distorted oval shape (see FIG. 7).

The inclination of the acetabular cup can therefore be easily measured as long as the fluoroscope is perfectly centered in line with the pelvis at an angle of the line on the opening of the cup and the horizontal line of the image. This is exemplified in FIG. 18, which shows that the angle of inclination the angle between the horizontal plane of the image and a line on the opening of the ellipse. In other methods, some have used reference lines to correct the position of the fluoroscope, but for the purpose of the following method, it will be understood that the fluoroscope (e.g., c-arm fluoroscope) is moved at a 90 degrees angle relative to the longitudinal axis of the patient's body positioned on the surgical table and perfectly centered over the hip.

Anteversion can also be measured from this view of the fluoroscope (i.e., centered over the acetabular cup). More specifically, anteversion of the acetabular cup is generally calculated as the inverse sinus (arcsin) of the short axis of the acetabular cup over the long axis of the acetabular cup (see FIG. 19). In other words, anteversion=arcsin (short axis/long axis).

During surgery, however, it is not possible to easily calculate an inverse sinus function. Therefore, Widmer et al. (2004) analyzed the relationship of acetabular anteversion and the ratio between short axis and total length of the acetabular cup (see FIG. 20). Widmer et al. reported that anteversion can be expressed as a function of short axis and total length in which there is anteversion=48.05*(short axis [mm]/total length [mm]−0.3 for cup positions between 10 and 30 degrees of anteversion. The target anteversion for an acetabular component operated on from a direct anterior or anterolateral approach is 10 to 25 degrees of anteversion. As such, if the THA operation is using a direct anterior or anterolateral approach, the relationship between the short axis and the total length, as shown above, can be used to calculate anteversion of the acetabular cup.

In accordance with one or more embodiments of the present application, the following method utilizes the relationship between the short axis and the total length of the acetabular cup in order to create a target anteversion of the acetabular cup of a patient. Specifically, the present method utilizes imaging software to create a target anteversion by superimposing three lines on a fluoroscopic image of the acetabular cup. The three lines can be positioned in a particular distance ratio representing a target anteversion. The positioning of the three lines is based on the above equation defining relationship between the short axis and the total length of the acetabular cup.

FIG. 21 provides a flow diagram illustrating a routine 2100 for measuring the degree of anteversion of the acetabular cup. As shown in FIG. 21, the method begins at step 2105, where the target degree of anteversion is selected. As mentioned above, in general, the target anteversion for an acetabular component operated on from a direct anterior or anterolateral approach is 10 to 25 degrees. Accordingly, in one or more implementations, the target degree of anteversion is selected from the range of 10 to 25 degrees. In one or more embodiments, the selected target degree of anteversion can be entered into and stored in a database operatively connected to the computing device (e.g., tablet), where such computing device is executing the imaging software. The selected target degree of anteversion is then accessible by the imaging software.

At step 2110, a fluoroscopic image of the pelvic region is taken where the fluoroscope's central beam is centered over the acetabular cup such that little to no distortion is shown in the fluoroscopic image of the acetabular cup.

At step 2115, the computing device (e.g., tablet) executing the imaging software (e.g., imaging software app) is configured to generate three lines superimposed on the acetabular cup of the fluoroscopic image, where the three lines are positioned relative to each other based on a ratio determined by the target anteversion. Specifically, the positioning of the three superimposed lines is based on the relationship of the target anteversion with the short axis and the total length of the acetabular cup. For example, FIG. 22 shows an exemplary fluoroscopic image featuring the three superimposed lines. As shown in FIG. 22, the distance between line 1 and line 2 is the distance of the short axis of the acetabular cup and the distance between line 1 and 3 is the distance of the total length of the acetabular cup. As such, the positioning of each of the three lines relative to one another is based on the equation: target anteversion=48.05*(short axis/total length)−0.3. For example, if the target anteversion is 20°, then the ratio of short axis/total length=20+0.3/48.05=0.42248. This ratio is then used by the imaging software to determine the locations of the three lines relative to one another. In one or more embodiments, the computing device executing the imaging software can be configured to automatically generate the three lines based on the target degree of anteversion.

Referring again to FIG. 21, at step 2120, the computing device executing the imaging software is configured to align the three superimposed lines with the acetabular cup of the fluoroscopic image. In one or more embodiments, the computing device executing the imaging software can automatically detect the acetabular cup and thus upon generation of the three lines, the software can automatically align the lines as closely as possible with the edges of the acetabular cup. In particular, as shown in FIG. 22, lines 1 and 2 are aligned with the two bottom edges of the acetabular cup on opposing sides and line 3 is aligned with the top of the acetabular cup. In at least one embodiment, the user (e.g., physician) can manually move the superimposed lines such that they align with the correct positions along the acetabular cup in the fluoroscopic image. This can be done by the user by manipulation of the lines via a touchscreen on a tablet, for example. In embodiments in which the user manually aligns the superimposed lines, the superimposed lines maintain their prescribed ratio (determined by the target anteversion) during manipulation by the user. In other words, the lines can be moved as a unit such that their prescribed ratio is not changed. In certain implementations, the lines can be zoomed in or out in order to match the size of the acetabular cup in the image, for example; however, the prescribed ratio between the lines is still maintained.

At step 2125, upon alignment of the superimposed lines with the acetabular cup, it is determined whether the anteversion of the acetabular cup in the image (i.e., the patient's acetabular cup) matches the target anteversion. If the superimposed lines align perfectly with the respective locations of the acetabular cup, then the anteversion of the acetabular cup matches the target anteversion. As such, in order for the acetabular cup's degree of anteversion to match the target anteversion, the short axis of the cup in the image must correspond with the distance between lines 1 and 2, and the total length of the cup in the image must correspond with the distance between lines 1 and 3, as shown in FIG. 22.

If the anteversion of the acetabular cup in the image matches the target anteversion, then the method ends at step 2130. However, if the anteversion of the acetabular cup in the image does not match the target anteversion, then the method continues at step 2135, where the acetabular cup of the hip implant is manipulated by the user (e.g., physician) in an effort to change the degree of anteversion of the acetabular cup such that it matches the target anteversion. For example, in one or more embodiments, the positioning or manipulation of the acetabular cup can be performed via a user-controlled robotic arm or navigated insertion tool (navigated cup inserter) that communicates with and receives control signals from a processor operatively connected to the fluoroscopy system. Although, it should be understood that positioning or manipulation of the acetabular cup can be done using any number of techniques as is known in the art.

After the manipulation of the acetabular cup at step 2135, the method returns to step 2110, where a fluoroscopic image of the pelvic region is taken. The three lines are then generated again at step 2115 based on the target anteversion and the superimposed lines are then aligned with acetabular cup in the image at step 2120. Next, it is again determined whether the degree of anteversion of the cup matches the target anteversion at step 2125. If so, the method ends at step 2130, but if not, then the method again moves to step 2135 where the acetabular cup of the hip implant is again manipulated by the user (e.g., physician) in an effort to change the degree of anteversion such that it matches the target anteversion.

An alternative version of routine 2100 is shown at FIG. 23. In particular, FIG. 23 provides a flow diagram illustrating a routine 2300 in which the degree of anteversion of the cup is measured based on the lines superimposed over the cup via the imaging software. As shown in FIG. 23, the method starts at step 2305 where the target degree of anteversion is selected. As mentioned above, in general, the target anteversion for an acetabular component operated on from a direct anterior or anterolateral approach is 10 to 25 degrees. Accordingly, in one or more implementations, the target degree of anteversion is selected from the range of 10 to 25 degrees. In one or more embodiments, the selected target degree of anteversion can be entered into and stored in a database operatively connected to the computing device (e.g., tablet), where such computing device is executing the imaging software. The selected target degree of anteversion is then accessible by the imaging software.

At step 2310, a fluoroscopic image of the pelvic region is taken where the fluoroscope's central beam is centered over the acetabular cup such that little to no distortion is shown in the fluoroscopic image.

At step 2315, the computing device (e.g., tablet) executing the imaging software (e.g., imaging software app) is configured to allow the user draw three lines superimposed on the acetabular cup of the fluoroscopic image. The three lines are drawn to align with the edges of the acetabular cup. In particular, as exemplified in FIG. 22, lines 1 and 2 are aligned with the two bottom edges of the acetabular cup on opposing sides and line 3 is aligned with the top edge of the acetabular cup. The lines can be drawn by the user (e.g., physician) by hand via a touchscreen on a tablet, for example, or by use of an instrument operatively connected to the computing device (e.g., mouse, touchscreen stylus).

At step 2320, the computing device executing the imaging software is configured to measure the anteversion of the acetabular cup in the fluoroscopic image based on the ratio of distances between the superimposed lines. In one or more embodiments, the computing device executing the imaging software can automatically detect the three lines and the distances between those lines. As discussed above, and as exemplified in FIG. 22, the distance between line 1 and line 2 is the distance of the short axis of the acetabular cup and the distance between line 1 and 3 is the distance of the total length of the acetabular cup. As such, the computing device executing the imaging software is configured to measure the anteversion of the cup based on the equation: anteversion=48.05*(short axis/total length)−0.3.

At step 2325, upon measurement of the anteversion of the cup in the fluoroscopic image, it is determined whether the anteversion of the acetabular cup in the image (i.e., the patient's acetabular cup) matches the target anteversion. In one or more embodiments, the computing device executing the imaging software can be configured to automatically compare the entered target anteversion with the measured anteversion. If the measured anteversion of the acetabular cup in the image matches the target anteversion, then the method ends at step 2330. However, if the anteversion of the acetabular cup in the image does not match the target anteversion, then the method continues at step 2335, where the acetabular cup of the hip implant is manipulated by the user (e.g., physician) in an effort to change the degree of anteversion of the acetabular cup such that it matches the target anteversion. The acetabular cup of the hip implant can be manipulated using any number of techniques as is known in the art as discussed above.

After the manipulation of the acetabular cup at step 2335, the method returns to step 2310, where a fluoroscopic image of the pelvic region is taken. The three lines are then drawn again at step 2315 by the user and superimposed over the acetabular cup in the fluoroscopic image. Next, at step 2320 the degree of anteversion is again measured based on the drawn lines, and the measured anteversion of the cup is then compared with the target anteversion at step 2325. If the measured anteversion and the target anteversion match, then method ends at step 2330, but if not, then the method again moves to step 2335 where the acetabular cup of the hip implant is again manipulated by the user (e.g., physician) in an effort to change the degree of anteversion such that it matches the target anteversion.

With regard to the methods above, the user (e.g., physician) can interact with the radiographic and/or fluoroscopic images via the graphical user interface (GUI) of the imaging software. Exemplary screens of the GUI as shown on the computing device executing the imaging software are shown at FIGS. 24-26. For example, FIG. 24 shows a pre-surgery screen in which the user (e.g., physician) can enter the target inclination, anteversion, and teardrop length of the patient. Similarly, FIG. 25 shows a screen during surgery in which lines are superimposed over the acetabular cup in the image, and the angle of inclination for the acetabular cup is calculated. Likewise, FIG. 26 shows a screen during surgery in which three lines are superimposed over the acetabular cup in the image, and the degree of anteversion for the acetabular cup is calculated. It should be understood that the screens of the GUI for the imaging software shown in FIGS. 24-26 are example screens, and as such can be modified in other suitable ways, as known in the art.

As shown and described herein, the present application includes techniques to modify a distorted C-arm (Fluoroscopy) image that is recorded on a mobile C-arm (Fluoroscopy) unit in an operating room during a THA. Due to parallax, the dimensions of an image are changed and the magnification and distortion of the image can change with increasing distance from the central beam. In order to measure components on the C-arm image, a correction factor can be applied to correct the image and eliminate the parallax error.

Figure 29:
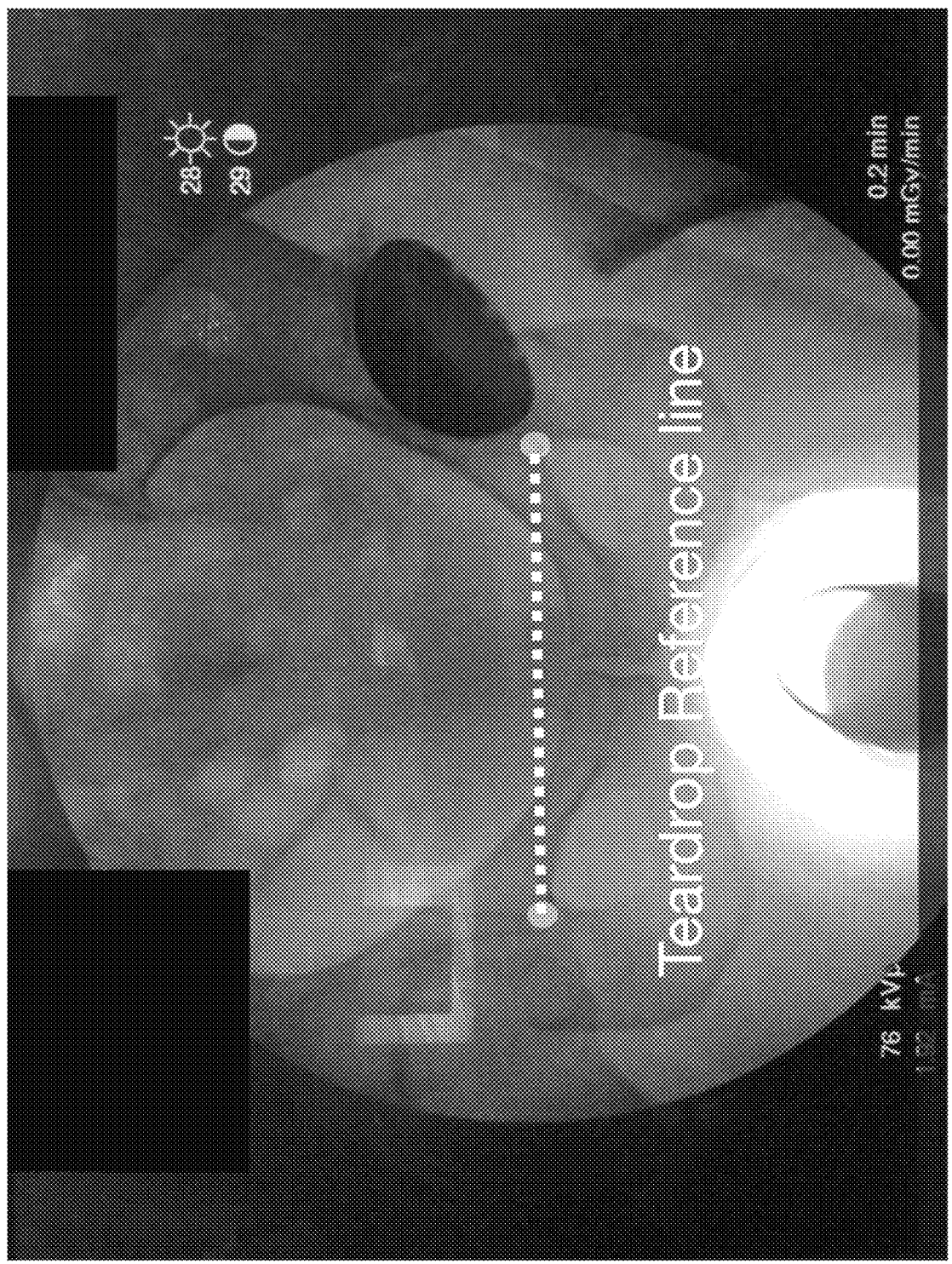

FIGS. 27-34 illustrate a technique regarding modification of the image, including prior to measuring a distance or angle. The raw image as recorded on the fluoroscopy unit screen and is displayed in FIG. 27. Anatomic reference points for the measurement of a distance or angle are identified as in FIG. 28. In the example illustrated in FIG. 28, the tear drop anatomic location is marked on the left and right side. Moreover, a connecting ("orientation") line between the anatomic landmarks, can be used to describe tilt or orientation of the pelvis on the image (FIG. 29).

Figure 30:
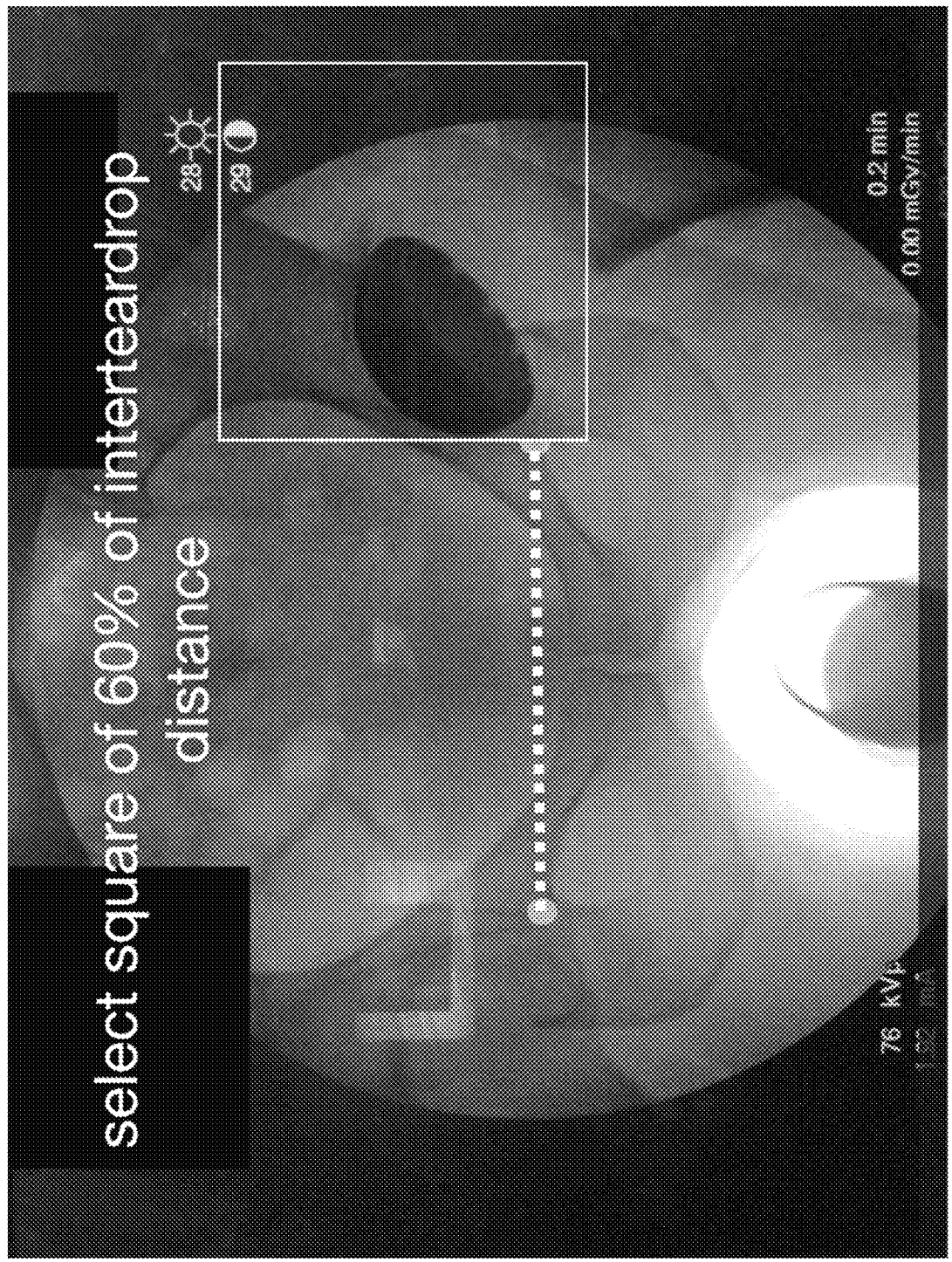

Continuing with reference to FIGS. 27-34, an area of interest (acetabular component in this example) is selected. The size of the area of interest can be determined in reference to the orientation line (FIG. 29) and may be, for instance, a square with a size of 60% of the length of the distance between the reference points (FIG. 30). The position of the reference square can be guided by the reference points (e.g., tear drop in FIG. 28) and the overall orientation of the image.

Figure 31:
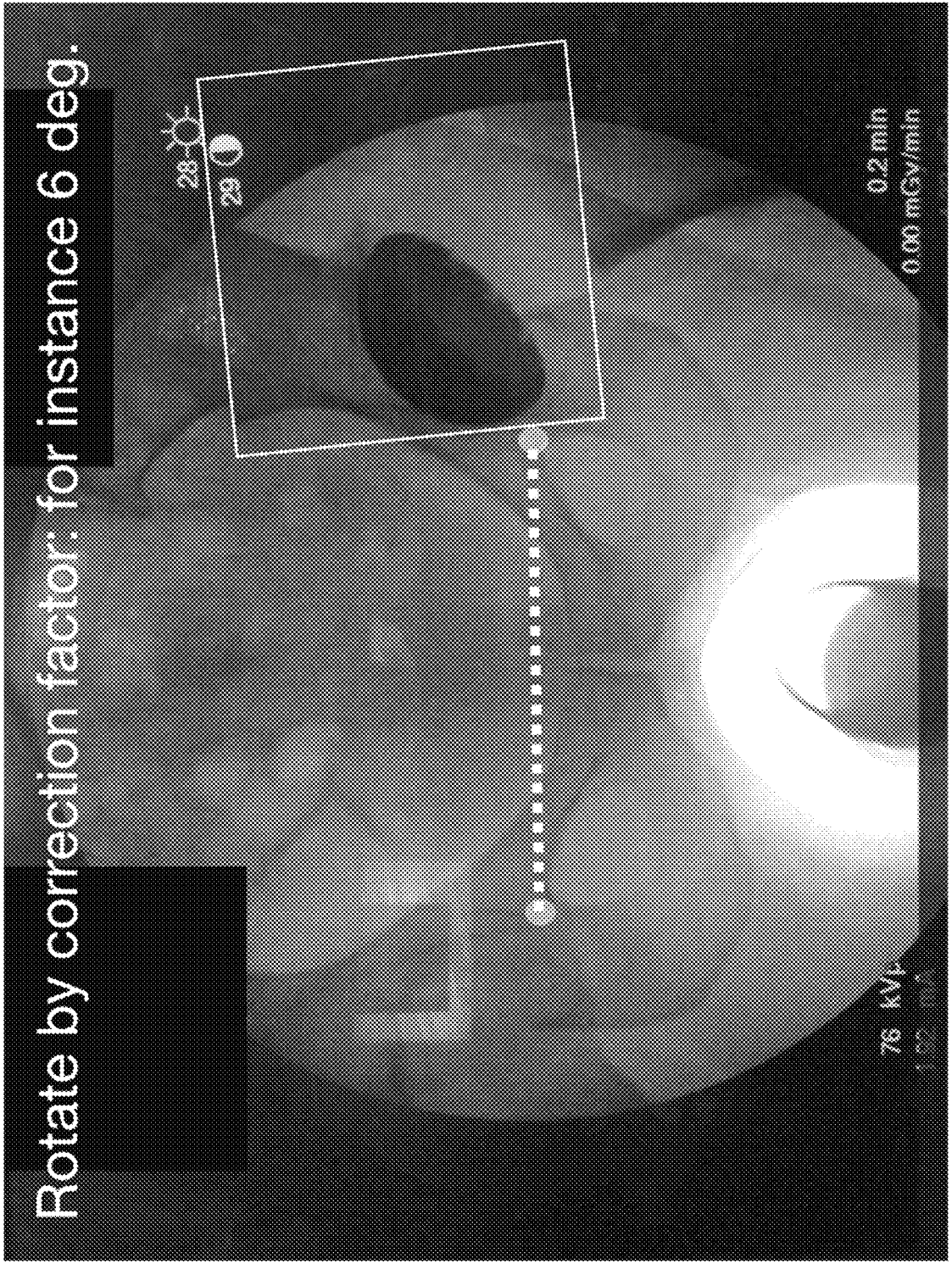
Figure 32:
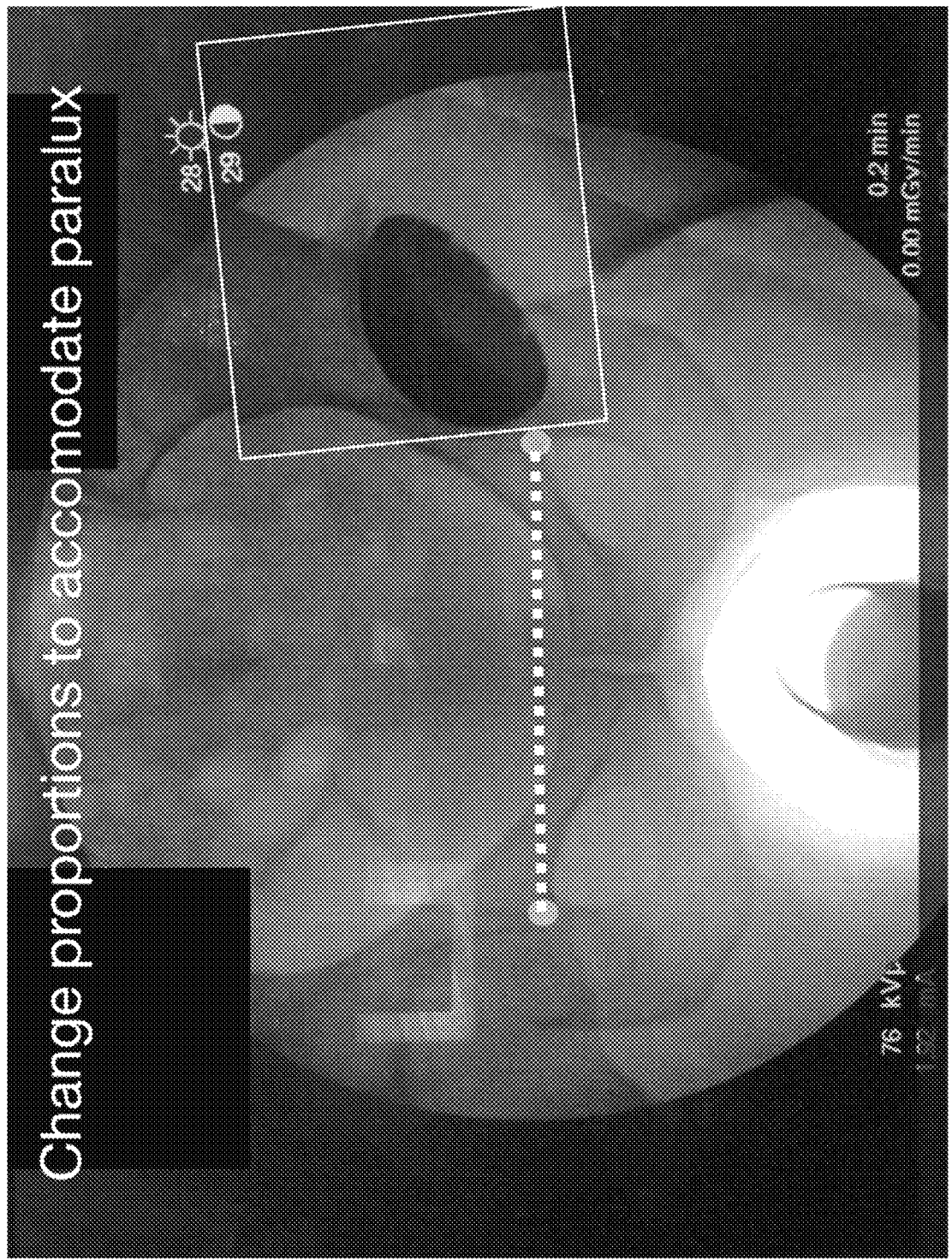
Figure 33:
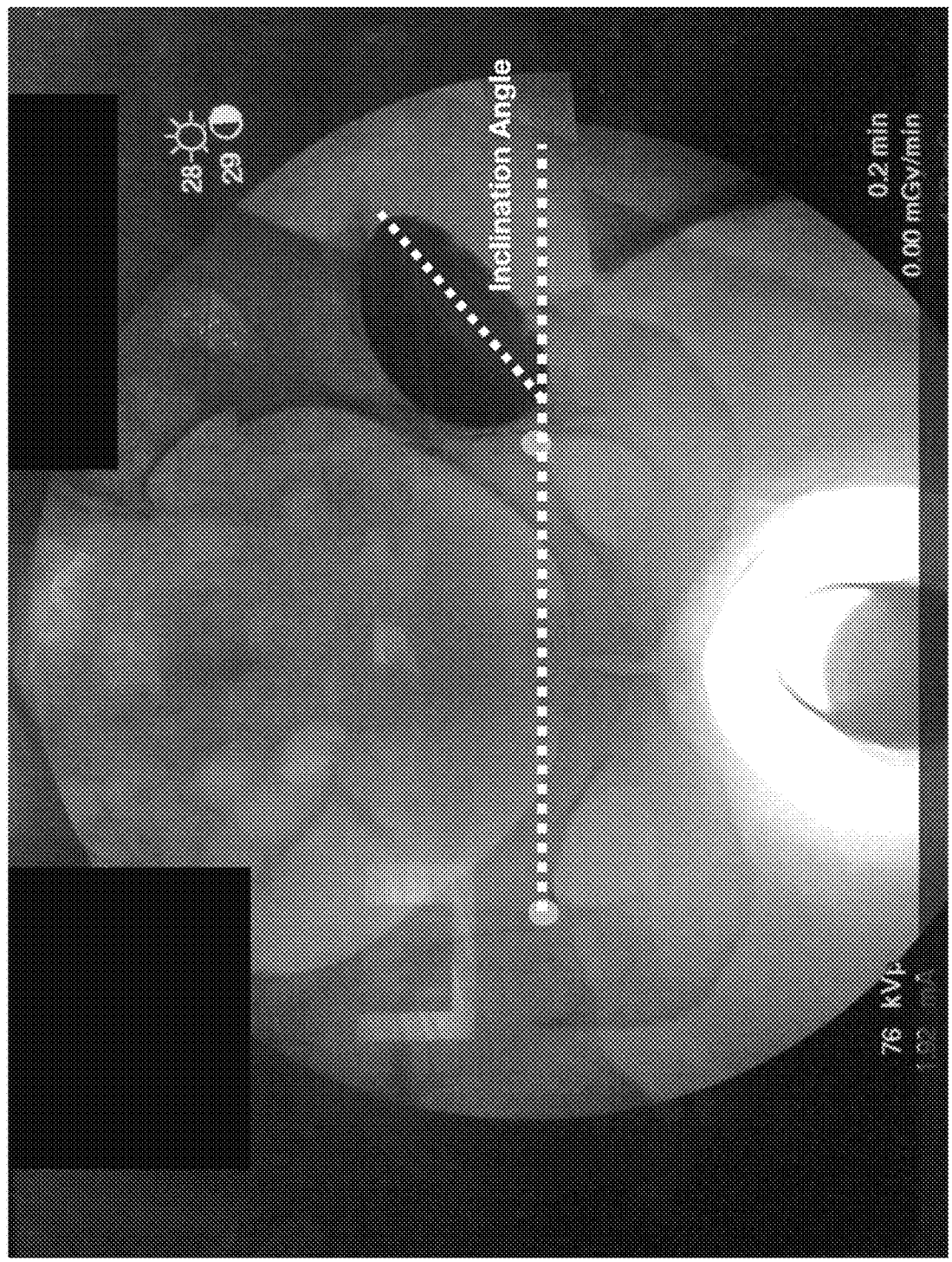
Figure 34:
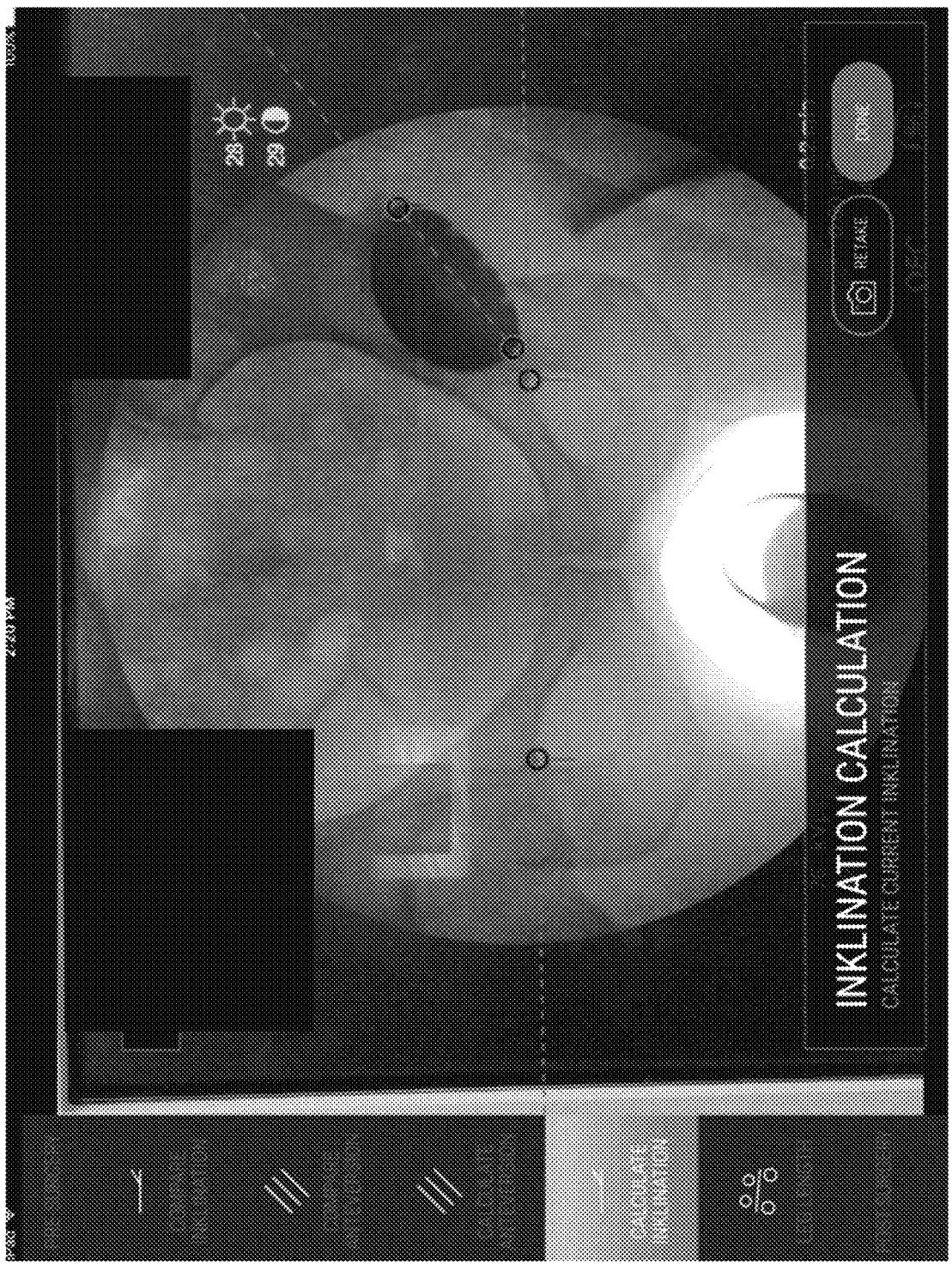

The so selected area of interest within the image is, thereafter, rotated and positioned in a correction angle (in this example 6 degrees) off the reference line (FIG. 31). Since parallax image distortion might not just affect the angle of an area of interest but also its proportion, the present application describes an adjustment of the proportion with changing aspect ratios to accommodate for the image distortion by parallax (FIG. 32). In the corrected image, measurements can now be performed as visualized in FIG. 33. Here the inclination or abduction angle of the cup is measured in the post processed image correcting the parallax of the initial image (FIG. 34).

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present application need not reside on a single computer or processor, but can be distributed in a modular fashion amongst a number of different computers or processors to implement various aspects of the systems and methods disclosed herein.

The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present application.

What is claimed:

1. A fluoroscopy-based method for generating an inclination angle of an acetabular cup during total hip arthroplasty, the method comprising:
   capturing, by a respective imaging device, an anterior posterior image of a patient's pelvis from an image including a surgical area having an acetabular cup inserted in the patient's pelvis;
   measuring, by a computing device, an inclination angle of the acetabular cup in the image;
   accessing, by the computing device, a database of stored calibration data, wherein the calibration data include a respective correction factor for each of a plurality of respective imaging devices, further wherein each respective correction factor accounts for image distortion associated with the respective imaging device;
   receiving, in a graphical user interface provided by the computing device, a selection of one of the plurality of respective imaging devices;
   processing, by the computing device, the selection to access respective calibration data associated with the selected one of the plurality of respective imaging devices;
   generating, by the computing device as a function of a correction factor included in the calibration data associated with the selected one of the plurality of respective imaging devices and as a function of the measured inclination angle, a revised inclination angle of the acetabular cup, wherein the revised inclination angle accounts for image distortion associated with the selected one of the plurality of respective imaging devices; and
   providing in the graphical user interface, the revised inclination angle.

2. The method of claim 1, wherein the image distortion is parallax image distortion that affects a measured angle of an area of interest and/or a proportion of the angle.

3. The method of claim 2, wherein the parallax distortion results from the acetabular cup location being outside a central beam of the respective imaging device.

4. The method of claim 1, further comprising:
   instructing, by the computing device, a robotic element to position a C-arm of the respective imaging device to move a central beam associated with the respective imaging device until the acetabular cup appears spherical.

5. The method of claim 1, wherein the correction factor is generated using at least one previously captured interoperative fluoroscopic image and at least one postoperative radiographic image.

6. The method of claim 1, wherein the correction factor is generated as a function of a calculated differences between inclination angles measured in at least one interoperative fluoroscopic image and at least one postoperative radiographic image.

7. The method of claim 1, wherein the correction factor is generated as a function of an average of calculated differences between a plurality of inclination angles measured in a plurality of interoperative fluoroscopic images and a plurality of postoperative radiographic images.

8. The method of claim 1, wherein the respective imaging device is a model of a fluoroscope.

9. A fluoroscopy-based system for generating an inclination angle of an acetabular cup during total hip arthroplasty, the system comprising:

a computing device configured with a processor and non-transitory processor readable memory that includes programming code that, when executed, configures the processor to:

capture, by a respective imaging device, an anterior posterior image of a patient's pelvis from an image including a surgical area having an acetabular cup inserted in the patient's pelvis;

measure, by a computing device, an inclination angle of the acetabular cup in the image;

access, by the computing device, a database of stored calibration data, wherein the calibration data include a respective correction factor for each of a plurality of respective imaging devices, further wherein each respective correction factor accounts for image distortion associated with the respective imaging device;

receive, in a graphical user interface provided by the computing device, a selection of one of the plurality of respective imaging devices;

process, by the computing device, the selection to access respective calibration data associated with the selected one of the plurality of respective imaging devices;

generate, by the computing device as a function of a correction factor included in the calibration data associated with the selected one of the plurality of respective imaging devices and as a function of the measured inclination angle, a revised inclination angle of the acetabular cup, wherein the revised inclination angle accounts for image distortion associated with the selected one of the plurality of respective imaging devices; and provide in the graphical user interface, the revised inclination angle.

10. The system of claim 9, wherein the image distortion is parallax image distortion that affects a measured angle of an area of interest and/or a proportion of the angle.

11. The system of claim 10, wherein the parallax distortion results from the acetabular cup location being outside a central beam of the respective imaging device.

12. The system of claim 9, wherein the non-transitory processor readable memory further includes programming code that, when executed, configures the processor to:

instruct a robotic element to position a C-arm of the respective imaging device to move a central beam associated with the respective imaging device until the acetabular cup appears spherical.

13. The system of claim 9, wherein the correction factor is generated using at least one previously captured interoperative fluoroscopic image and at least one postoperative radiographic image.

14. The system of claim 9, wherein the correction factor is generated as a function of a calculated differences between inclination angles measured in at least one interoperative fluoroscopic image and at least one postoperative radiographic image.

15. The system of claim 9, wherein the correction factor is generated as a function of an average of calculated differences between a plurality of inclination angles measured in a plurality of interoperative fluoroscopic images and a plurality of postoperative radiographic images.

16. The system of claim 9, wherein the respective imaging device is a model of a fluoroscope.

* * * * *